(12) United States Patent
Zuker et al.

(10) Patent No.: US 7,479,373 B2
(45) Date of Patent: *Jan. 20, 2009

(54) METHOD FOR IDENTIFYING COMPOUNDS MODULATING TASTE TRANSDUCTION

(75) Inventors: Charles S. Zuker, San Diego, CA (US); Jon E. Adler, Washington, DC (US); Nick Ryba, Bethesda, MD (US); Ken Mueller, San Diego, CA (US); Mark Hoon, Kensington, MD (US)

(73) Assignees: The Regents of the University of California, Oakland, CA (US); The United States of America as represented by the Department of Health and Human Services, Washington, DC (US)

( * ) Notice: Subject to any disclaimer, the term of this patent is extended or adjusted under 35 U.S.C. 154(b) by 436 days.

This patent is subject to a terminal disclaimer.

(21) Appl. No.: 10/383,982

(22) Filed: Mar. 7, 2003

(65) Prior Publication Data

US 2003/0157568 A1 Aug. 21, 2003

Related U.S. Application Data

(63) Continuation of application No. 09/393,634, filed on Sep. 10, 1999, now Pat. No. 6,558,910.

(51) Int. Cl.
*G01N 33/53* (2006.01)
*G01N 33/567* (2006.01)
*C12P 21/06* (2006.01)
*C12N 1/20* (2006.01)
*C12N 15/74* (2006.01)

(52) U.S. Cl. ............... 435/7.2; 435/7.21; 435/69.1; 435/252.3; 435/471

(58) Field of Classification Search ............... None
See application file for complete search history.

(56) References Cited

FOREIGN PATENT DOCUMENTS

| WO | WO 93/16178 A2 | 8/1993 |
|---|---|---|
| WO | WO 98/13478 A2 | 4/1998 |
| WO | WO 99/42470 A1 | 8/1999 |
| WO | WO 00/38536 | 7/2000 |

OTHER PUBLICATIONS

Skolnick et al. Trends in Biotech. 18:34-39, 2000.*
Bork P. Genome Research 10:398-400, 2000.*
Doerks et al. Trends in Genetics 14:248-250, 1998.*
Smith et al. Nature Biotechnology 15:1222-1223, 1997.*
Brenner SE. Trends in Genetics 15:132-133, 1999.*
Bork, et al. Trends in Genetics 12:425-427, 1996.*
Kim et al., "Positional Cloning of the Human Quantitative Trait Locus Underlying Taste Sensitivity to Phenylthiocarbamide", *Science*, 2003, pp. 1221-1225, vol. 299.

Hillier et al., "The DNA sequence of human chromosome 7", *Nature*, 2003, pp. 157-164, vol. 424.
Adams, Mark D. et al.; "Sequence Identification of 2,375 Human Brain Genes"; *Nature*; Feb. 13, 1992; pp. 632-634; vol. 355.
Munzy, D. et al.; Database GenEmbl; Accession No. AC006518; May 1, 1999.
Herrada and Dulac: A Novel Family of Putative Pheromone Receptors in Mammals with a Topographically Organized and Sexually Dimorphic Distribution *Cell* 90: 763-773 (Aug. 22, 1997).
Matsunami and Buck: A Multigene Family Encoding a Diverse Array of Putative Pheromone Receptors in Mammals *Cell* 90: 775-784 (Aug. 22, 1997).
Striem et al.: Sweet tastants stimulate adenylate cyclase coupled to GTP-binding protein in rat tongue membranes *Biochem* 260: 121-126 (1989).
Ryba and Tirindelli: A New Multigene Family of Putative Pheromone Receptors *Neuron* 19: 371-379 (Aug. 1997).
Naito et al.: Putative pheromone receptors $Ca^{2+}$- sensing receptor in Fugu.*Proc. Natl. Acad. Sci.* 95: 5178-5181 (Apr. 1998).
Ian E. Lush : "The genetics of tasting mice" *Genet. Res. Camb.* 53 95-99 (1989).
Kinnamon and Margolskee: "Mechanisms of taste transduction" *Current Opinion in Neuriobiology* 6 506-513 (1996).
Hoon et al.: "Putative Mammalian Taste Receptors: A Class of Taste-Specific GPCRs with Distinct Topographic Selectivity" *Cell* 96 541-551 (Feb. 19, 1999).
Hoon and Ryba: Analysis and Comparison of Partial Sequences of Clones from a Taste-bud enriched cDNA Library *J. Dent Res.* 76: 831-838 (Apr. 1997).
Dulac and Axel: "A Novel Family of Genes Encoding Putative Pheromone Receptors in Mammals" *Cell* 83 195-206 (Oct. 20, 1995).
Chaudhari et al: "The Taste of Monosodium Glutamate: Membrane Receptors in Taste Buds" *Journal of Neuroscience* 16(12): 3817-3826 (Jun. 15, 1996).
Cao et al: "Cloning and localization of two multigene receptor families in goldfish olfactory epithelium" *Proc. Natl. Acad. Sci.* 95 11987-11992 (Sep. 1998).
Wong et al.: "Transduction of bitter and sweet taste by gustducin" *Letters to Nature* 381 796-800 (Jun. 27, 1996).
McLaughlin et al.: "Gustducin is a taste-cell-specific G protein closely related to the transducins" *Letters to Nature* 357 563-569 (Jun. 18, 1992).
Brown et al.: "Cloning and characterization of an extracelluar $Ca^{2+}$- sensing receptor from bovine parathyroid" *Letters to Nature* 366: 575-580 (Dec. 9, 1993).
Ming, D., et al., "Characterization and solubilization of bitter-responsive receptors that couple to gustducin," Proc Nat'l Acad Sci USA, 95 (1998) p. 8933-8938.

(Continued)

*Primary Examiner*—Robert Landsman
(74) *Attorney, Agent, or Firm*—Townsend and Townsend and Crew LLP

(57) ABSTRACT

The invention provides isolated nucleic acid and amino acid sequences of taste cell specific G-protein coupled receptors, antibodies to such receptors, methods of detecting such nucleic acids and receptors, and methods of screening for modulators of taste cell specific G-protein coupled receptors.

14 Claims, 28 Drawing Sheets

OTHER PUBLICATIONS

Ming, D., et al., "Blocking taste receptor activation of gustducin inhibits gustatory responses to bitter compounds," Proc Nat'l Acad Sci USA, 96 (1999) p. 9903-9908.

Höfer, D., et al., "Taste receptor-like cells in the rat gut identified by expression of α-gustducin," Proc Nat'l Acad Sci USA, 93 (1996) p. 6631-6634.

Journal of Cookery Science of Japan, 30[2] (1997) p. 68-73.

Wamsley, et al. "Human BAC clone GS1-113H23 from 5p15.2, complete sequence" *EMBL Database Entry AC003015, Accession No. AC003015*, Oct. 31, 1997.

Adams, et al. "Use of a random human BAC End Sequence Database for Sequence-Ready Map Building; CITBI-E1-2530B8.TF CITBI-E1 *Homo sapiens* genomic clone 2530B8, genomic survey sequence" *EMBL Database Entry AQ308694; Accession No. AQ308694*, Dec. 23, 1998.

Adler, et al. "A Novel Family of Mammalian Taste Receptors" *Cell* vol. 100, pp. 693-702, Mar. 17, 2000.

Chandrashekar, et al. "T2Rs Function as Bitter Taste Receptors" *Cell* vol. 100, pp. 703-711, Mar. 17, 2000.

\* cited by examiner

FIG. 1A

```
TATCACTACTGATTTCTCTGATGTTAAACATTTCATCATTAGGATGATGTATGATCATTTC
TCAATGATGTTTATGAAGGTAATATGTCTTATAATTGGTGGATTCAACACATTT
TCCCAGAATTTCTTATTCACAAACTCATCTAAGGTCTTCTTAATCGCCAATTCAT
CCCATGTTTTCTTACCCATCACACTCACTCTTCTCTCATGCTCATACCCTTCACAGTTTCC
CTGGTAGCTTTTTTCGTCCTCTTTCTCTCACTGTGAAGCATCACAAGAAGATGCA
GGTCAATGCAAAGGACCCAGAGATGCCAGCACCATGCCCACACAACAAAGCCTTGC
AAATTGGGTCTCCTCCTCCTGCTATGCAATATACTTACTTTCATTATCACA
GGAATTTGAACCTTGACTTGATGATGATGTATAGTAATACTTTATTTGACCACAT
ATCTGGAGCAGTTTTTCTATAAGCCACTCATTGTGCCTGCTCTTAGGTGCCGGTCCAAAGAT
AGCTGAGACAAGCCACTCTTCTGCTGCCTTGTCTTAGGTGCCGGTCCAAAGAT
ATGGACACTGTCGTTTCTAATAAATTCCAGAGTACATTATGCAAAATCTTGAGGG
TGATCAGTTCATAGAAAAAGTAATCTTAGAGGGGAAAATAAAATATTGGGCTTCA
AATGTTGGATGGGTAATACATAGGAAGGCAGGACAAGGATGAAGGAGACTAGCATT
ATATAAGTGATTCACAGGGAAATGGGAAGAGGGCTTTATATAAATGAAGAAGA
AGATAAATGATGAAGGATGAGGAAGAGTTAAATATGTAAAATGACAATAGAGATGG
CATCATGCCGTTTAAGAAATTTGAATGCATATGTATGTTTATATATTTTTAAT
TTTTATTGAATATATTATTACATTTAAATGTTATCCTGTTTCCCCACCCAAC
CTCCCACCTCCTCCCACCTCCCTGCCCTGACATTCCCCTGACTTCCCTGGGAATCCAGC
CTTGACAGGACCAAGGCTTCTCCACCAAGGCCATTCTCTTGGATGGTGGTTTA
ACATGTCAGCAGGAGCAGCCATGATCTGTCTATGTGTCTTGTTCTTATGTGTTGCAACTCCCT
GTCCCTGGGAGCTCTTCATCCTTCATGCTCGTAACTCCTCCAATGTGACCCTGTTCTCAGTCA
TCAGCTCCTTCAATCCTTCCTGTAACTCCTCCAATGTGACCCTGTTCTCAGTCA
ATGGTTGACTATGAGCATTCACCTCTGATTGTCATGCTCTGGCACAGCTTCTCA
GAAGACAGCTACATCAGTCTCTATAAGAGTGCACTTCATGGCATCAGCAATGTTG
TCTTGATTGGTGTCTGTATGTATATGGGCTGGATCCCAAACTTTGTCTTTATATCCCTATGAATAT
ATGGTCATTCCTCAGTCTTTATAAGAATGACTGAAGTATCCACACTTTGCCATCCTTCTTC
TTTTGTTCCCCCTTCATGTGGTCTGTGAATGACTGAATTGTACATTGTAATCCAAGCTTTGGGCTAA
ATGAGCTTCATGTGGTCTGTGAATGACTGAATTGTACATTGTAATCCAAGCTTTGGGCTAA
TATCCAATTATAGTGAGTGCATACCAAAAAAAAAAAAAAAAAAAAAAAAA
AAAAAAAAAAAAAAAAAAA
```

| rGR03 | >rGR03 aa | >rGR03 nt (cds pristine; 3'UTR not finished) |
|---|---|---|
| | MVPTQVTIFSIIMYVLESLVIIVQS CTTVAVLFREWMHFQRLSPVEIILI SLGISHFCLQWTSMLYNFGTYSRPV LLFWKVSVVWEFMNVLIFWLTSLLA VLYCVKVSSFSHPVFLWLRLKILKL VLWLLLGALIASCLSIIPSVVKYHI QMELLTLDHLPKNSSLIIRLQMFEW YFSNPFKMIGFGVPFLVFLISILL TVSLVQHWGQMKHYSSSSSLRAQC TVLKSLATFFIFFTSYFLTIVVSFI GTVFDKKSWFWVCEAVIYGLVCIHF TSLMMSNPTLKKALRLQFWSPESS | GCATGGTGCCAACCCAGTCACAATCTTCTCTATCATCATGTATGCTTGAGTCC TTAGTCATAATTGTGCAAAGTTGCACAACGGTTGCAGTGCTGTTCAGAGAGTGGAT GCACTTTCAAAGACTGTCGCCGTGGAAATAATTCTCATCAGCCTGGGCATTCAC ATTTCTGTCTACAGTGGACATCGATGCTGTACAACTTTGGTACTACTCTAGGCCT GTCCTTTTATTTTGGAAGGTATCGTGCTGTCTGGGAGTTCATGAACGTTTGACATT CTGGCTAACCAGTTTGCTTGCTGCTGAGTCCTCTACTGTGTCAAGTCTTCTTCTCTC ACCCCGTCTTCCCTGCTGATAGCTTCTTGTTGTCAATCATCATTTGAAACATCCCTTCTGTTCTCTGGTTGCTA TTGGGCGCTTCTCTGATAGCTTCTTGTTGTCAATCATCATTTTCTATCATCTTCAAAATGATTGGGTTT TATCCAGATGGAAATTACTCACCTAGATGTAATTTTCTATCATCTTACTACCAAAACAGTTCTTTGATTC CCAGCATTGGGGCAGATGAAAACATCACAGACAGCAGCCTCCAGCCTCCAGCCCTATTTT AGTGCACTGTCGAAGTCTCTTGCCACCTTCATCTCTTCTTCACATCCTATTT CTGACTATAGTGCTCGTCCTTTATTGGCACCGTGTTGATAAGAAGTCATGGTTCTG GGTCTGCGAAGCTGCATCTATGTTTAGTCGTTATTCACTTCACTTCCCTGATGA TGAGCAACCCTACACTGAAAAAGCACTCAGGTGCAGTTCTGGAGCCCAGAGTCT TCCTAAGGCAGGGAATTC IVS ACAAGGGAAAGTGACTCTTCAGATTTAAGTTTAAATTAGAAGAGAGATAAATTC CCaAGCTTTCACTCCTAAGGCTAAAGATAGGCTGTGTAGGTAGTTATTCTGAGCA CATTGGCACATCACCATTGTCAGTACTTGAGGTTTGAATGAAGCTCACTCAAAGA ACTTGGAAAGAAGGTGGTCTTcTGACATCAATCAAGAAACAAGCTTTCCTCCTAC TTCTTCCCTAAATGCAACAACCTAAGAATTATCCACAAGATGATGGCGCAAGGGT TCCTCAATCAATTTCAGGATGTACATCAATGCGCAGCCTATACTACACCGAAAAG AAGGCATGGGTCTTAAAAAGTAAAGGGGATATCAAAAAAATTCGAACCAAACAAA AAGTGGCACACATTAAGCTAGGTCTATGTTTGGTCAGTCCTACACCTGGAGAAGGGG GACATTGGTCAGCTCATTCGAACACTGTCAAGTCTTCATCGAAAAAAAAAAAAAAAA TATTACCCATTAAACCTCAGTCTCATCGAAAAAAAAAAAAAAAA |

FIG. 1C

| rGR04 | >rGR04 aa<br>MLSAAEGILLCVVTSEAVLGVLGDT<br>FIALANCMEYAKNKKLSKIGFILIG<br>LAISRIGVWIIILQGYMQVFFPHI<br>LTFGNITEYITYIWVFLNHLSVWFA<br>TNLNILYFLKIANFSNSVFLWLKSR<br>VRVVFIFLSGCLLTSWLLCFPQFSK<br>MLNNSKMYWGNTSWLQQQKNVFLIN<br>QSLTNLGIFFFIIVSLIITCFLLIVF<br>LWRHIRQMHSDGSGLRDLNTEAHVK<br>AMRVLISFAVLFILHFVGLSIQVLC<br>FFLPQNNLLFITGLIATCLYPCGHS<br>IILILGNKQLKQASLKALQLQHLTC<br>CETKRNLSVT | >rGR04 nt (3'UTR not finished)<br>TGGTTCCATCACATGACAATAGGCTTGAAAAACTTGCAGATAGAGAAGACATAACC<br>CCTCCAACAAGAAGCCAACATATGGGACATTCTCCAGCAGATAATTTATAACAGAT<br>GCAACGGGAGCAACTTCGAGATCTGCAAAGATGCTGAGTGCAGCAGAAGGCATCCT<br>CCTTGTGTTGTCACTAGTGAGGCAGTGCCAAGTGGGGTTTAGGAGACACATTCATTG<br>CACTTGCAAACTGCATGAGTATGCCAAGAACAAGAAGCTCTCTAAGACTTGGTTTC<br>ATTCTCATTGGCTTGGCGATTCTTCCACACATACTTGGTGTCGTATGGATAATAATTTACA<br>GGGGTATATGCAAGTATTTTTTCCACATCTCCTTTGGAAACATAACATGAAT<br>ATATTACTTACATATGGGTGTTTCTCAATCACTTAAGTGTCTGGTTTGCTACCAAC<br>CTCAAATATCCTACTTCTAAAGATAACAAATTTTCAACTCGTATTTCTCTG<br>GCTGAAAAGTAGAGTCCGTGGTTTTACTTCTCGTCAGGATGCTTACTTACCT<br>CGTGGTTACTATGTTTCCACAATTTCAAAGATGCTAACAACAGTAAAATGTAC<br>TGGGAAACACGTCTTGGCTCCAGCAGCAGAAAAATGTCTTCCTTATTAACCAAG<br>TTTAACCAATCTGGGAATCTTCTTTTCATTATTGTATCCCTGATTACCTGCTTC<br>TGTTGATTGTTTTCCTCGGAGACACATCAGGCAAATGCACTCAGATGGTTCAGGA<br>CTCAGAGACCTCAACACAGAAGTCATGTGAAAGCCATGAAAGCCACTGAGAGTTCTAATATCTTT<br>TGCCGTACTCTTTATCCTGCATTTCGTAGGTTCTTTCCATACAAGTGCTATGCTTAT<br>TCCGCCAAAACAACTACTCTTATAACTGGTTTGATAGCCACATGCCTCTAT<br>CCCTGTGTCACTCAATCATCTTAATTCTAGAAACAGCAGCTGAAGCAAGCCTC<br>CTTGAAGGCACTGCAGCACTTAACGTCCATGTGTTCCATGATTTATTCCACTGATCTCTGCATTGTCCATTGATGAGC<br>CATAAATGGGTTGCCAATTAATATCTGCCATGTTATTCCACTGATTCTTGTCCTGATCTGTCCATGATCTGATGAGC<br>GTGGGGTTGAAATCTCCGACTATTGTTGTCGACTATTGGTCTTTGCATTGTGAATGAAATGTGCTCTTGAGC<br>TTTAGTAAGAATTCTTTTGTGAATGTAGGTGCTTTTGCATTGTCTTTGATGAATATGAAGTGTCCTT<br>TAAGATTGAGAGTTCAGCTTGATGACTTCTTGATGAACGTCAATTTTATTGATATTAGATTG<br>GCTTATCTTTTTTGATGATGCTTCTTGATGTCTGTCTCTGAGGTGTGTTCCTGCATTCAGCCATT<br>GCAACTCAAGATTGCTTCTCTGAGTCATTGTTGCTTGGAAAGTTGTTTTCAGCCATT<br>TACTCTGAGGTAGTGTCTCTGTCTCTTTACATATCCAGTT<br>ATGCTGGGTCCTCTTTACATATCCAGTT<br><br>... approximately 1100 bp ...<br><br>AAGTCCAGCCCCTCCCCCACAGATTTAGTGCAGGAGCTGTTGACCACTTCA<br>ATTCAGTCCTGGGTGTAGACCAGAACCACAGTAAAAAGAATGACTTCATTAAAT<br>TAGCAGACAAATGGGTGGAACTAGAAATGTCATCCTGGGCTGAGAGATGGCTCA<br>GTGGTTCAGACCACTGCGCTCTTCCAGAGTCCTGAGTTCAATTCCAACAACT<br>ATATGGTGGCTACCAACCATTACATGAGATCAGATGCCCTCTTGTGTATCTG<br>AAGAGAGTGACCAGTGTACTTACATACATAAATAAATAAATCTAAAAAAATG<br>TTAAAAA |

FIG. 1D

| rGR05 | >rGR05 aa<br>MLGAMEGVLLSVATSEALLGIVGNT<br>FIALVNCMDCTRNKNLYNIGFILTG<br>LAISRICLVWILITEAYIKIFSPQL<br>LSPINIIELISYLWITSQLNWFA<br>TSLSIFYFLKIANFSHHIFLWLKRR<br>INIVFAFLIGCLLMSWLFSFPVVVK<br>MVKDKKMLYINSSWQIHMKKSELII<br>NYVFTNGGVFLLFIIMVIGCFLLII<br>SLWRHSKMWQSNESGFRDLNTEVH | >rGR05 nt<br>AAGAGATTCAGATACTACCACCACAAACATTTTTAAATATATGTAAGTCTTAAAGA<br>AAGAAGGGAAAGCCACTCCTTATTGAGCAGCCAATAGATTGCCATCTTAAAATTC<br>TGTGGCAGAAGCTATTTAAAGATCTGCGAGATGCTGGGTGCAATGGAAGGTGTC<br>CTCCTTTCAGTTGCAACTAGTGAGGCTTTGCTTGGCATTGTGAGGAACACATTCAT<br>TGCACTTGTGAACTGCATGGACTGTACCAGGAACAAGAATCTCTATAATATTGGCT<br>TCATTCTCACTGGCTTGGCAATTTCTCGAGAATCTGCCTCGTGTGCTATCAACAATAATTGA<br>GAGGCATACATAAAATATTCTCCACAGTTGCTGCAATTGCAATGTTGGTTTGCTACCA<br>ACTCAGTATCTTTTTATTCTCCAGTAGTTTTTGCCTTCCTGATAGGGTGCTACTTAT<br>GCCTCAGTATCTTTTTATTCTCCAGTAGTTTTGCCTTCCTGATAGGGTGCTACTTAT<br>GTCATGGCTATTTCTTCCAGTAGTTGTGAAGATGTTAAAGATTCAGTTAATCATTAAC<br>TGTATATAAACTCATCTTGGCAAATCCACATGAAGAAAGTCAGTTAATCATTAAC<br>TATGTTTTCACCAATGGGGGAGTATTTTACTTTTATAATAATGGTAATTCAAATGAAT<br>TTTTCTCTTAATTATTCCCTTTGGAGACACAGCAAGTGGATGCAATCAAATGAAT<br>CAGGATTCAGAGATCTCAACACAGAAGTTCATGTG |

FIG. 1E

| | | |
|---|---|---|
| mGR01 pseudogene | >mGR01 aa<br>MLRHCSKENECLGDGFIGFVNCMDW<br>VKRRKLFLVNQLLTLLVISRITVL*<br>VLLLNCWLYN*YFFFTVNSYF**FY<br>KN | >mGR01 nt<br>GAATTCAATTTTCTTTCCTCTGTAACAGAAGGTCATACATAACTCCTGTATGA<br>AGTACATATTGTAAAGAAGGTTCAGCTTATTACTGAATGTGTTCATTTCATATG<br>GAAAACATAATTGAGTTTCATGAAGCAGATACTACTCATATTTAGATGAACTAAT<br>TAAGTAATATTCAGGAATGACTGATGTTGAGACATTGTTCTAAGGAGAATGAG<br>TGTTTGGGAGATGAATTTATAGAGATTTGTGAACTGCATGGACTGGGTCAAGAGAAG<br>AAAGCTCTTTTGGTGAATCAACTCCTCACTCTTGTCATGGTCATCTCCAGAATCACTG<br>TCCTCTGAGTACTACTTCTAAATTGTTGGCTATATAACTAATATTTTTTTTTTACT<br>GTAAACTCTATTTTGATGATTCTATAAGAATTC |
| mGR02 | >mGR02 aa<br>NSSSVPGDPLESTCRHASLVFLLGN<br>LMQSMLEERFYQYGRNTSVNTMSND<br>LAMWTELIFFNMAMFSVIPFTLALI<br>SFLLIFSLWKHLQKMQLISRRHRD<br>PSTKAHMNALRIMVSFLLLYTMHFL<br>SLLISWIAQKHQSELADIIGMITEL<br>MYPSVHSCILILGNSKLKQTSLCML<br>RHLRCRLKGENITIAYSNQITSFCV<br>FCVANKSMR | >mGR02 nt<br>GGAATTCGAGCTCGGTACCCGGGGATCCTCCTAGAGTCGACCTGCAGGCAAGC<br>TTGGTGTTCTGCTTGGAAATCGATGGAAGCATGCTTGAAGAGAGGTTCTATCA<br>ATATGGAAGGAACACAAGTGTGAATACCATGAGCAATGACCTTGCAATGTGACCG<br>AGCTGATCTTTTCAACATGGCTATGTTCTCTGTAATACCATTACATTGGCCTTG<br>ATTTCTTTCTCCTGCTAATCTCTCTTTGTGGAAAACATCTCCAGAAGATGCAGCT<br>CATTTCCAGAAGACACAGAGACCCTGCTCTATACCAAGCCACCATGGCTCGCTCCAGA<br>TTATGGTGTCCTCCTGCTCTATACCAAGCACCATGGCCAAGATGCCTTGAGAA<br>TGGATTGCTCAAAAGCATCAGAGTGAACTGGCTGATATTATTGGTATGATAACTGA<br>ACTCATGTATCCTTCAGTCCATTCAGTGCTGAGGCATTTGAGATGTAGGCTGAAAGGAGAGAAT<br>AGCAGACTTCTCTTGTATGCTGAGGCATTTGAGATGTAGGCTGAAAGGAGAGAAT<br>ATCACAATTGCATATGAGGTAGTTGTTCAAGGAATCCTTCCTGACTTATTGTATCATGAA<br>CAAATCTATGAGTGGGGAGTCTGAAAGAGCTGTCTTCTGTAAGCAAGGTTTGTATACACTA<br>GTCATATGGGGAGTCTGAAAGAGCTGTCTTCTGTAAGCAAGGTTTGTATACACTA<br>GTGGGCTGGGACCACCAAACCAAGCACAAACCTAGCTATAACCTATCCTGGCTGC<br>AGGATATGCTGAACAATGGTGGCTTGCACAGCAGAAGCTCATGCCACCTCTGCCTGAT<br>AGTCTAACTTGAGGCCATTCCACAGCAGAAGCTCATGCCACCTCTGCCTGAT<br>GGCCAGGAAGCAAAATCTGTTGATGGCCCAAGACCTATGGTAAACTGAACACTACTG<br>GAAAAGAAGAAAGACTCGTGTAATGATCTATCAAATATTCCTAATGATATTCTGAT<br>AAACTCATATATTAGTCCCTGTCCTAATCATCATCCAAATAGTAAGTTCCCAGCAC<br>CTGATGGGAGCAGATAGAAGGAACAATTATGAGAGCCAGAGTGATCCAGAACACTAGGAT<br>CACTTAAGAATCAACTAAGCACATGCATGCAGTCTACACTAAGTCCTCTGTATATACTGTG<br>CACAGAATCAACTAAGCACATGCAGCATGCATAGGGTTAATGGAGACTGAAGTGGCAATCA<br>CAGAGCCTGCATAGGTCTACACTAAGTCCTCTGTGTATATACTGTGGCTGTTTAGC<br>TTAGGAATTTGTTGGACTCCTAACAATGGATAAGGAATTCTGCAGATATCCATCA<br>CACTGCCGCCCCGTCGAG |

| mGR04 | >mGR04 aa<br>MLSALESILLSVATSEAMLGVLGNT<br>FIVLVNYTDWVRNKKLSKINFILTG<br>LAISRIFTIWIITLDAYTKVFLLTM<br>LMPSSLHECMSYIWVIINHLSVWFS<br>TSLGIFYFLKIANFSHYIFLWMKRR<br>ADKVFVFLIVFLIITWLASFPLAVK<br>VIKDVKIYQSNTSWLIHLEKSELLI<br>NYVFANMGPISLFIVAIIACFLLTI<br>SLWRHSRQMQSIGSGFRDLNTEAHM<br>KAMKVLIAFIILFILYFLGILIETL<br>CLFLTNNKLLFIFGFTLSAMYPCCH<br>SFILILTSRELKQDTMRALQRLKML | >mGR04 nt<br>CTGCAGCAGTAAATCACACCAGATCCAGCAGAAGCCTTCTTGGAAATTGGCAGAG<br>ATGCTGAGTGCACTGGAAAGCATCCTCCTTGTCGTGGCCACTAGTGAAGCCATGCT<br>GGGAGTTTTAGGGAACACATTTATTGTACTTGTAAACTACACAGAGACTGGGTCAGGA<br>ATAAGAAACTCTCAAGATTAACTTTATTCTCACTGGCTTAGCATTTCCTTCTGACTAT<br>TTTACCATATGGATAATAACTTTAGATGCATATACAAAGTTTTCCTTCTGACTAT<br>GCTTATGCCGAGCAGTCTACATGAATGCATGAGTTACATATGGGTAATTATTAACC<br>ATCTGAGCGTTTGGTTTAGCACCAGCCTCGGATGAAGAAGCTGATAAAGTTTTGT<br>AATTTTCCCACTACATATTCTCTGGATGAAGAGAAGAGCTGATAAAGTTTTGT<br>CTTTCTAATTGTATTCTTAATTATAAATATCAGAGCAACACATCCTGGCTGATCCACCTG<br>AGTTCATTAAAGATGTTACTTATAAACTATGTTTTGCCAATATGGGGCCATTCCCT<br>GAGAAGAGTGAGTTACTTATATAAACTATGTTTTGCCAATATGGGGCCATTCCCT<br>CTTTATTGTAGCCATAATTGCTTGTTTCTGTTAACCATTTCCCTTTGGAGACACA<br>GCAGGCAGATGCAATCCATTGGATCAGGATTCAGAGATCTCAACACAGAAGCTCAC<br>ATGAAAGCCATGAAATGTTTAATTGCATTATCATCCCTCTTATCTTATATTTTTT<br>GGGTATTCTCATAGAAACATTATGCTTGTTCTTACAAACATAAACTTCTCTTTA<br>TTTTTGGCTTCACTTGTCAGCCATGTGCCATTCCTTTGCCATTCCTTATCCTAATT<br>CTAACAAGCAGGGAGCTGAAGCAAGACACTATGAGGGCACTGCAGATTAAAAAT<br>GCTGTGAGACCCTTTGACAnAGAAATGAATGTTCTGGCACAGTTCAAGCAGGAATCC<br>CTGGAGCCCTTTCCATTCCCACTATGTTCTCACACTGTCTTTAGTTGAATTGTTAA<br>AAGTTTTGAAACCTTTGGCAACTTGATTGACTGCAGCTACGCCAGTGTAAGATTT<br>CATAGTAAGACAAACATTGAAAATAAGACTTCTCAGTCTTATTCATTGAGTTTC<br>TAAAGCATTGACACCCATTCACCAGAAAAACCAAAGGGAAGAGAGAGCCAGAGGGATGC<br>ACATGTGATGAATCTTGATATTTAGGACATGGAATTGAGGAGCCAGAGGGATGC<br>TACCGTGTGTCTACAGCTTTGTTGTTGAGTAGTGGTGAAAATCATGCAGTAGATCTGTGGG<br>TAAAGTAGAGCTTGGAGTAGTGGTGTTTCTGAACAGAAGACCAGAGACTGATTGAAC<br>AGTTGGTTGAGGAAGCAGGCTGTTCTGAACAGAAGACCAGAGACTGATTGAAC<br>TGGTCATTGTGTATATCAAAAATAGTGATTTCAGATGAAGCCAAGTTGTGAGCAA<br>AGATATCTGAGGAAGAATTC |

FIG. 1H

| mGR05 | >mGR05 aa<br><br>MLSAAEGILLSIATVEAGLGVLGNT<br>FIALVNCMDWAKNNKLSMTGFLLIG<br>LATSRIFIVWLLTLDAYAKLFYPSK<br>YFSSSLIEIISYIWMTVNHLTVWFA<br>TSLSIFYFLKIANFSDCVFLWLKRR<br>TDKAFVFLLGCLLTSWVISFSFVVK<br>VMKDGKVNHRNRTSEMYWEKRQFTI<br>NYVFLNIGVISLFMTLTACFLLIM<br>SLWRHSRQMQSGVSGFRDLNTEAHV<br>KAIKFLISFIILFVLYFIGVSIEII<br>CIFIPENKLLFIFGFTTASIYPCCH<br>SFLILSNSQLKQAFVKVLQGLKFF | >mGR05 nt<br><br>CTGCAGCAGATCTACTATAGATGCAACAGATACAACTTGAGGACCTGGAGATATG<br>CTGAGTGCGGCAGAAGGCATCCTCCTTGCATTGCAACTGTTGAAGCTGGGCTGGG<br>AGTTTAGGAACACATTATTGCACTGGTAAACTGCATGGACTGGGCCAAGAACA<br>ATAAGCTTCTATGACTGGCTTCCTTCTCATGGCTTAGCACTATTCTACCAAGTAGTA<br>ATTGTGTGGCTATTAACTTTAGATGCAATATGCAAAGCTATTCTATCCAAGTAGTA<br>TTTTCTAGTAGTCTGATTGAAATCATCTCTTATATATGAACTGTGAATCACC<br>TGACTGTCTGTTTGCCACCAGCTAAGCATCTTCTATTCCTGAAGATAGCCAAT<br>TTTTCCGACTGTGTATTTCTCTGTTGAAGAGGAGAACGATAAAGCTTTGTTTT<br>TCTCTGGGGTGTTTGCTAACTTCATGGGTAATCTCCTTCATTGTGTGAAGG<br>TGATGAAGGACGGTAAAGTGAATCATAGAAACAGACCTCGGAGATGTACTGGGAG<br>AAAAGGCAATTCACTATTAACTACGTTTTCTTTGTTAATTATGTCACTTTGGAACACAGCA<br>TATGATGACCTTAACTGCTCGTGTTTCAGGATTCAGAGACCTCAACACAGAAGCTCATGTG<br>GGCAGATGCAGTCTGGTTTCAATTCAATTTATTCTGCATATATCCTTGCTGTCACTCATTATTCTAATTCTA<br>AAAGCCATAAAATTTTAATTCATTATCATCCTTTGCGTCACTCATTATTCTAATTCTA<br>TGTTTCAATAGAAATTCACAACTGCATCCATAATCCTTGCTGTCACTCATTATTCTAATTCTA<br>TTGGTTTCACACAGTCAGTTCAGGATTCAGAGAGTCTAAAGCTACTGCAAGGATTAAAGTTCTT<br>TCTAACAGCCAGTCAAGCAAGCCTTGTAAAGGTACTGCAAGGATTAAAGTTCTT<br>TTAGAAAAGAAAAGCTCTCAGGTGCACATGCGTCTGAAACAGTCTTTTCATGTGCACAGTGTTCTTTGCAT<br>GAATAATAATGAGGGAATCATAAAAGTCTTTTCATGTGCACAGTGTTCTTTGCAT<br>tgGgGTTtGGgAAGAtGtAA |
| mGR06 | >mGR06 (partial aa)<br><br>MLTVAEGILLCFVTSGSVLGVLGNG<br>FILHANYINCVRKKFSTAGFILTGL<br>AICRIFVICIIISDGYLKLFSPHMV<br>ASDAHIIVSYIWVIINHTSIWFAT<br>SLNLFYLLKIANFSHYIFFCLKRRI<br>NTVFIFLLGCLFISWSIAFPQTVKI<br>FNVKK | >mGR06 nt<br><br>CTGCAGCAGTAAAAAAAAAGCTAAAATAGTTATAGTTGCAGCAGAAGCAAC<br>GTTAGGGATCTGTAGAGATGCTGACTGCTAGCAGAAGGAATCCTCCTTGTTTGT<br>AACTAGTGGTTCAGTCCTGGGAGTTCTAGGAAATGGATTATCCTGCATGCAAAC<br>TACATTAACTGTGTCAGAAAGAAGTTCCACAGCTGGCTTTATTCTCACAGGCT<br>TGGCTATTTGCAGAATCTTTGTCATATGTATAATAATCTCTGATGAGTATTTAAA<br>ATTGTTTTCTCCACATATGGTTGCCTCTGATGCCCACATTATGTGATTCTTAC<br>ATATGGTAATTATCAATCATACAAGTATATGGTTGCCACCAGCCTCAACCTCT<br>TCTATCTCCTGAAGATACAGTATTATCTTCTCCTGGGATGCTTATTATATCATGGTCA<br>AAGAATCAATACAGTCAGTCAAAACAGTCAGTGAAGATATTTAATGTTAAAAAGC<br>ATTGCTTTCCCACAAACAGTCAGTGAAGATATTTAATGTTAAAAAGC |

FIG. 1I

| | | |
|---|---|---|
| mGR07 | >mGR07 aa<br>NSAEGILLCVVTSEAVLGVLGDTYI<br>ALFNCMDYAKNKKLSKIGFILIGLA<br>ISRIGVVWIIILQGYIQVFFPHMLT<br>SGNITEYITYIWFLNHLSVWFVTN<br>LNILYFLKIANFSNSVFLWLKRRVN<br>AVFIFLSGCLLTSWLLCFPQMTKIL<br>QNSKMHQRNTSWATSGKILLLPK | >mGR07 nt<br>gAATTCAGCAGAAGGCATCCTCCTTGTGTTGTCACTAGTGAGGCTGTGCTCGGAG<br>TTTTAGGGACACACATATATTGCACTTTTAACTGATGGACTATGCTAAGAACAAG<br>AAGCTCTCTAAGATCGGTTCATTCTCATTGGCTTGGCGATTCCAGAATTGGTGT<br>TGTATGGATAATAATTTTACAAGGTATATACTTACAAGTATTTTTCCACACATGCTTA<br>CCTCTGGAAACATAACTGAATATATTACTTACATATGGTATTCTCAATACTACTTA<br>AGTGTCTGGTTTGTCACCAACTCAACATCCTACTTTCTAAGATAGCTAATTT<br>TTCCAACTCTGTATTCTCTGGCTGAAAAGGAGAGTCAATGCAGTtTTTATCTTTC<br>TGTCAGGATGCTTACTTACCTCATGGTTACTATGTTTTCCACAAATGACAAAGATA<br>CTTCAAAATAGTAAAATGCACCAGAGAAAACACATCTTGGGCCACCAGCCAAAAAT<br>ACTTCTATTACCAAAG |
| mGR08 | >mGR08 aa<br>MLWELYVFEAASVFLNFVGIIANL<br>FIIVIIKTWVNSRRIASPDRILFS<br>LAITRFLTLGLFLLNSVYIATNTGR<br>SSLLFHIFSIVLEVSGCKQ | >mGR08 nt<br>GGCATTCCTAAGAAAATAAGAACAGGAGTGAAGAAATAGTAATTAATCCTTGAAA<br>GATTTGCATCTCAGTAAAGCAGCTCCTTCCAGGCTGCCATCTCTAGACAGAAATGGTGTTTGCCATG<br>CTGGAAAATAAAAAGGAGACCTCTTCACACCCTGCATCCTGTGTCTGCTTACTTAT<br>TTCAGTTGTTGTTTGCGCCTCGGTTTTTTAAATTTGTAGGAATCATTGCAAATCTATT<br>TATTATAGTGATAATTATTAAGACTTGGGTCAACACTACTGGCCATCACAATACTGGAGGTCAAGTCTCGTTAGTGACCATT<br>ATAGGATCCTGTTCAGCTTCAGTCACATTGCTACAAATACTGGAGGTCAAGTCTCGTTAGTGACCATT<br>CTGAACAGTGTCTACATTGTGTGGAAGTTCTGATGCAAACATAATTTCAACACCCAGKGtTTCTCT<br>CTGAACAGCTTGTATTGTGTGAAArATACTAATTTCAACACCCAGKGtTTCTCT<br>GtTGAAACGaCTATCTcTATGAAGAGACCCCaACCTGCTGTGGCCTGtCTTnTGan<br>TTCAaCcCTmCCacTCTcTaTaTATgCTCCaCaAWaTTnACGtTTnCTG<br>aACCATaAtTgGGaGaAaWGacacCGcAtTTGacCTcAgnaTgGnATCtTgaCGn<br>TAGtAGccCTTGckGCCgaaCTCcaKtWTacAtGnttGtCtgTAnnTgCTcAnn<br>AGGGACCTTTGCTTCCTTGTAAAACATTCCTGGnAnAnAA |
| mGR09 | >mGR09 aa<br>MEHLLKRTFDITENILLILFIELI<br>IGLIGNGFTALVHCMDWVKRKKMSL<br>VNKILTALATSRIFLLWFMLVGFPI<br>SSLYPYLVTTRLMIQFTSTLWTIAN<br>HISVWFATCLSVFYF | >mGR09 nt<br>GAATTCAGAAATCATCAAAAATACTTCAAAACTACATGTTTAAAATAGCACTTCAA<br>ATGAATACATTtGCAAATCTTTACAACTAATACATAAAATGGAGCATCTTTGAAG<br>AGAACATTTGATATCACCGAGAACATACTTCTAATTATTTATTCATTGAATAAT<br>AATTGGACTTATAGGAAACGATTCACAGCCTTGGTGCACTGCATGACTGGGTTA<br>AGAGAAAAAAATGTCATTAGTTAATTAAAATCCTACCGCTTGGAACTTCTAGA<br>ATTTTCCTGCCTCGTCATGCTAGTAGCTAGTAGCTAGTAGTCACTGACTATAGCTA<br>TTTAGTTACTACTAGACTAGATGATGATACAGTTCACTAGTACTCTATGACTATAGCTA<br>ACCATATTAGTGTCGGTTTGCTACATGCCTACATTAGCCTCAGTGTCTTTATTTCT |

FIG. 1J

| | | |
|---|---|---|
| mGR10 | >mGR10 aa<br>MFSQIISTSDIFTFTIILFVELVIG<br>ILGNGFIALVNIMDWTKRRSISSAD<br>QILTALAITRFLYVWVMI | >mGR10<br>CTGCAGAGAATTCAACATCTTATTCAACTTCAGAAAACTGGATATTAGACACAGTGTC<br>TGGATGAAGCAGCAGAGTGATGTCTCTTTTGGGAAAAAAAGCCAAGTAGTCATAAAGAATT<br>TATGAAACAATTCCTGGGATTGTTTATATTGTTACAAACAAATTATATGTTTGT<br>TAGTCAGTAATGTAGTGCTTTTAAATGTaGCAGAAACATTAAAAATGAAGCATGTCT<br>AAAACATGTAATAAGCACCAGTGATATTTTACTTTTACAATAGATATTATTGTGGA<br>CACAGATAATAGGAATTTTAGAAATGGATTCATAGCACTAGTAATATCATGACT<br>ATTAGTAATAGGAGAGAAGCATTTCATCAGCGGATCAGATTCTCACTGCTTGCCATT<br>GGACCAAGAGAGAAGCATTTCATCAGCGGATCAGATTCTCACTGCTTGCCATT<br>ACCAGATTCTCTATGTGTGGGTTATGATCATTGTATATTGTTATTCATGCTGnG<br>CCCACATTGCTTACCAGATCAGAAATAGTnACATCAATTGGTnTTATTTGGATAG<br>nGAATAACCATTTCAGCCGTTGGCTTGCCCCATGCCTCGGGnCTTTATTTTnT<br>GAAGATAGCCAAnCTTTCTAACCCCTTGTTTCTTTTACCGTAATTACAnGGnnTTCAATGATTTTnTTGG<br>GAAAAAAGTAAGTTTTTAATGGATAATAACCnTGGTnTTGGACCAGnTnTCCCn<br>ATTTTTAAACCCGTTnTnCnTTTAAACCnTGGTnTTGGACCAGnTnTCCCn |
| mGR11 | >mGR11 aa<br>KNYFLINQSVTNLGIFFFIIVSLIT<br>CFLLIVELWRHVRQMHSDVSGFRDH<br>STKVHVKQMKFLISEMVFFILHFVG<br>LSIEVLCFILPQNKLLFITGLTATC<br>LYPCGHSIIVILGNKQLKQASLKAL<br>Q | >mGR11 nt<br>GGAAAATTACTTCTTATTAACCAAAGTGTGACCAATCTGGGAATCTTTTTCTTC<br>ATATTGTATCCCTGATTACCTGCTTTCTGTTGATTCAGGACACATGT<br>CAGACAAATGCACTCAGATGTTCAGGATTCAGAGACCACAGCACAAAGTACATG<br>TGAAAGCTATGAAATTCTAATATCTTTATGGTCTTCTTTATTCTGCATTTGTA<br>GGCCTTTCCATAGAAGTGCTATGCTTTATTCTGCCACAAAATAAACTGCTCTTAT<br>AACTGGTTTGACAGCCAGTAAAGCaAGCCCTCTTTGAAGGCACTGCAG<br>TAggAAATAAGCAGTTAAAGCaAGCCCTCTTTGAAGGCACTGCAG |
| mGR13 | >mGR13 aa<br>EFIMGTLGNGFIFLIVCIDWVQRRK<br>ISLVDQIRTALAISRIALIWLIFLD<br>WVSVHYPALHETGKMLSTYLISWT<br>VINHCNFWLTANLSILYFLKIANFS<br>NIIFLYLKFRSKNVVLVTLLASLFE<br>LFLNTVIIKIFSDVCFDSVQRNVSQ<br>IFIMYNHEQICKFLSFTNPMFTFIP<br>FVYVH | >mGR13 nt<br>GAATTCATAATGGAACCTTAGGAAATGGATTCATTTCTGATAGTCTGCATAGA<br>CTGGGTCCAAAGAAGAGAAAAATCTCTTAGTGGATCAAATCCGCACTGCTCTGGCAA<br>TTACCAGAATCGCTCTAATTTGGTTCTGATATTCCTAGATTGGTGGTGTCTGTTCAT<br>TACCCAGCATTACATGAAACTGGTAAGATGTTATCAACATATTGATTTCCTGGAC<br>GGTGATCAATCATTGTAACTTTCTACTGCAAACTGAGCATCCTTATTTTC<br>TCAAGATGCCAACTTTCTAACATTATTTTCTTATCTAAAGTTTAGATCTAAA<br>AATGTGTATTAGTGACCCGTTAGCGTCTGTGTTTGATAGTGTTCAAAGAAATGTGTCTC<br>AATTATAAAAATATTTCTGATGTGTATAACCATGAACAAATTTGCAAATTCTTTCCTTTACTAAC<br>AAATTTCATAATGTATAACCATGAACAAATTTGCAAATTCTTTCCTTTACTAAC<br>CCTATGTTCACATTCATACCTTTTGTTTATGTCCAC |

FIG. 1K

| | | |
|---|---|---|
| hGR01<br><br>nt:AC003015(BAC from 5p15.2; nt 54851-55750)<br>GSS:AQ308694,AQ316999, AQ277039<br>EST:AA416581 | >hGR01 aa<br><br>MLESHLIIYFLLAVIQFLLGIFTNG<br>IIVVVNGIDLIKHRKMAPLDLLLSC<br>LAVSRIFLQLFIFYVNVIVIFFIEF<br>IMCSANCAILLFINELELMLATWLG<br>VFYCAKVASVRHPLFIWLKMRISKL<br>VPWMILGSLLYVSMICVFHSKYAGF<br>MVPYFLRKFFSQNATIQKEDTLAIQ<br>IFSFVAEFSVPLLIFLFAVLLIFS<br>LGRHTRQMRNTVAGSRVPGRGAPIS<br>ALLSILSFLILYFSHCMIKVFLSSL<br>KFHIRRFIFLFFILVIGIYPSGHSL<br>ILILGNPKLKQNAKKFLLHSKCCQ | >hGR01 nt<br><br>ATGCTAGAGTCCACCTCATTATCTATTTCTTCTGCAGTGATACAATTCTTCT<br>TGGGATTTTCACAAATGGCATCATTGTGGTGGTGAATGGCATTGATCAAGC<br>ACAGAAAAATGCTCCGCTGATCTTCTACGTTAAGTGATTGTTATCTTCTCATAGAATT<br>TTTCTGCAGTGTTCTGCAATTCTGCAATTCTGTGCAATTTGTGCTATCTTCTCATAGAATT<br>CATCATGTGTTCTGCAATGGCTCGGCGTTTCTGAAGTTGCCAGGCGTCGTCAC<br>GGCTTGCCACATGGCTCGGCGTTTCTGAAGATGAGAAATCCAAGCTGGTCCCATGATGCCT<br>CCACTCTTCATCTGGTTGAAGATGAGAAATCCAAGCTGGTCCCATGATGATCCT<br>GGGGTCTCTGCTATATGTATCTATGATTGTGTTTCCATAGCAAATGCAGGGT<br>TTATGGTCCCATATCTTCCTAAGACAGATTTTCTCCAAGAAATTTTCTCCTTTGTTGCTGAGTTCTCAGTGCCATT<br>GAAGATACACTGGCTATACACTTCCTTTTGCTCTGTTTGCTCTTTGATTTCTCTGAGTTCTCAGTGCCATT<br>GCTTATCTTCCTTTTGCTGTTTTGCTCTTTGATTTCTCTCTGGGAGGCACACCC<br>GGCAAATGAGAACATCAGTGCCGGCACAGGTTCTCGATCCTCCTACTTCTCCCACTGATGAT<br>AGCGCGTGCTGTCTATCCTCTCTAAGTTCACATCAGAAGTTCATCTTCTGTTCT<br>AAAGTTTTCTCTGATTGGTATATACCCTCTGGACACTCTCTCATCTTAATTTAGA<br>TCATCCCTGTGATTGGTATATACCCTCTGGACACTCTCTCATCTTAATTTAGA<br>AATCCTAAATTGAAACAAAATGCAAAAGTTCCTCCCTCCACAGTAAGTGCTGTCA<br>GTGA |
| hGR02<br><br>likely pseudogene<br><br>nt:AC005541 (PAC; nt 4413-3504)<br>GSS:AQ711250,AQ6161919). | >hGR02 aa<br><br>MALSFSAILHIIMMSAEFFTGITVN<br>GFLIIVNCNELIKHRKLMPIQILLM<br>CIGMSRFGLQMVLMVQSFFSVFFPL<br>LYVKIIYGAAMFLWMFFSSISLWE<br>ATCLSVFYCLKISGFTQSCFLWKF<br>RIPKLIPWLFWEAFWPL*ALHLCVE<br>VDYAKNVEEDALRNTTLKKSKTKIK<br>KISEVLIVNLALIFPLAIFVMCTSM<br>LLISLYKHTHRMQHGSHGFRNANTE<br>AHINALKTVITEFCFFISYFAAFMT<br>NMTFSLPYRSHQFFMLKDIMAAYPS<br>GHSVIIILSNSKFQQSFRRILCLKK<br>KL | >hGR02 nt<br><br>ATGGCCCTGTCTTTTTCAGCTATTCTTCATATTATCATGATGTCAGCAGAATTCTT<br>CACAGGGATCACAGTAAATGGCTAAAATGCCAATTCAAATCCTTCATTAACTGTTAATGAATTGATCA<br>AACATAGAAAGCTAATGCCAATTCAAATCCTCTAAGTGTCATAGGATGTCTAGA<br>TTTGGTCTCGAGATGTTAATGTGCCACAAGTTTTTCTCGTTGTTCTTTCCACT<br>CCTTACGTACAAAATAATTATGTGCCAATGATGTTCCTTTGATGTTTTTA<br>GCTCTATCGCCTATGGTTTGCCACTTGCCTTCTGTATTACCTCCAAGATT<br>ACCTTGGCTGCTTCTGGGAAGCGTTCTGGCCTCTGGAGCATTGCATCTGTGTC<br>GAGTAGATTACGCTAAAATGTGAAGAGGATGCCCTCAGAACACCACACTAAA<br>AAGAGTAAACAAAGATAAAGAAATTAGTGAAGTGCTTCTGTCACTTGGCAT<br>TAATATTCCTCTAGCCATATTGTGATGCAACATGGATCTCATGGCTTAGAAATGCCAACAC<br>TACAAGCACACTCATCGATGCAACACATGGATCTCATGGCTTTAGAAATGCCAACAC<br>CTTATTTGCTTATGCTGAAGACACATAATGGCAGCATATCCCTCGGCCACTCGGTTAT<br>CAGTTCTTATGCTGAAGACACATAATGGCAGCATATCCCTCGGCCACTCGGTTAT<br>AATAATCTTGAGTAATTCCAACAATCATTAGTTCCAACAATCATTAGAAGAATTCTGCCTCA<br>AAAGAAACTATGA |

FIG. 1L

| | |
|---|---|
| hGR03<br><br>nt:AC004979 (PAC from 7q31.3-q32; nt 17576-18526) | >hGR03 aa<br>MMGLTEGVFLILSGTQFTLGILVNC<br>FIELVNGSSWFKTKRMSLSDFIITT<br>LALLRIILLCIILTDSFLIEFSPNT<br>HDSGIIMQIIDVSWTFTNHLSIWLA<br>TCLGVLYCLKIASFSHPTFWLKWR<br>VSRVMVWMLLGALLLSCGSTASLIN<br>EFKLYSVFRGIEATRNVTEHFRKKR<br>SEYYLIHVLGTLWYLPPLIVSLASY<br>SLLIFSLGRHTRQMLQNGTSSRDPT<br>TEAHKRAIRIILSFFFLFLLYFLAF<br>LIASFGNFLPKTKMAKMIGEVMTME<br>YPAGHSFLILILGNSKLKQTFVMLR<br>CESGHLKPGSKGPIFS<br><br>>hGR03 nt<br>ATGATGGGACTCACCGAGGGGTGTTCCTGATTCTGTCTGGCACTCAGTTCACACT<br>GGGAATTCTGGTCAATTGTTCATTGAGTTGGTCAATGGTAGCAGCTGGTTCAAGA<br>CCAAGAGAAGTCTTGTTCTGATTCATCATCACCACCCTGGCACTCTTGAGGATC<br>ATTCTGCTGTGTATTATCTTGACTGATAGTTTTAATAGAATTCTCCCACAC<br>ACATGATTCAGGATAATAATGCAAATTATGATGTTCCTGGACATTACAAACC<br>ATCTGAGCATTGGCTTGCCACCATTCCTGCTCTTGGCTCAAGTGGAGAGTTTCTAGGTGATGGT<br>AGTTTCTCACCCCACATTCCTGCTCTTCTGGCTCAAGTGGAGAGTTTCTAGGTGATGGT<br>ATGGATGCTGTTGGGTGCACTGCTCTATTCTGGGGAATTGAGGCCACCAGAATGTGACT<br>ATGAGTTTAAGCTCAGAAAGAAGAGTAGTAATTCTGCCTGACACGACTTTCTGCTCATCTCT<br>GAACACTTCAGAAAGAAGAGTAGTTATATCTGACCATGTCTTGCTCATCTCT<br>GTGTACCTGCCTCCCTTAATTGTGTCCCTGGCCTCCTACTCTTTGCTCATCTCT<br>CCCTGGGAGGCACACGGCAGATGCTGCAAAATGGACAAGCTCCAGAGATCCA<br>ACCACTGAGGCCCACAGAGAGGCCATGACAGAATCATCCTTTCCTTCTTCTTCTCTT<br>CTTACTTTACTTCTGTTCTTTAATTGCATCATTGGTAATTTCCTACCAAAA<br>CCAAGATGCTAAGATGATTGGGCGAAGTAAGATAAAGCAGACATTTATCCTGCTGGCCAC<br>TCATTATTCATTCTGGAGTCTGGTCATCTGAAGCCTGATCCGAAGCCATTGTAGTGATGCT<br>CCGTGTGAGTCTGGTCATCTGAAGCCTGATCCGAAGGACCCATTTCTCTTAG |
| hGR04<br><br>nt: AC004979 (PAC from 7q31.3-q32; nt 31906-32805) | >hGR04 aa<br>MLRLFYFSAIIASVILNFVGIIMNL<br>FITVVNCKTWVKSHRISSSDRILFS<br>LGITRFLMLGLFLVNTIYFVSSNTE<br>RSVYLSAFFVLCFMFLDSSSVWFVT<br>LINILYCVKITNFQHSVFLLLKRNI<br>SPKIPRLLLACVLISAFTTCLYITL<br>SQASPFPELVTTRNNTSFNISEGIL<br>SLVSLVLSSSLQFINVTSASLLI<br>HSLRRHIQKMQKNATGFWNPQTEAH<br>VGAMKLMVYFLILYIPYSVATLVQY<br>LPFYAGMDMGTKSICLIFATLYSPG<br>HSVLIITHPKLKTTAKKILCFKK<br><br>>hGR04 nt<br>ATGCTTCGGTTATTCTATTCTGCTATTATTGCCTCAGTTATTTTAAATTTGT<br>AGGAATCATTATGAATCTGTTATTACAGTGGTCAATTGCAAAACTGGGTCAAAA<br>GCCATAGAATCCTCTTCAGTGTTCTGTTCAGCCTGGCATCACCAGGTTT<br>CTTATGCTGGGACTATTCTGGTGAACACCATCTACTTCGTCTCTCAAATACGGA<br>AAGGTCAGTCAGTCTACCTGGTTGTCTGACCTGTTGCTCAATATCTTGTTGTACTGTGTGAAGATTACTAAC<br>GCAGTCGTCTGTCTGTCTGACCTGTTGCTCAATATCTTGTTGTACTGTGTGAAGATTACTAAC<br>TTCCAACACTGCAGTGTTCTCCTGCTGCTTAAGCGGAATATCTCCCCAAAGATCCCAG<br>GCTCCTGCTGGCCTGGCCTGTGCCTGTGCTGATTTCTGAACTTGTGACTCAGCTTCCACCACTGCCTGCTACATCACGC<br>TTAGCCAGGCATCACCTTTGTCACCTTTGAACTTGTGACTACGAGAATAACACATCATT<br>AATATCAGTGAGGGCATCTTGTCTTGTCTTTAGTGGTTCTTGGTCTTGAGCTCATCTCT<br>CCAGTTCATCATTAATGCAGAAAAATGCCACTGGTTTCTGAATCCCCAGACGAAGCT<br>CATGTAGGTGCTATGAAGCTGATGGTCTATTCCTCATCCTCTACATTCCATATTC<br>AGTTGCTACCCTGTCCAGTATTTGTCTGATTTTGCCACCCTTACTCTCCAGACATTCGTTCTCATT<br>AATCCATTGTCTGATTTTGCCACCCTTACTCTCCAGACATTCGTTCTCATT<br>ATTATCACACATCCTAAACTGAAAACAACAGCAAAGAAGAATTCTTTGTTTCAAAAA<br>ATAG |

FIG. 1M

| hGR05  nt: AC004979 (PAC from 7q31.3-q32; nt 43779-44678) | >hGR05 aa<br>MLSAGLGLLMLVAVVEFLIGLIGNG SLVVWSFREWIRKFNWSSYNLIILG LAGCRFLLQWLIILDLSLFPLFQSS RWLRYLSIFWVLSQASLWFATFLS VFYCKKITTFDRPAYLWLKQRAYNL SLWCLLGYFIINLLLTVQIGLTFYH PPQGNSSIRYPFESWQXLYAFQLNS GSYLPLVVFLVSSGMLIVSLYTHHK KMKVHSAGRRDVRAKAHITALKSLG CFLLLHLVYIMASPFSITSKTYPPD LTSVFIWETLMAAYPSLHSLILIMG IPRVKQTCQKILWKTVCARRCWGP | >hGR05 nt<br>ATGCTGAGCGCTGGCCTAGGACTGCTGCTGATGCTGGTGGCAGTGGTTGAATTTCTCAT CGGTTTAATTGGAAATGGAAGCCTGGTGGTCTGGAGTTTAGAGAATGGATCAGAA AATTCAACTGGTCCTCATATAACCTCATTATCTGGGCTGGCTGGAGTTTAGAGAATGGATCAGAA CTCCTGCAGTGGCTGCTGCTATCTTAGTATCTTCTAGTCTCTTAGCTCTCGGGTGCTTGTTCCACTTTGCCAGTGTT CCGTTGGCTTCGCACCTTCGTGCTGCCACCTTCGTGCTGTCCTGTAAGCCAGGCCAGTTAT GGTTTGCCACCTTCGTGCTGCCACCTTCGTGCTGTCCTGTAAGAAGATCACGACCTTCGATCGC CCGGCCTACTTGTGGCTGAAGCAGAGAGGCCTATAACCTGAGTCTCTGTGCCTCT GGGCTACTTTATAATCAATTGTTACTTACAGTCCAAATTGGCTTAACATTCTATC ATCCCAAGGAAACAGCAGCATTCGTATCCCTTTGAAAGCTGGCAGTACCTG TATGCATTTCAGCTCAATTCAGGAAGTTATTTGCCTTTAGTGGTGTTCTTGTTTC CTCTGGGATGCTGATTGTCTCTTTGTATACACACAAGGCTATTCGGATCAAGTCATT CAGGCCTATCCTGCTTACTTCCTGATCTGCATTCTCTCATATTGATCATGGGGATTCCTAGGGTGAAG CAGCCTATCCTGCTTACTTCCTGATCTGCATTCTCTCATATTGATCATGGGGATTCCTAGGGTGAAG CAGACTGTGTCAGAAGATCCTGTGGAAGACAGTGTTGCTCGGAGAGATGCTGGGGCCC ATGA | 
|---|---|---|
| hGR06  pseudogene  nt: AC004979 (PAC from 7q31.3-q32; nt 41231-42053) | >hGR06 aa<br>MLAAALGLLMPIAGAEFLIGLVGNG VPVVCSFRGWVKKM*GVPINSHDSG K*PLSPTQADHVGHKSVSTFPEQWL ALLS*CLRVLVSQANM*FATFFSGF CCMEIMTFVXXXXXXXXXXXXXX XXXXLLVSFKITFYFSALVGWTL*K IAVQ*R PLTGSNILHPILNLFL*RHHRKMEDH RLIAICDVSVPLVFL*SPSDLTILA TAVRRLKPRXXXXXXXXXXXXXXXX LYMVSALARHFSMTF*SPSDLTILA ISATLMAVTSFPSIVMVRNQTCQ RIL*EMICTWKS | >hGR06 nt<br>ATGTTGGCGGCTGCCCTAGGATTGCTGATGCCCATTGCAGGGGCTGAATTTCTCAT TGGCCTGGTTGGAAATGGAGTCCCTGGTTCGTGCTCTCAGTTTTAGAGGATGGGTCAAAA AAATGTAAGGAGTCCCTATAAATTCGACATAAGTCTGTTTCCACTTTCCCAGAGCAGTGTT ACTCAGGCCGATCATGTTGGACATAAGTCTGTTTCCACTTTCCCAGAGCAGTGTT GGCTTTACTATCTTAAGTCTTCGACATAAGTCTGTTTCCACTTTCCCAGAGCAGTGTT CCACTTTCTTCAGTGGCTTCTGCATGGAGATCATGACCTTTGTCCCGCTGACT TCTTGTAGCTGAAAAGACTGGGTTTTTGTTTCTAGTGTCTTTCAAGATACT TTTATTTCTCAGCTCTGTTGGCTGGACCTTGTTAAATCTGTTATTTATAGATTGCTGTCCAGTGAA CAACATCCTGATTGCTATTTGTGATGTTCTGTTCCATTGTCTTTTTGTAAAGACAT GGAGACTGATTGCTATTTGTGATGTTCTGTTCCAGGAGGAGGCTCAAACCAAGGTGCTC CACAGGAAGATGAGGACCACACAGCTGTCAGGAGGAGGCTCAAACCAAGGTGCTC ATCGCTCGAACTTCTAATCTCCCCTGATCTACATGTTTCTGCCATCTCTGCAACACTGAAG GACTTTTATACTTCATTCCGTCTATTGTAATGTTATGAGGAATCAGACTTCTAG CTGTTTATACTTCATTCCGTCTATTGTAATGTTATGAGGAATCAGACTTCTAG AGAATTCTGTAGGAGGAGATGATATGTACATGGAAATCCTAG |

FIG. 1N

| | | |
|---|---|---|
| hGR07<br><br>nt: AC006518 (BAC:<br>1481-525)<br>GSS:AQ388065<br>12p13 | >hGR07 aa<br><br>MADKVQTTLLFLAVGEFSVGILGNA<br>FIGLVNCMDWVKKRKIASIDLILTS<br>LAISRICLLCVILLDCFILVLYPDV<br>YATGKEMRIIDFFWTLTNHLSIWFA<br>TCLSIYYFFKIGNFFHPLFLWMKWR<br>IDRVISWILLGCVVLSVFISLPATE<br>NLNADFRFCVKAKRKTNLTWSCRVN<br>KTQHASTKLFLNLATLLPFCVCLMS<br>FFLLILSLRRHIRRMQLSATGCRDP<br>STEAHVRALKAVISFLLLFIAYYLS<br>FLIATSSYFMPETELAVIFGESIAL<br>IYPSSHSFILLGNNKLRHASLKVI<br>WKVMSILKGRKFQQHKQI | >hGR07 nt<br>ATGGCAGATAAAGTGCAGACTACTTTATTGTTCTTAGCAGTTGGAGAGTTTCAGT<br>GGGGATCTTAGGGAATGCATTCATTGATTCATTGGTAAACTGCATGGACTGGGTCAAGA<br>AGAGGAAAATTGCCTCCTAATACTATTAGATTGTTTATATTGGTGCTATATCCAGATT<br>TGTCTATTGTGCGTAATACTATTAGATTGTTTATATTGGTGCTATATCCAGATGT<br>CTATGCCACTGGTAAAGAAATGGAATCATTGACTTCTTCTGGACACTAACCAATC<br>ATTTAAGTATCTGGTTGCAACCTGCCTCAGCATTTCTAGTGGAGAATGACATAGT<br>AATTCTTCACCCACTTTCTCTCGATGAAGTGGAGAATTGACAGGGTGATTC<br>CTGGATTCTACTGGGGTGCGATTCAGTTTTGTGTGAAGGCAAAGAGGAAAACAAACTTA<br>AGAATTGAACGCTGATTCAGTTTTGTGTGAAGGCAAAGAGGAAAACAAACTTA<br>ACTTGGAGTTGCAGAGTAATAAAACTCAACATGCTTCTACCAAGTTATTCTCAA<br>CCTGGCAACGCTGCTCCCCTTTGTGTGCCAATATCAACATGCTTCTACCAAGTTATTCTCAA<br>TCTCCCTGCGGAGAGACATATCAGGGAATCAGCTCAGTCCACAGGGTGCAGAGAC<br>CCAGACAGAAGCCCATGTGAGAGCCCTGAAAGCTCATTCCTCAGCTACTTATGCCAAG<br>CTTTATGCCTACTACTTGTCCTTTCCATTGCCACCTCCAGCTACTTAATCTACCCCTCAAGT<br>AGACGGAATTAGCTGTGATTTTGTGAGTCCAATAAATAAGAGCATGCATCTCTAAAGT<br>CATTCATTTATCCTAATACTGTCTATTCTAAAGGAAGAAAATTCCAACACATAAACAAA<br>TCTGA |
| hGR08<br><br>nt: AC006518 (BAC:<br>5891-4962)<br>12p13 | >hGR08 aa<br><br>MFSPADNIFILILTGEFILGILGNG<br>YIALVNWIDWIKKKKISTVDYILTN<br>LVIARICLISVMVVNGIVIVLNPDV<br>YTKNKQQIVIFTFWTFANYLNMWIT<br>TCLNVFYFLKIASSSHPLFLWLKWK<br>IDMVVHWILLGCFAISLLVSLIAAI<br>VLSCDYRFHAIAKHKRNITEMFHVS<br>KIPYFEPLTLFNLFAIVPFIVSLIS<br>FFLLVRSLWRHTKQIKLYATGSRDP<br>STEVHVRAIKTMTSFIFFFLYIS<br>SILMTFSYLMTKYKLAVEFGEIAAI<br>LYPLGHSLILIVLNNKLRQTFVRML<br>TCRKIACMI | >hGR08 nt<br>ATGTTCAGTCCTGCCAGATAACATCTTTATAATCCTAATAACTGGAGAATTCATACT<br>AGGAATATTGGGAATGGATACATTGCACTAGTCACTGATTGACTGGATTAAGA<br>AGAAAAGATTTCCACAGTTGACTACATCCTTACCAATTTAGTTATATCGCCAGAATT<br>TGTTTGATCAGTGAATGTTGTAAATGCATTGTAAATGGATGCATTTTACCTTCTGGACATTTGCCAACT<br>TTATAATAAAACAGATGCCTTCATTTACCTTCTGGACATTTGCCAACT<br>AGTTCCTCATCCACTCTTTCTCTGGCTGAAGTGGAAATTGATATGGTGGTGCA<br>CTGATCCTGCTGGGATGCTTTGCCATTCCTTGTTGGTCAGCCTTATAGCAGCAA<br>TAGTACTGAGTTGTGATTATAGGTTTCATGCAATAAATACCATACTTTGAACCTGACTCTCTTAA<br>CCTGTTTGCAATGTCCATGTGAGTAAATACCATACTTTGCACTGATATCATTTTCCTTTAGTAA<br>GATCTTTATGGAGACATACCAAGCAATAAAACTCTATGCTACCGGCAGTAGAGAC<br>TTTTTCCTATACTATATTCTTCTTATTTGATGACTTCTATTTGATGACCTTAGCTATCTTATGACAA<br>AATACAAGTTAGCTGTGGAGTTGGAGATTGCAGCAATTCTACCCCTTGGGT<br>CACTCACTTATTTAATGTTTTAAATAATATAAACTGAGGCAGACATTTGTCAGAAT<br>GCTGACATGTAGAAAAATTGCCTGACGATATGA |

FIG. 10

| | | |
|---|---|---|
| hGR09<br><br>nt: AC006518 (BAC; nt 8986-8048)<br>GSS: B91063<br>12p13 | >hGR09 aa<br><br>MPSAIEAIYILIAGELTIGIWGNG<br>FIVLVNCIDWLKRRDISLIDIILIS<br>LAISRICLLCVISLDGFFMLLFPGT<br>YGNSVLVSIVNVWTFANNSSLWFT<br>SCLSIFYLLKIANISHPFFFWLKLR<br>INKVMLAILLGSFLISLIISVPKND<br>DMWYHLFKVSHEENITWKFKVSKIP<br>GTFKQLTLNLGVMVPFILCLISFFL<br>LLFSLVRHTKQIRLHATGFRDPSTE<br>AHMRAIKAVIIFLLLLIVYPVFLV<br>MTSSALIPQGKLVLMIGDIVTVIFP<br>SSHSFILIMGNSKLREAFLKMLRFV<br>KCFLRRRKPFVP | >hGR09 nt<br><br>ATGCCAAGTGCAATAGAGGCAATATATATATATTTAATTGCTGTGAATTGACCAT<br>AGGGATTGGGGAAATGATGATTCATTGACATGCATTGACTGACTGGCTCAAAA<br>GAAGAGATATTCCTTGATTGACATCATCCTAGTAGTTAACTGCATTGACTGGCTCCAGAATC<br>TGTCTGCTGTGTGTAATATCATTAGATGGCTTCTTTATGCTGCTCTTTCCAGGTAC<br>ATATGGCAATAGCGTGCTAGTAGCATTGTGAATGTGTGCTGGACATTGCAATA<br>ATTCAAGTCTCTGGTTACTTTCTTGCCTGCTAGTATCTTCATTTACTCAAGATAGCC<br>AATATATCGCACCCATTTTCTTCTGGCTGAAGCTCAACAAGTCATGCT<br>TGCGATTCTTCTGGGGTCCTTCACCTTTCAAAGTCAGTCAGTTGTCCAAAGAATG<br>ATGATATGTGGTATCACCTTTCCAGTGTACTTTCAAACAGTTAACCCTGAACCTGGGGT<br>TTCAAAGTGAGTAAAATTCCAGTACTTTCAAACAGTTAACCCTGAACCTGGGGT<br>GATGGTTCCCTTATCCTTGCCTGACTCGCATGCTACAGGGTTCAGAGACCCAGTACA<br>TTAGACACACCAAGCAGATTCGACTGCATGCTACAGGGTTCAGAGACCCAGTACA<br>GAGGCCCACATGAGGGCCATAAAGGCAGTGATCATCTTCTGCTCCTCCATCGT<br>GTACTACCCAGTCTTTCTTGTTATGACCCTCTGATCCTGAATCGTCATTCATTC<br>TAGTGTTGATGATTGTGACATAGTCAAGTGTGAGGGAAGCTTTCTGAAGATGTTAAGATT<br>ATTCTAATTATGGGAAATAGCAAGTTGAGGGAAGCTTTCTGAAGATGTTAAGATT<br>TGTGAAGTGTTTCCTTAGAGAAGAAGCCTTTTGTTCCATAG |
| hGR10<br><br>nt: AC006518 (BAC; nt 25180-24257)<br>12p13 | >hGR10 aa<br><br>MLRVVEGIFIFVVVSESVFGVLGNG<br>FIGLVNCIDCAKNKLSTIGFILTGL<br>AISRIFLIWIIITDGFIQIFSPNIY<br>ASGNLIEYISYFWVIGNQSSMWFAT<br>SLSIFYFLKIANFSNYIFLWLKSRT<br>NMVLPFMIVFLLISSLLNFAYIAKI<br>LNDYKTKNDTVWDLNMYKSEYFIKQ<br>ILLNLGVIFFFTLSLITCIFLIISL<br>WRHNRQMQSNVTGLRDSNTEAHVKA<br>MKVLISFIILFILYFIGMAIEISCF<br>TVRENKLLLMFGMTTAIYPWGHSF<br>ILILGNSKLKQASLRVLQQLKCCEK<br>RKNLRVT | >hGR10 nt<br><br>ATGCTACGTGTAGTGGAAGGCATCTTCATTTTGTTGTAGTAGTGAGTCAGTGTT<br>TGGGGTTTTTGGGAATGGAATGGATTGATTATTGGACTTGTAAACTGCATTGACTGACTGGCCAAGA<br>ATAAGTTATCTACGATTGCTTTATTCTCACCGGCTTAGCTATTCAAGAATTTT<br>CTGATATGGATAATAATTACAGATGGATTATACAGATATTCTCCAAATATATA<br>TGCCTCCGGTAACCTAATTGAATATTAGTTACTTTTGGGTAATTGGTAATCAAT<br>CAAGTATGTGGTTTGCCACCAGCTCAGCATCTTCTATTTCCTGAAGATAGCAAT<br>TTTTCCAACTACATATTCTCTGGTTGAAGAGCAGAACAAATATGGTTCTTCCCTT<br>CATGATGTATTCTTACTTATTCATCGTTACTTAATTTGCATACATTGCGAAGA<br>TTCTAATGATACTTTATTAAAACGAAGAATTTGCTAAATCTGGGAGTCATTCTTCTTTAC<br>AGTGAATACTTTATTAAAACGAAGAATTTGCTAAATCTGGGAGTCAACATGTATAAA<br>ACTATCCCTAATTACACATGTATTTTTTAATCATTCCCTTGGAGACACAACAGC<br>AGATGCAATGAAATGGACGATTGAGAGACTCCCTCTTATCTGTATTTATAGGAT<br>GCAATGAAAGTTTGATATCATGTTTACTGTGCGAGAAAAACAAACTGCTGCTATGTTTG<br>GGCCATAGAAATATCATGTTTACTGTGCGAGAAAAACAAACTGCTGCTATGTTTG<br>AATGACAACCACAGCCATCTATCCCTGGGGTCACTCATTCTCTTAATTCTAGGA<br>AACAGCAAGCTAAAGACAAGCCCTCTTTGAGGGTACTGCAGCAATTGAAGTGCTGTGA<br>GAAAAGGAAAAATCTCAGAGTCACATAG |

FIG. 1P

| | |
|---|---|
| hGR11<br>pseudogene<br><br>nt: AC006518 (BAC; nt 34325-30167)<br>12p13<br><br>notional cds derived from aligning reading frames split by 4 kb interval | >hGR11 aa<br>MANMLKNMLTMISAIDFIMGIQRSR<br>VMVLVHCIDWIRRWKLSLIDFILTC<br>WAISRIFXXXXXXXXXXXXXXXXXXX<br>XXXXXXXXXXXXXXXNHLCT*FATCL<br>AVFYFLKIVNFSYLFYFWLKWRINK<br>VAFILPLVSAFSVYQLSEDVHF*CL<br>LVSCPKKYERHMTGLLNVSNNKNVN<br>NIIFFIGSLSSFSISSIFFLLLL<br>SS*RHMKHIRFNFRDCRTPVYGPIS<br>EPRKRFSFFVLLYKNLPFS |
| hGR12<br>pseudogene<br><br>nt: AC006518 (BAC; nt 94792-93845)<br>12p13 | >hGR12 aa<br>MSSIWETLFIRILVV*FIMGTVGN*<br>FIVLVNIID*IRN*KVSLIDFILNC<br>LAISRICFL*ITILATSFNIGYEKM<br>PDSKNLAVSFDILWTGSSYFCLSCT<br>TCLSVFYFLKVANFSNPIFLWMKWK<br>IHKVLLFIVLEATISFCTTSILKEI<br>IINSLI*ERVTIKGNLTFNYMDTMH<br>DFTSLFLLQMMFILPFVETLASILL<br>LILSLWSHTRQMKLHGIYSRDPSTE<br>AHVKPIKAIISFLLLFIVHYFISII<br>LTLACPLLDFVAARTFSSVLVFFHP<br>SGHSFLLILRDSKLKQASLCVLKKM<br>KYAKKDIISHFYKHA | >hGR12 nt<br>ATGTCAAGCATTTGGGAGACACTGTTTATAAGAATTCTTGTAGTGTAATTCATAAT<br>GGGGACTGTGGGAAATTGATTCATTGATTGTAATCATTGACTGAATCAGGA<br>ACTGAAAGGTCTCCCTGATGATTTGATTCTCAACTGCTTGGCCATCTCCAGGATA<br>TGTTTCCTGTAGATAACAATTTAGCTACCTCTTCAATATAGGCTATGAGAAAAT<br>GCCTGATTCTAAGAATCTTGCAGTAAGTTTGACATTCTCTGGACATTCCTCAGCT<br>ATTTCTGCCTGTCCTGTACCACTTTCCTCCAATCCCATTTCCTCTGATGAAATGCTCTTATTCCAAGGTAGCC<br>AACTTCTCAATCCCATTTCCTCTGATGAAATGAAAATTCACAAGGTGCTTCT<br>CTTTATTGTACTAGAGGCAACGATCTCTTCTGCACAATAAAAGGCAACTGACATTT<br>TAATAATTAATAGTTAATCTAAGAACGGTAACAATAAAAGGCAACTGACATTT<br>AATTATATGATACCATGCATGATTTCACTTCCTCGTTCCTTCCTTCAGATGATGTT<br>CATCCTTCCTTTGTGGAAACACTGGCTTCCATTCTTCCATTTATTCCAGGATCCCAGCACA<br>GGAGCCACACCAGGCAGATGAAGCTACATGGTATTATTCCAGGATCCCAGCACA<br>GAAGCCCATGTAAAACCTATAAAGCTATAATTCATTCTACTCCTCTTTATTGT<br>GCATTATTTCATCAGTATCATCATCAACATTGGCCTGCCCTCCTTCTAGACTTCGTTG<br>CGGCAAGGACTTTAGTAGTGTGCTGGTATTTCCATCCATCTGGCCATTCATTT<br>CTTCTAATTTTACGGGACAGCAAACTGAAGCAAGCTTCTCTCGTGTCCTGAAGAA<br>GATGAAGTATGCCAAAAGGACATAATCTCTCATTTTTATAAACATGCCTGA |

FIG. 1Q

| hGR13<br><br>nt: AC006518 (BAC; nt 108209-107298)<br><br>12p13 | >hGR13 aa<br><br>MESALPSIFTLVIIAEFIIGNLSNG<br>FIVLINCIDWVSKRELSSVDKLLII<br>LAISRIGLIWEILVSWFLALHYLAI<br>FVSGTGLRIMIFSWIVSNHFNLWLA<br>TIFSIFYLLKIASFSSPAFLYLKWR<br>VNKVILMLLGTLVELFLNLIQINM<br>HIKDWLDRYERNTTWNFSMSDFETF<br>SVSVKFTMFSLTPFTVAFISFLL<br>LIFSLQKHLQKMQLNYKGHRDPRTK<br>VHTNALKIVISFLLFYASFFLCVLI<br>ATGAGTGACTTTGAAACATTTCAGTGTCGTCAAATTCAGTGTCGTCAAATTCACTATGACTATGTTCAG<br>SWISELYQNTVIYMLCETIGVFSPS<br>SHSFLLILGNAKLRQAFLLVAAKVW | >hGR13 nt<br><br>ATGGAAAGTGCCCTGCCGAGTATCTTCACTCTTGTAATAATTGCAGAATTCATAAT<br>TGGGAATTTGAGCAATGCAATGATTTATAGTACTGATCAACTGCATTGACTGGGTCAGTA<br>AAAGAGAGCTGTCCTCAGTGACAATATTAGTACGTCCTCATTATCTTGGCAATCTCCAGAATT<br>GGGCTGATCTGGGAAATATTAGTAAGTTGCTTTTAGCTCTGCATTATCTAGCCAT<br>ATTTGTGTCTGGAACAGGATTAAGAATTATGATTTTAGCTGATAGTTTCTAATC<br>ACTTCAATCTCGGCTTGCTACAATCTTCAGCATCTTTATTGCTCAAAATAGCG<br>AGTTTCTCTAGCCCTGCTTTTCTCTATTTGAAGTGGAGAGTAAACAAAGTGATTCT<br>GATGATACTGCTAGGAACCTTGGTCTTCAGTGTCTGGACCGATATGAAAGAAACACAACTTGGAATTTCAGT<br>TGCATATAAAAGACTGGCTGGACCGATATGAAAGAAACACAACTGGAATTTCAGT<br>ATGAGTGACTTTGAAACATTTCAGTGTCGTCAAATTCACTATGACTATGTTCAG<br>TCTAACACCATTACTGTGGCCTTCATCTCTTTCCCTGTTAATTTCTCCCTGC<br>AGAAACATCTCCAGAAATGCAACTCAATTACAAAGGACACAGAGACCCCAGGACC<br>AAGGTCCATACAAATGCCTTGAAAATTGTGATCTCATTCCTTTATTCTATGCTAG<br>TTTCTTTCTATGTGTTCTCATATCATGGATTTCTGAGCTGTATCAGAACACAGTGA<br>TCTACACATGCTTTGTGAGACGTTAAGCTAAGCTAAGGT<br>ATGGGCTAAACGATGA |<br>|---|---|---|<br>| hGR14<br><br>nt: AC006518 (BAC nt 138118-137165)<br><br>12p13 | >hGR14 aa<br><br>MGGVIKSIFTFVLIVEFIIGNLGNS<br>FIALVNCIDWVKGRKISSVDRILTA<br>LAISRISLVWLIFGSWCVSVFFPAL<br>FATEKMFRMLTNIWTVINHFSVWLA<br>TGLGTFYFLKIANFSNSIFLYLKWR<br>VKKVVLVLLLVTSVFELFNIALINI<br>HINASINGYRRNKTCSSDSSNFTRF<br>SSLIVLTSTVEFIPFTLSLAMFLL<br>LIFSMWKHRKKMQHTVKISGDASTK<br>AHRGVKSVITFFLLYAIFSLSFFIS<br>VWTSERLEENLILSQVMGMAYPSC<br>HSCVLILGNKKLRQASLSVLLWLRY<br>MFKDGEPSGHKEFRESS | >hGR14 nt<br><br>ATGGGTGGTGTCATAAAGAGCATATTTACATTCGTTTTAATTGTGGAATTTATAAT<br>TGGAAATTTAGGAATAGTTTCATAGCACTGTGAACTGTATTGACTGGGTCAAGG<br>GAAGAAAGATCTTCGGTTGATCGGATCCTCACTGCTTGCAATCTCTCGAATT<br>AGCCTGGTTTGGTTAATATTCGGAAGCTGGCTGGTGTCTGTGTTTCCCAGCTTT<br>ATTTGCCACTGCAAAAAATGTTCAGAATGCTTACTACATCTGACAGTGATCAATC<br>ATTTAGTGTCTGGTTAGCTACAGGCCTCGGTACTTTTATTTCTCAAGATAGCC<br>AATTTTCTAACTCTATTTTCTCACTCTAACCTAAAGTGGAGGGTTAAAAGGTGGTTTT<br>GGTGCTGCTTCTGTGACTTCGGTCTTCTGTTTAAATATTGCACTGATAAACA<br>TCCATATAAATGCCAGTATCAATGATACAGAAGAAACAAGACTTGCAGTTCTGAT<br>TCAAGTAACTTACACGATTTCCAGTCTATTGTCCCTGGCAATGTTCTCCTCATCTTCCATGT<br>TTCATACCCTTACTTGTCCGTCAGCACACTGTCAAAATATCCGGAGACGCCAGCACC<br>GGAAACATCGCAAGAGATGCAGTTAAAGTGTGATCACTTCTGAGCCTTATGCCATTT<br>AAGCCCACAGAGAGGAGTTCATAATCAGTTTGGACCTCGAAAGTTGGAGGAAAATCAA<br>CTCTCGTCTTTTTCCAGTGATGGGAAAGCTGAGACAGGCCCTCTATCCTCGTGTCAGTGCTACTGTTCTG<br>TTATTCTTGGAAACAAGAGCTGAGACAGGCCCTCAGGTCACAAAGATGTTCAAAGATGTTCAAAGATTTCAAAGAATTTAGAGAATCATCTT<br>GTACATGTTCAAAGATGGGGAGCCCTCAGGTCACAAAGATGTTCACAAAGAATTAGAGAATCATCTT<br>GA |

| hGR15 | >hGR15 aa | >hGR15 nt |
|---|---|---|
| likely pseudogene<br><br>nt: AC006518 (BAC nt 164263-16331)<br>12p13<br>HTGS: AC006513 | MITFLPIIFSILVVTFVLGNFANG<br>FIVLVNSIEWKRQKISFADQILTA<br>LAVSRVGLLWVILLHWYATVLNPGS<br>YSLGVRITTINAWVTNHFSIWVAT<br>SLSIFYFLKIANFSNFIFLHLKRRI<br>KSVIPVILLGSLLFLVCHLVVVMD<br>ESMWTKEYEGNVSWEIKLSDPTHLS<br>DMTVTTLANLIPFTLSLLSFLLLIC<br>SLCKHLKRMQFHGKGSPDSNTKVHI<br>KALQTVTSFLLLFAVYFLSLITSIW<br>NFRRRL*NEPVLMLSQTTAIIYPSF<br>HSFILIWGSKKLKQTFLLILCQIKC | ATGATAACTTTTCTACCCATCATTTTTCATTCTAGTAGTGGTTACATTTGTTCT<br>TGGGAATTTGCTAATGCTTCATGATGTTGTTAATTCCATTGAGTGGGTCAAGA<br>GACAAAAGATCTCCTTTGCTGACCAAATTCTCACTGCTCTGGCAGTCTCCAGAGTT<br>GGTTTGCTCTGGGTAATATTATTACATTGGTATGCAACTGTTTGAATCCAGTTC<br>ATATAGTTAGGAGTAAGAATTACTACTATTAATGCCTGGGCTGTAACCAACCATT<br>TCAGCATCTGGGTTGCTACTAGCCTCAGCATATTTATTTCCTCAAGATTGCATTG<br>TTTCCAACTTATTGGGGTCTCTTTGTTATTTTTGGTTTGTCATCTTGTTGGTAAACATGG<br>GATACTATTGGGGTCTCTTTGTTATTTTTGGTTGTCATCTTGTTGTGGTAAACATGG<br>ATGAGAGTATGTGGACAAAAGAATATGAAGGAAACGTGAGTTGGGAGATCAAATTG<br>AGTGATCCGACGCACCTTTCAGATACTACTTTCTGCTTAACCACGTTGCAAACTTAATACC<br>CTTTACTCTGTCCCTGTTATCTTTTCTGCTTAATCGTCTTCTTGTGTAAACATC<br>TCAAGAAGATGCAGTTCCATGGCAAAGGATCTCCAGATTCCAACACCAAGGTCCAC<br>ATAAAAGCTTGCAAACGGTGACCTCCTCTGTTATTGCTGTTACTTTCT<br>GTCCCCTAATCACATCGATTTGGAATTTAGGAGGAGGCTGTAGAACGAACCTGTCC<br>TCATGCTCAGCCAAACTGCAATTATATACCCTTCATTCATCCTA<br>ATTTGGGAAGCAGAAGCTGAAACAGACCTTTCTTTGATTTTGTGTCAGATTAA<br>GTGCTGA |

| hGR16 | >hGR16 aa | >hGR16 nt |
|---|---|---|
| HTGS: AC004838 (nt 64142-63267) | MIPIQLTVFFMIIYVLESLTIIVQS<br>SLIVAVLGREWLQVRRLMPVDMLI<br>SLGISRFCLQWASMLNNFCSYFNLN<br>YVLCNLTITWEFFNILTFWLNSLLT<br>VFYCIKVSSFTHHIFLMLRWRILRL<br>FPWILLGSLMITCVTIIPSAIGNYI<br>QIQLLTMEHLPRNSTVTDKLENFHQ<br>YQFQAHTVALVIPEILFLASTIFLM<br>ASLTKQIQHHSTGHCNPSMKARFTA<br>LRSLAVLFIVFTSYFLTLITIIGT<br>LFDKRCWLWVWEAFVYAFILMHSTS<br>LMLSSPTLKRILKGKC | ATGATACCCATCCAACTCACTGTCTTCTTCATGATCATCTATGTGCTTGAGTCCTT<br>GACAATTATTGTGCAGAGCAGCCTGATTGTTGCAGTGCTGGGAGAATGGCTGC<br>AAGTCAGAAGGCTGATGCCTGTGGACATGCTCATCAGCCTGGGCATCTCTCGC<br>TTCTGTCTACAGTGGGCATCAATGCTGAACAATTTTGCTCCTATTTAATTTGAA<br>TTATGTACTTTGCAACTTAACAATCACCTGGGAATTTTTAATATCCTTACATTCT<br>GGTTAAACAGCTTTCTCGGCTGAGTGTTCCATCAAGGTCTCTCTTTTCACCCAT<br>CACATCTTTCTCGATGATTACTTGTGTAACAATCATCCCTTCAGCTATTGGAATTACA<br>GGGTTCTTCTGATGATTACTTGTGTAACAATCATCCCTTCAGCTATTGGAATTACA<br>TTCAAATTCAGTTACTGCACCATGAGTATCAGTTCCAGGCTATCAGTTGCATTGGTTAT<br>AAACTTGAAATTTCAAATTCAGAAAATTCAGTTCCAGGCATCTTCCATGGCATCACTGACCAAGC<br>TCCTTTCATCCTGTTCCGGCCTCCACCATCTTTCCATGGCATCACTGACCAAGC<br>AGATACAACATCATAGCACTGGTACTGCTCAATCCAAGCATGAAAGCGCGCTTCACT<br>GCCCTGAGGTCCCTGCCGTCCCTGCCGTCCTGTTACCTCTTATTATTGATAAGCATGAAAGCGCGCTTCACT<br>ACTCATCACCATTATAGTACTCTATTTCATCTAATGCATTCCACTTGGTTATGGGTCTGG<br>AAGCTTTGCTATGCTTTTCATCTTATTGATAAGCATTCCACTTGGTTATGGGTCTGG<br>CCTACGTTGAAAAGGATTCTAAAGGGAAAGTGCTAG |

| | | |
|---|---|---|
| hGR17<br>EST: AL037695 | >hGR17 aa<br>GILSILVVFAFVLGNVANGFIALVN<br>VNDWVKTQKISSTDQIVTALAFSRI<br>GLLXIILLHWYATVFNSALYSLEVR<br>IVPSNVSAIINHFSIWLATSLSIFY<br>LFKIANFSNFIFLHLKKRIKSVLLV<br>ILLGSLVFLICNLAVVTMG | >hGR17 nt<br>GGGCATTTTATCAATTCTGGTAGTGTTTGCATTTGTTCTTGGAAATGTTGCCAATG<br>GCTTCATAGCTCTAGTTAATGTCAATGACTGGGTTAAGACACAAAAGATCTCCTCA<br>ACTGACCAAATTGTCACTGCTCTGGCATTCTCCAGAATTGGTTACTTTGATCATA<br>TTATTACATTGGTATGCAACTGTGTTAATTCAGCTTTATATAGTTTAGAAGTAAG<br>AATTGTCCTTCAGCTGTCTCGGCAATATGTCTTGTTCAAGATGCCAATTCTCCAATTTATTTT<br>CGAGCCTCAGCATATTTATTTGTTCAAGATTGCCAATTCTCCAATTTATTTTT<br>CTCCACCTAAAGAGAGAATTAAGAGTGTTCTTCTTGTGATACTGTTGGGTCCTT<br>GGTATTTTGATTTGTAATCTGCTGTGTGTGGTAACCATGGATGACAGGTGTGTGGAC<br>AAAAGAATTGAAGAAATGTGACTTGGGAAGGATCGAATTGAGGAATGCAATACA<br>CCTTTCAAACATGACTATAACCCAACCATGCTAGCAAACTTCACACTGTA |
| hGR18<br>EST: N52978, H81901 | >hGR18 aa<br>MFVGINIFFLVVATRGLVLGMLGNG<br>LIGLVNCIEWAKSWKVSSADFILTS<br>LAIVRIIRLYLILFDSFIMVLSPHL<br>YTIRKLVKLFTI | >hGR18 nt<br>TCCTGAAATTGGCTATGCCCCTCTGAAATTGTGATGAAAACCATAGATTAGAAAG<br>CATCATAAATGCATGCCCATCTGCAACTGTTTGACNTATAAAGCTGTCAGTGAAGT<br>AGAATATCGGAACAAGAGACTTGTCTTAGGAATGCTGGGAAACGGCTCATTGACT<br>GTGTGGCAACAAGAGACTTGTCTTAGGAATGCTGGGAAACGGCTCATTGACT<br>GGTAAACTGCATTGGCTATATGTCCCCTCATCTATATACCATCGTAAACTAGTAAACTGTT<br>TCACCAGCTTGGCTATAGTCAGAATCATTGACTGTATTTAATACTATTTGATTCA<br>TTATAATGGTATTGTCCCCTCATCTATATACCATCGTAAACTAGTAAACTGTT<br>TACTATT |
| hGR19<br>GSS:B17827 | >hGR19 aa<br>VTTLANLIPFTLSLICFLLLICSLC<br>KHLKKMRLHSKGSQDPSTKVHIKAL<br>QTVTSFLMLFAIYFLCIITSTWNLR<br>TQQSKLVLLCQTVAIMYPSFHSFI<br>LIMGSRKLKQTFLSVLWQMTC | >hGR19 nt<br>CTGTAACTACTCCAGCCAAACCTCATACCCTTTACTCTGAGCCTAATATGTTTCTG<br>CTGTTAATCTGTTCCTTTGTAAACATCTCAAGAAGATGCGGCTCCATAGCAAGG<br>ATCCAAGATCCCAGCACCAAGGTCCATTAGCTTTGCAAACTGTGACCTCCT<br>TCCTCATGTTATTTGCCATTTACTTCTGTGTATAATCACATCAACTTGGAATCTT<br>AGGACACAGCAGCAAACTTGTACTCCCTGCTTTGCCAAACTGTTGCAATCATGTA<br>TCCTTCATTCCACCACTCATTCATCCTGATTATGGGAAGTAAGGAAGCTAAAACAGACCT<br>TTCTTCAGTTTGTGGCAGATGACATGCTGAGTGAAGAAGATGAGAAACCCTCAACT<br>CCATAGATCACAAGGGAGCATCGTGGGTCTTCTAGCAGAAACAACCAACTGATGGT<br>GTCTGGAACAATTTATAT |
| hGR20<br>GSS: AQ164951 (nt<br>given in sense<br>orientation) | >hGR20 aa<br>HLXRKAKSVVLIVIVIGSLFFLVCQL<br>VMKNTYINVMTEECEGNVTWKIKLR<br>NAMHLSNLTVAMLANLIPFTLVIS<br>FLLIYSLCKHLKKMQLHGKGSQDP<br>STKIHIKALQTVTSFLVLLAIYFLC<br>LIIS | >hGR20 nt<br>TTCATCACTTANAAAGGAAGGCTAAGAGTGTAGTTCGTGATAGTGTGGGTCT<br>TTGTTCTTTTGGTTTGTCAACTTGTGATGAAAACACGTATATAAATGTGGAC<br>AGAAGATTGAAGGAACGTAACTTGGAAGATCAAACTGAGGAATGCAATGCACC<br>TTTCCAACTTGACTGTAGCCATGCTAGCAACTCTCGTGTAACATTCACTCGACCGTG<br>ATATCTTTCTGCTGTTAATCTCAAGATCCAAGACTGTAACATCCACATAAGCTCTGCAAA<br>CCATGGCAAAGATCCAAGATCTCAAGACTGTAACATCCACATAAAGCTCTGCAAA<br>CTGTGACCTCCCTCCCTGTATTACTTGCCATTTACTTTCTGTGTCTAATCATATCC<br>TTTTG |

FIG. IT

| | | |
|---|---|---|
| hGR21<br>GSS:AQ103952 | >hGR21 aa<br>MITFLPIIFSILIVIFVIGKFANG<br>FIALVNSIEWVKRQKISFVDQILTA<br>LXGLRVWLLWVLLH | >hGR21 nt<br>TTATCCATTAGACATGCCATGTGTGATTCTGACTTGACACTGGTCACAGCAATTAAA<br>AGTAAAAGATGTCACAGCACATACACAACCAGTGCATATAGAATTAAGTC<br>AGGATATTCAAGCAATCACACACCAGTGATATTACACCAGCATTTTAAAAATTCTT<br>TNTGTCTGTTCAGACATGATGATATCTGCCCATCATTTTTCCATTCTAATAGT<br>GGTTATATTTGTTATTGGGAAATTGCTAATGGCTTCATAGCATTGGTAAATTCCA<br>TTGAGTGGGTCAAGAGAGACAAAAAGATCTCCTTTGTTGACCAAATTCTCACTGCTCTG<br>NGCGGTCTCAGAGTNTGGTTGCTCTGGGGTGGTATTACTACACATTGAG |
| hGR22<br>GSS: AQ709702 | >hGR22 aa<br>MATESDTNLLILAIAEFIISMLGNV<br>FIGLVNCSEXIKNXKVFSADFILTC<br>LAISHNGQLLVILFDSFLVGLASHL<br>YTTYRLXKNCIMLWT | >hGR22 nt<br>TATAGGGACNGTGATGCTTCGTACACTCTCCAAGAAGAAACACTCCGTGAGGTATG<br>TGAGACTGCATNCCTTAGTAGATCNTNTTGGGATATATATTCATATATAGAAAAAN<br>AGGCAAAGACTTNCTTAAGTATATGAGACTCTATCCAACAGCAGAGGTTCTGATC<br>AAGACTGGAAGTGCAATANAAGCAATGAAGATAAGTATCAGATATGAATGCTCTTC<br>TGCAATGGTCTGATTGTNACATTATTAATGATACANAGTATTAAAAACTTGGATTT<br>TNTTGTCTCTGGAGATGGCCACCATGATCAGCAATCGGACACAAATCTTCTGATTCTGGCAATA<br>GCAGAATTCATCATCAGCAATGCATNAAGGTCTTCTCAGCTGACTCTGTTGATTCATTTCTAGTGGGA<br>GAAGGATCAGAACCANAAGGTCTTCTCAGCTGACTCTGTTGATTCATTTCTAGTGGGA<br>CTATCCTCCACAATGGACAACTGTTGGTGATACTGTTGATTCATTTCTAGTGGGA<br>CTTGCTTCACATCTATATCACTTGACACACTGCTTCGCACGTGCTAGCATATTCTATTCTTA<br>GACATGACTAATCACTTGACACACTCCCTTGTCTCTGCTGAAGTGGGAT<br>GATAGCCACTTCNCACTCCCTTGTCTCTGCTGAAGTGGGAT |
| hGR23<br>GSS: AQ590563 | >hGR23 aa<br>VAFVLGNVANGFIALVNVIDXVNTR<br>KISSAEQILTALVVSRIGXTLXHSI<br>P*DATRC*SALYRXEVRIVASN | >hGR23 nt<br>AGGGTTGAGTCGTGCTTATCTTCACTTAACCTAGTATANAANTACAGCATATAGCA<br>AGGAGAGAATGTATATGAAGAGGAGTGAATTTGAGTCTGTTGAGATAATGACCT<br>TTTCTATTCTATAAAGACAGTTTGAATTCATCTATTAGCATATGCTGGTGCTTG<br>CCTGTTGACACTAGTCACTGAATTAAAGGCAGAAAATGTTATTGCACATTAGTA<br>ATCAAGTGTTCATCGAAGTTAACATCTGAATTGTAAAGGACTCAGAACAAGTGTTA<br>CTAAGCCTGCATTTTTATCTGGAGTTGCATTGTTCTTGTTCTTGTTNTCTGCTCATTGT<br>ATCAATTCGGTAGAGTTGCATTGNGTCTCCAGAATTGGTAATGTGAAATCCACGAAAGATCTCCTCGNTCTATAGTATGCCAAA<br>TCTAGTAAATGTCATTGACTGNGTCTCCAGAATTGTTNNTACTCTGNGTCATAGTATTCCT<br>TGAGATGCAACTAGATGTTAATCTGCTCTATATAGGNTAGAAGTAAGAATTGTTGC<br>TTCTAATGCCTGAGCTCGTCGTACGAACCATT |

FIG. 1U

| hGR24 | >hGR24 aa | >hGR24 nt |
|---|---|---|
| GSS: AQ719085 | MATELDKIFLIMAVAEFIISMLGNV FIGLVNCSEGITNQNVVLADFILTC MASLTIGQLVVILFDYFL | AGTCACNNNATGAAGACTGGGACCTCGTATTCACCNCTCTCTAGAGAAAAGAAAA CACTCTCGAGAAGGTATGTGAGACTGCAGAGCTTAGACCTTAGTAGATCTTGTGGGATTAAGA ACAGAATTATGTCAAAATAGGCCAAGACTTCCTTAAGTATATGAGACTCTATCCA ACAGCAGAAGGTTCTGATCAAGACTGGAGAGGCAATAAAAGCAATGAAGATAAGTA TCAGATATGAATGCTCTTCTGCAATGTGTCTCTGCAATGTGATTGATTATTAATGATACAAA GTATTAAAGACTTGGATTTTTCGTCTCTGGAGATGGCCACCATGCTGGGAATGTGTTCA CTTTCTGATTATGGCAGTAGCAGTAGAATTCATCATCAGCATGCTGGGAATGTCGTTCAGTTCA TTGGACTGGTCAACTGCTCTGAAGGGATCACAACCAAAATGTCGTTCTAGCTGAC TTCATACTCACCTGCATGCCTAGTCTCACAATTGGACAACTGGTGGTGATACTGTT TGATTATTCTGTGTGACTGTG |

Figure 3A:
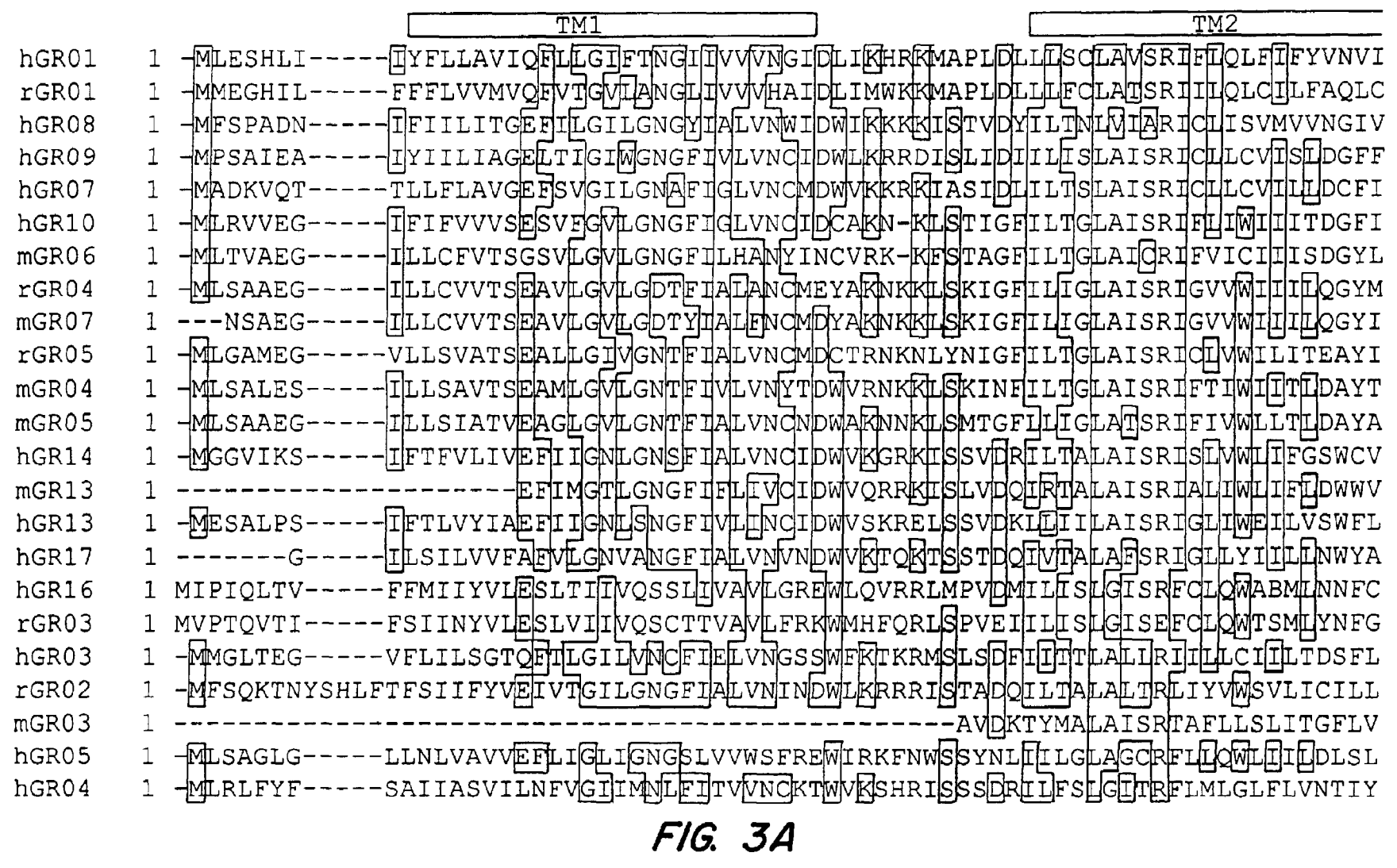

Multiple sequence alignment of GR receptors showing TM1 and TM2 transmembrane domains across:
hGR01, rGR01, hGR08, hGR09, hGR07, hGR10, mGR06, rGR04, hGR07, rGR05, mGR04, mGR05, mGR14, mGR13, hGR13, hGR17, hGR16, hGR03, rGR03, hGR02, rGR02, mGR03, hGR05, hGR04

|  |  | TM4 | | TM5 | |
|---|---|---|---|---|---|
| hGR01 | 139 | MICVFHS------KYAGFMVPYFLR------KFFSQNATIQKEDTLAIQIFSF----VAEFSVPLLIFLFAVL |
| rGR01 | 139 | ITTFIHS------RETSAILKPIFI------SLAPKNATQVG-TGHATLLSVL----VLGLTLPLFIFTVAVL |
| hGR08 | 143 | LVSLIAAIVLSCDYRFHAIAK-HKR------NITEKFHVSKIP-YFKPLITLFN----LFAIVPFIVSLISFF |
| hGR09 | 143 | IISVPK------NDDMWYHLFKVSHEE------NITWKFKVSKIPGTFKQLTLN----LGVMVPFILCLISFF |
| hGR07 | 143 | FISLPATENLNADFRFCVKAK-RKT------NLTWSCRVNKTQHASTKLFLN----LATLLPFCVCLNSFF |
| hGR10 | 141 | LNFAYI------AKILNDYKTKN------DTVWDLNMYKSEYFIKQILLN----LGVIFFETLSLITCI |
| mGR06 | 141 | SIAFPQT------VKIFNVKK------ |
| rGR04 | 142 | LLCFPQF------SKMLNNSKMYWG------NTSWLQQQ--KNVFLINQSLTN----LGIFFFIIVSLITCF |
| rGR07 | 140 | LLCFPQM------TKILQNSKMHQR------NTSWATSG-KILLLPK----------- |
| rGR05 | 142 | LFSFPVV------VKMVKDKKMLYI------NSSWQIHMKKSELIINYVFTN----GGVELLFINVIGCF |
| rGR05 | 142 | LASFPLA------VKVIKDVKIYQS------NTSWLIHLEKSELLINYVFAN----MGPISLFIVAIIACF |
| mGR05 | 142 | VISFSFV------VKVMKDGKVNHR------NRTSEMYWEKRQFTINYVFLN----IGVISLFMMTLTACF |
| hGR14 | 143 | LNIALIN------IHINASINGYRR------NKTCSSDSSNFTRFSSLIVLTS----TVFIFIPFTLSLAMFL |
| mGR13 | 128 | LNTVIIK------IFSDVCFDSVQR------NVSQIFIMYNHEQICKFLSFTN----PMFTFIPFVYH---- |
| hGR13 | 143 | LNLIQIN------MHIKDWLDRYER------NTTWNFSMSDFETFSVSVKFTM----TMFSLTPETVAFISFL |
| hGR17 | 136 | CNLAVVT------MG-------------------------------------------------- |
| hGR16 | 139 | VTIIPSA------IGNYIQIQLLTN------EHLPRNSTVTDKLENFHQYQFQ-AHTVALVIPFILFLASTI |
| rGR16 | 139 | LSIIPSV------VKYHIQMELLTL------DHLPKNSSLILRLQMFEWYFSNPFKMIGFGVPFLVFLISII |
| hGR03 | 143 | GSTASLIN------EFKLYSVFRGIEATR------NVTEHFRKKRSEYYLIHVLGT----LWYLPPLIVSLASYS |
| rGR03 | 148 | LNISSLGMYDHFSIDVYEGNMSYNLVDSTHFPRIFLFTMSSKVFLIANSSHVFLPINSLFMLIPFTVSLVAFF |
| mGR03 | 101 | MNIIVIN------KFTDRLQVNTL------QNCSTSNTLKDYGLFLFISTG----FTLTPFAVSLTMFL |
| hGR05 | 139 | LTVQIG------LTFYHFPQG------NSBIRYPFESWQYLYAFQLNS----GSYLPLVVFLVSSG |
| hGR04 | 142 | FTTCLYIT------LSQASPFPELVTTR------NNTSFNISEGILSVVSLVLS----SSLQEINVTSAS |

FIG. 3D

```
          TM7
hGR01 269 YPSGHSLLILILGNPKLKQNAKKFFLHSKCCQ--------------------------
rGR01 267 YPSIHSIVLILGNPKLKRNAKNFIVHCKCCHCTRAWTSRSPRLSDLPVPPTHPSANKTSCSEACIMPS
hGR08 277 YPLGHSLILIVLNNKLRQTFVRMLTCRKIACMI-------------------------
hGR09 274 FPSSHSFILIMGNSKIREAFLKML--REVKCFLRRKPFVP------------------
hGR07 277 YPSSHSFILILGNNKIRHASLKVI--WKVNSILKGRKFQQHKQI--------------
hGR10 269 YPWGHSFILILGNSKLKQASLRVLQQLKCCEKRNLRVT-------------------
mGR06
rGR04 270 YPCGHSIILILGNKQLKQASLKALQLQHLTCCETKRNLSVT------------------
mGR07
rGR05
mGR04
rGR04 271 YPCCHSFILILTSRKLKQDTMRALQRLKML---------------------------
mGR05 271 YPCCHSFILILSNSQLKQAFVKVLQGLKFF---------------------------
hGR14 272 YPSCHSCVLILGNKKLRQASLSVLLWLRYMFKDGEPSGHKEFRESS---------------
mGR13
hGR13 273 SPSSHSFLLILGNAKLRQAFLLVAAKVW-----------------------------
hGR17
hGR16 268 FILMHSTSLMSSPTLKRILKGKC---------------------------------
rGR03 270 LVCIHFTSLMSNPTLKKALRLQFWSPESS-----------------------------
hGR03 276 YPAGHSFILILGNSKLKQTFVNLRCESGHLKPGSKGPIFS------------------
rGR02 295 FSISHSFVLIIGNCVLIGNSKLRQATLSVLPCLRCRSKDNDTVVF--------------
mGR03 228 FPTGHSCVLIGNSKLRQASLSVILWLRYKYKHIENWGP--------------------
hGR05 264 YPSLHSLILIMGIPRVKQTCQKILWKTVCARRCWGP---------------------
hGR04 272 YSPGHSVLILITHPKLKTTAKKIILCFKK------------------------------
```

FIG. 3E

SEQUENCE LISTING

<160> NUMBER OF SEQ ID NOS: 92

<210> SEQ ID NO 1
<211> LENGTH: 335
<212> TYPE: PRT
<213> ORGANISM: Rattus sp.
<220> FEATURE:
<223> OTHER INFORMATION: rat GR01, sF01

<400> SEQUENCE: 1

Met Met Glu Gly His Ile Leu Phe Phe Leu Val Val Met Val Gln
 1               5                  10                  15

Phe Val Thr Gly Val Leu Ala Asn Gly Leu Ile Val Val Val His Ala
                20                  25                  30

Ile Asp Leu Ile Met Trp Lys Lys Met Ala Pro Leu Asp Leu Leu Leu
                35                  40                  45

Phe Cys Leu Ala Thr Ser Arg Ile Ile Leu Gln Leu Cys Ile Leu Phe
             50                  55                  60

Ala Gln Leu Cys Leu Phe Ser Leu Val Arg His Thr Leu Phe Glu Asp
 65                  70                  75                  80

Asn Ile Thr Phe Val Phe Ile Ile Asn Glu Leu Ser Leu Trp Phe Ala
                    85                  90                  95

Thr Trp Leu Gly Val Phe Tyr Cys Ala Lys Ile Ala Thr Ile Pro His
                    100                 105                 110

Pro Leu Phe Leu Trp Leu Lys Met Arg Ile Ser Arg Leu Val Pro Trp
                    115                 120                 125

Leu Ile Leu Gly Ser Val Leu Tyr Val Ile Ile Thr Thr Phe Ile His
130                 135                 140

Ser Arg Glu Thr Ser Ala Ile Leu Lys Pro Ile Phe Ile Ser Leu Phe
145                 150                 155                 160

Pro Lys Asn Ala Thr Gln Val Gly Thr Gly His Ala Thr Leu Leu Ser
                    165                 170                 175

Val Leu Val Leu Gly Leu Thr Leu Pro Leu Phe Ile Phe Thr Val Ala
                    180                 185                 190

Val Leu Leu Leu Ile Tyr Ser Leu Trp Asn Tyr Ser Arg Gln Met Arg
                    195                 200                 205

Thr Met Val Gly Thr Arg Glu Tyr Ser Gly His Ala His Ile Ser Ala
                    210                 215                 220

Met Leu Ser Ile Leu Ser Phe Leu Ile Leu Tyr Leu Ser His Tyr Met
225                 230                 235                 240

Val Ala Val Leu Ile Ser Thr Gln Val Leu Tyr Leu Gly Ser Arg Thr
                    245                 250                 255

Phe Val Phe Cys Leu Leu Val Ile Gly Met Tyr Pro Ser Ile His Ser
                    260                 265                 270

Ile Val Leu Ile Leu Gly Asn Pro Lys Leu Lys Arg Asn Ala Lys Met
                    275                 280                 285

Phe Ile Val His Cys Lys Cys Cys His Cys Thr Arg Ala Trp Val Thr
                    290                 295                 300

Ser Arg Ser Pro Arg Leu Ser Asp Leu Pro Val Pro Thr His Pro
305                 310                 315                 320

Ser Ala Asn Lys Thr Ser Cys Ser Glu Ala Cys Ile Met Pro Ser
                    325                 330                 335

<210> SEQ ID NO 2

```
<211> LENGTH: 1331
<212> TYPE: DNA
<213> ORGANISM: Rattus sp.
<220> FEATURE:
<223> OTHER INFORMATION: rat GR01, Sf01

<400> SEQUENCE: 2
caggaatcat aaatggctga aactgggcag aactctatgc attatttaaa gaagtcattg      60
gtttgtcatt cttaaaatga tggaagggca tatactcttc ttcttttgg ttgtgatggt     120
gcagtttgtc actggggtct tggcaaatgg cctcattgtg gttgtccatg ctattgactt    180
gatcatgtgg aagaaaatgg ccccgttgga tctgcttcta ttttgcctgg cgacttctcg    240
gatcattctg cagttatgta tattgtttgc acaattgtgt ctattctctt tggtgagaca    300
cactttattt gaggacaata ttacctttgt cttcatcata aatgaactga gtctttggtt    360
tgctacatgg ctcggtgttt tctactgtgc caagattgct accattcctc acccactctt    420
tctgtggctg aagatgagga tatccaggtt ggtaccatgg ctgatcctgg atctgtgct     480
ctatgtaatt attactactt tcatccatag cagagagact tcagcaatcc ttaaaccaat    540
ttttataagc ctttttccta aaaatgcaac tcaagtcgga acagggcatg ccacactact    600
ctcagtcctg gtccttgggc tcacactgcc gttgttcatc tttactgttg ctgttctgct    660
cttgatatac tccctgtgga attatagcag gcagatgagg actatggtag caccaggga     720
gtatagcgga catgctcaca tcagtgcaat gctgtccatt ctatcattcc tcatcctcta    780
tctctcccac tacatggtgg ctgttctgat ctctactcaa gtcctctacc ttggaagcag    840
aacctttgta ttctgcttac tggttattgg tatgtacccc tcaatacact cgattgtctt    900
aattttagga atcctaagc tgaaacgaaa tgcaaaaatg ttcattgtcc attgtaagtg     960
ttgtcattgt acaagagctt gggtcacctc aaggagccca agactcagtg acttgccagt   1020
gcctcctact catccctcag ccaacaagac atcctgctca gaagcctgta taatgccatc   1080
ctaattgtcc agcctgaggt ttaatcctag gtttggtact atttcaaaga gtaaagttga   1140
tcattaaagc acaacatatg ttggtggatg acatcaaggt ccatatccca gttgtcaatt   1200
gtaaacctca ccttgcaaga tgatgtcact gagaaagcag gacaaatgga gtctaggtcc   1260
ttctgtatga cttgctgcag tatatgtgaa tctataattt tctccaaaaa aacaaaaaaa   1320
aaaaaaaaaa a                                                        1331

<210> SEQ ID NO 3
<211> LENGTH: 333
<212> TYPE: PRT
<213> ORGANISM: Rattus sp.
<220> FEATURE:
<223> OTHER INFORMATION: rat GR02

<400> SEQUENCE: 3

Met Phe Ser Gln Lys Thr Asn Tyr Ser His Leu Phe Thr Phe Ser Ile
 1               5                  10                  15

Ile Phe Tyr Val Glu Ile Val Thr Gly Ile Leu Gly Asn Gly Phe Ile
                20                  25                  30

Ala Leu Val Asn Ile Met Asp Trp Leu Lys Arg Arg Ile Ser Thr
            35                  40                  45

Ala Asp Gln Ile Leu Thr Ala Leu Ala Leu Thr Arg Leu Ile Tyr Val
        50                  55                  60

Trp Ser Val Leu Ile Cys Ile Leu Leu Leu Phe Leu Cys Pro His Leu
65                  70                  75                  80
```

```
Ser Met Arg Pro Glu Met Phe Thr Ala Ile Gly Val Ile Trp Val Val
                85                  90                  95
Asp Asn His Phe Ser Ile Trp Leu Ala Thr Cys Leu Gly Val Phe Tyr
            100                 105                 110
Phe Leu Lys Ile Ala Ser Phe Ser Asn Ser Leu Phe Leu Tyr Leu Lys
        115                 120                 125
Trp Arg Val Lys Lys Val Val Leu Met Ile Ile Leu Ile Ser Leu Ile
130                 135                 140
Phe Leu Met Leu Asn Ile Ser Ser Leu Gly Met Tyr Asp His Phe Ser
145                 150                 155                 160
Ile Asp Val Tyr Glu Gly Asn Met Ser Tyr Asn Leu Val Asp Ser Thr
                165                 170                 175
His Phe Pro Arg Ile Phe Leu Phe Thr Asn Ser Ser Lys Val Phe Leu
            180                 185                 190
Ile Ala Asn Ser Ser His Val Phe Leu Pro Ile Asn Ser Leu Phe Met
        195                 200                 205
Leu Ile Pro Phe Thr Val Ser Leu Val Ala Phe Phe Val Leu Phe Leu
210                 215                 220
Ser Leu Trp Lys His His Lys Lys Met Gln Val Asn Ala Lys Gly Pro
225                 230                 235                 240
Arg Asp Ala Ser Thr Met Ala His Thr Lys Ala Leu Gln Ile Gly Phe
                245                 250                 255
Ser Phe Leu Leu Leu Tyr Ala Ile Tyr Leu Leu Phe Ile Ile Thr Gly
            260                 265                 270
Ile Leu Asn Leu Asp Leu Met Arg Cys Ile Val Ile Leu Leu Phe Asp
        275                 280                 285
His Ile Ser Gly Ala Val Phe Ser Ile Ser His Ser Phe Val Leu Ile
290                 295                 300
Leu Gly Asn Ser Lys Leu Arg Gln Ala Thr Leu Ser Val Leu Pro Cys
305                 310                 315                 320
Leu Arg Cys Arg Ser Lys Asp Met Asp Thr Val Val Phe
                325                 330

<210> SEQ ID NO 4
<211> LENGTH: 2438
<212> TYPE: DNA
<213> ORGANISM: Rattus sp.
<220> FEATURE:
<223> OTHER INFORMATION: rat GR02

<400> SEQUENCE: 4
attttgctcc actatttgc tcttctgcag taacacagac cacaaaacaa tggagccaat      60
gggtcaagag ctgaaacttc aggaagtggg agccaaattt ctttgtgat aggttggcat    120
atgagaattc attatttgat gcagcttctg aaaactggat gtgaaatact ggatgaagca    180
gaggtgatga cccctttgaa attaaaaagc caagatgttc atggagaaat tataaaacaa    240
tatctgggaa atttgatgct tcctaatcgg gtgtaaatgg gattttaaat gatgaacatt    300
ttgaatttcc aatgaccatt atgtaaagtt tttaaacaca gtagagacat cataaattga    360
agcatgttct cacagaaaac aaactacagc catttgttta cttttccaat tattttttat    420
gtggaaatag taacaggaat cttaggaaat ggattcatag cactagtgaa atcatggac    480
tggctcaaga ggaggaggat ctctactgca gatcagattc tcactgcttt ggcccttacc    540
agactcattt atgtgtggtc tgtactcatt tgtatattgt tactattct gtgcccacat    600
ttgtctatga gaccagaaat gtttacagcg ataggtgtta tctgggtagt ggataaccac    660
```

```
ttcagcatct ggcttgctac atgtcttggt gtctttatt tcctcaaaat agccagtttt    720
tctaactctt tgtttctta cctaaagtgg agagttaaaa aagtggtttt aatgataata    780
ctgatatcac tgattttctt gatgttaaac atttcatcat tagggatgta tgatcatttc    840
tcaattgatg tttatgaagg taatatgtct tataatttgg tggattcaac acattttccc    900
agaattttct tattcacaaa ctcatctaag gtcttcttaa tcgccaattc atcccatgtt    960
ttcttaccca tcaactcact cttcatgctc atacccttca cagtttccct ggtagctttt   1020
ttcgtgctct ttctctcact gtggaagcat acaagaaga tgcaggtcaa tgccaaagga   1080
cccagagatg ccagcaccat ggcccacaca aaagccttgc aaattgggtt ctccttcctc   1140
ctgctgtatg caatatactt acttttcatt atcacaggaa ttttgaacct tgacttgatg   1200
agatgtatag taatactttt atttgaccac atatctggag cagttttttc tataagccac   1260
tcatttgtgc tgattctggg aaacagtaag ctgagacaag ccactctttc tgtgctgcct   1320
tgtcttaggt gccggtccaa agatatggac actgtcgttt tctaataaat tccagagtac   1380
attatgcaaa tcttgaggg tgatcagttc atagaaaaag taatcttaga ggggaaaata   1440
aaatattggg gcttcaaatg ttggatgggt aatacatagg aaggcaggac aaggatgaag   1500
gagactagca ttatataagt gatttcacag gggaatggg aaagagggct tttatataat   1560
gaagaagaag ataaatgatg aaggatgagg aagagttaaa tatgtaaaat gacaatagag   1620
atggcatcat gccgttttaa gaaatttgga atgcatatgt atgtttatat attttttaat   1680
ttttattgaa tatatttatt tacattttaa atgttatcct gtttccccca cccaacctcc   1740
cacctcttcc cacctccttg ccctgacatt cccctgcact ggggaatcca gccttgacag   1800
gaccaagggc ttctcctccc tttgttgcca acaaggccat tctttgctac atgtgcagca   1860
ggagccatgg atctgtctat gtgtactctt tggatggtgg tttagtccct gggagctctt   1920
gttggttggt attgttgttc ttatggtgtt gcaactccct tcagctcctt caatccttcc   1980
tgtaactcct ccaatgtgga ccctgttctc agtccaatgg ttgactatga gcattcacct   2040
ctgtgattgt catgctctgg cacagcttct cagaagacag ctacatcagt ctcctataag   2100
agtgcacttc atggcatcag caatgttgtc ttgatttggt gtctgtatgt atatgggctg   2160
gatcccaggt ggggcaggcg ctgaatggtc attccttcag tctttgctcc aaactttgtc   2220
tttatatctc ctatgaatat ttttgttccc ccttataaga atgactgaag tatccacact   2280
ttggccatcc ttcttcatga gcttcatgtg gtctgtgaat tgtacattgt gtaatccaag   2340
cttttgggct aatatccaat tatagtgagt gcataccaaa aaaaaaaaaa aaaaaaaaa   2400
aaaaaaaaa aaaaaaaaa aaaaaaaaa aaaaaaa                                2438
```

<210> SEQ ID NO 5
<211> LENGTH: 299
<212> TYPE: PRT
<213> ORGANISM: Rattus sp.
<220> FEATURE:
<223> OTHER INFORMATION: rat GR03

<400> SEQUENCE: 5

```
Met Val Pro Thr Gln Val Thr Ile Phe Ser Ile Ile Met Tyr Val Leu
  1               5                  10                  15

Glu Ser Leu Val Ile Ile Val Gln Ser Cys Thr Thr Val Ala Val Leu
             20                  25                  30

Phe Arg Glu Trp Met His Phe Gln Arg Leu Ser Pro Val Glu Ile Ile
         35                  40                  45
```

```
Leu Ile Ser Leu Gly Ile Ser His Phe Cys Leu Gln Trp Thr Ser Met
     50                  55                  60

Leu Tyr Asn Phe Gly Thr Tyr Ser Arg Pro Val Leu Phe Trp Lys
 65                  70                  75                  80

Val Ser Val Val Trp Glu Phe Met Asn Val Leu Thr Phe Trp Leu Thr
                 85                  90                  95

Ser Leu Leu Ala Val Leu Tyr Cys Val Lys Val Ser Ser Phe Ser His
            100                 105                 110

Pro Val Phe Leu Trp Leu Arg Leu Lys Ile Leu Lys Leu Val Leu Trp
        115                 120                 125

Leu Leu Leu Gly Ala Leu Ile Ala Ser Cys Leu Ser Ile Ile Pro Ser
    130                 135                 140

Val Val Lys Tyr His Ile Gln Met Glu Leu Leu Thr Leu Asp His Leu
145                 150                 155                 160

Pro Lys Asn Ser Ser Leu Ile Leu Arg Leu Gln Met Phe Glu Trp Tyr
                165                 170                 175

Phe Ser Asn Pro Phe Lys Met Ile Gly Phe Gly Val Pro Phe Leu Val
            180                 185                 190

Phe Leu Ile Ser Ile Ile Leu Leu Thr Val Ser Leu Val Gln His Trp
        195                 200                 205

Gly Gln Met Lys His Tyr Ser Ser Ser Ser Ser Leu Arg Ala Gln
    210                 215                 220

Cys Thr Val Leu Lys Ser Leu Ala Thr Phe Phe Ile Phe Phe Thr Ser
225                 230                 235                 240

Tyr Phe Leu Thr Ile Val Val Ser Phe Ile Gly Thr Val Phe Asp Lys
                245                 250                 255

Lys Ser Trp Phe Trp Val Cys Glu Ala Val Ile Tyr Gly Leu Val Cys
            260                 265                 270

Ile His Phe Thr Ser Leu Met Met Ser Asn Pro Thr Leu Lys Lys Ala
        275                 280                 285

Leu Arg Leu Gln Phe Trp Ser Pro Glu Ser Ser
    290                 295

<210> SEQ ID NO 6
<211> LENGTH: 1463
<212> TYPE: DNA
<213> ORGANISM: Rattus sp.
<220> FEATURE:
<221> NAME/KEY: modified_base
<222> LOCATION: (1403)
<223> OTHER INFORMATION: rat GR03
<223> OTHER INFORMATION: n = g, a, c or t

<400> SEQUENCE: 6
gcatggtgcc aacccaagtc accatcttct ctatcatcat gtatgtgctt gagtccttag      60
tcataattgt gcaaagttgc acaacggttg cagtgctgtt cagagagtgg atgcactttc     120
aaagactgtc gccggtggaa ataattctca tcagcctggg catttcacat ttctgtctac     180
agtggacatc gatgctgtac aactttggta cctactctag gcctgtcctt ttattttgga     240
aggtatcggt cgtctgggag ttcatgaacg ttttgacatt ctggctaacc agtttgcttg     300
ctgtcctcta ctgtgtcaag gtctcttcct tctctcaccc cgtcttcctc tggctgaggt     360
tgaaaatttt gaaactggtt ctctggttgc tattgggcgc tctgatagct tcttgtttgt     420
caatcatccc ttctgttgtt aaatatcata tccagatgga attactcacc ctagatcatt     480
tacccaaaaa cagttctttg attctaagac tgcaaatgtt cgagtggtat tttctaatc     540
```

-continued

```
ctttcaaaat gattgggttt ggcgttcctt tcctcgtgtt cctgatttct atcatcttac    600
tcacagtctc gctggtccag cattgggggc agatgaaaca ctacagcagc agcagctcca    660
gcctgagagc tcagtgcact gttctgaagt ctcttgccac cttcttcatc ttcttcacat    720
cctattttct gactatagtc gtctccttta ttggcaccgt gtttgataag aagtcatggt    780
tctgggtctg cgaagctgtc atctatggtt tagtctgtat tcacttcact tccctgatga    840
tgagcaaccc tacactgaaa aaagcactca ggttgcagtt ctggagccca gagtcttcct    900
aaggcaggga attcacaagg gaaagtgact cttcagattt aagtttaaaa ttagaagaga    960
gataaatttc ccaagctttc actcctaagg ctaaagatag gctgtgtagg tagttatttc   1020
tgagcacatt ggcacatcac cattgtcagt acttgagggt ttgaatgaag ctcactcaaa   1080
gaacttggaa agaaggtggt cttctgacat caatcaagaa acaagctttc ctccctactt   1140
cttccctaaa tgcaacaacc taagaattat ccacaagatg gatggcgcaa gggttcctca   1200
atcaatttca ggatgtacat caatgcgcag cctatactac accgaaaagg aagcgcatgg   1260
gtcttaaaaa gtaaagggga tatcaaaaaa ttcgcaacca acaaaaagt ggcacacatt    1320 taagctaggt ctatgtttgg tcagttacac ctggagaagg gggacatttg gtcagctcat   1380
tcgaacactg tcaagtccta ccnacaattc ctctatgcta ttacccatta aacctcaggt   1440
ctcatcgaaa aaaaaaaaaa aaa                                           1463
```

<210> SEQ ID NO 7
<211> LENGTH: 310
<212> TYPE: PRT
<213> ORGANISM: Rattus sp.
<220> FEATURE:
<223> OTHER INFORMATION: rat GR04

<400> SEQUENCE: 7

```
Met Leu Ser Ala Ala Glu Gly Ile Leu Leu Cys Val Val Thr Ser Glu
  1               5                  10                  15

Ala Val Leu Gly Val Leu Gly Asp Thr Phe Ile Ala Leu Ala Asn Cys
             20                  25                  30

Met Glu Tyr Ala Lys Asn Lys Lys Leu Ser Lys Ile Gly Phe Ile Leu
         35                  40                  45

Ile Gly Leu Ala Ile Ser Arg Ile Gly Val Val Trp Ile Ile Ile Leu
     50                  55                  60

Gln Gly Tyr Met Gln Val Phe Phe Pro His Ile Leu Thr Phe Gly Asn
 65                  70                  75                  80

Ile Thr Glu Tyr Ile Thr Tyr Ile Trp Val Phe Leu Asn His Leu Ser
                 85                  90                  95

Val Trp Phe Ala Thr Asn Leu Asn Ile Leu Tyr Phe Leu Lys Ile Ala
            100                 105                 110

Asn Phe Ser Asn Ser Val Phe Leu Trp Leu Lys Ser Arg Val Arg Val
        115                 120                 125

Val Phe Ile Phe Leu Ser Gly Cys Leu Leu Thr Ser Trp Leu Leu Cys
    130                 135                 140

Phe Pro Gln Phe Ser Lys Met Leu Asn Asn Ser Lys Met Tyr Trp Gly
145                 150                 155                 160

Asn Thr Ser Trp Leu Gln Gln Lys Asn Val Phe Leu Ile Asn Gln
                165                 170                 175

Ser Leu Thr Asn Leu Gly Ile Phe Phe Phe Ile Ile Val Ser Leu Ile
            180                 185                 190
```

```
Thr Cys Phe Leu Leu Ile Val Phe Leu Trp Arg His Ile Arg Gln Met
        195                 200                 205

His Ser Asp Gly Ser Gly Leu Arg Asp Leu Asn Thr Glu Ala His Val
    210                 215                 220

Lys Ala Met Arg Val Leu Ile Ser Phe Ala Val Leu Phe Ile Leu His
225                 230                 235                 240

Phe Val Gly Leu Ser Ile Gln Val Leu Cys Phe Phe Leu Pro Gln Asn
                245                 250                 255

Asn Leu Leu Phe Ile Thr Gly Leu Ile Ala Thr Cys Leu Tyr Pro Cys
            260                 265                 270

Gly His Ser Ile Ile Leu Ile Leu Gly Asn Lys Gln Leu Lys Gln Ala
        275                 280                 285

Ser Leu Lys Ala Leu Gln Leu Gln His Leu Thr Cys Cys Glu Thr Lys
    290                 295                 300

Arg Asn Leu Ser Val Thr
305                 310

<210> SEQ ID NO 8
<211> LENGTH: 1540
<212> TYPE: DNA
<213> ORGANISM: Rattus sp.
<220> FEATURE:
<223> OTHER INFORMATION: rat GR04 sequence approximately 1100 bp 5' to
      SEQ ID NO:92

<400> SEQUENCE: 8
tggttccatc acatgacaat aggcttgaaa aacttgcaga tagagaagac ataacccctc      60
caacaagaag ccaacatatg ggacattctc cagcagataa tttataacag atgcaacggg     120
agcaacttcg agatctgcaa agatgctgag tgcagcagaa ggcatcctcc tttgtgttgt     180
cactagtgag gcagtgctgg gggttttagg agacacattc attgcacttg caaactgcat     240
ggagtatgcc aagaacaaga agctctctaa gattggtttc attctcattg cttggcgat      300 ttccagaatt ggtgtcgtat ggataataat tttacagggg tatatgcaag tatttttttcc    360 acacatactt acctttggaa acataactga atatattact tacatatggg tgtttctcaa     420
tcacttaagt gtctggtttg ctaccaacct caatatcctc tactttctaa agatagcaaa     480
tttttccaac tctgtatttc tctggctgaa agtagagtc cgtgtggttt ttatctttct     540
gtcaggatgc ttacttacct cgtggttact atgttttcca cattttcaa agatgcttaa     600 caacagtaaa atgtactggg gaaacacgtc ttggctccag cagcagaaaa atgtcttcct     660
tattaaccaa agtttaacca atctgggaat cttcttttc attattgtat ccctgattac     720
ctgcttcctg ttgattgttt tcctctggag acacatcagg caaatgcact cagatggttc     780
aggactcaga gacctcaaca cagaagctca tgtgaaagcc atgagagttc taatatcttt     840
tgcggtactc tttatcctgc atttcgtagg tcttttccata caagtgctat gcttttttct     900
gccacaaaac aacctactct ttataactgg tttgatagcc acatgcctct atccctgtgg     960
tcactcaatc atcttaattc taggaaacaa gcaagctgaag caagcctcct tgaaggcact   1020
gcagcactta acgtgctgtg agacaaaaag aaatctctca gtcacataaa tgggtttgcc   1080
aattaatatc tgccatgtta ttccactgat ttttacctgt tagtttctct gtgtctctgt   1140
ttagtttctg tttccatgat ctgtccattg atgagcgtgg ggtgttgaaa tctccgacta   1200
ttgttgtgtg agatgaaatg tgtgcttga gctttagtaa gatttctttt gtgaatgtag   1260
gtgcttttgc atttggtgca tagatatttta agattgagag ttcagcttgg tggatttttc   1320
```

```
cttgtgatgaa tatgaagtgt ccttgcttat ctttttttgat gacttttgat tgaacgtcaa    1380 tttattgga tattagattg gcaactcaag attgcttctt gaggtcattt gcttggaaag       1440
ttgtttttca gccatttact ctgaggtagt gtctgtcttt gtctctgagg tgtgtttcct      1500
gcattcagca aaatgctggg tcctctttac atatccagtt                            1540
```

<210> SEQ ID NO 9
<211> LENGTH: 224
<212> TYPE: PRT
<213> ORGANISM: Rattus sp.
<220> FEATURE:
<223> OTHER INFORMATION: rat GR05

<400> SEQUENCE: 9

```
Met Leu Gly Ala Met Glu Gly Val Leu Leu Ser Val Ala Thr Ser Glu
  1               5                  10                  15

Ala Leu Leu Gly Ile Val Gly Asn Thr Phe Ile Ala Leu Val Asn Cys
             20                  25                  30

Met Asp Cys Thr Arg Asn Lys Asn Leu Tyr Asn Ile Gly Phe Ile Leu
         35                  40                  45

Thr Gly Leu Ala Ile Ser Arg Ile Cys Leu Val Trp Ile Leu Ile Thr
     50                  55                  60

Glu Ala Tyr Ile Lys Ile Phe Ser Pro Gln Leu Leu Ser Pro Ile Asn
 65                  70                  75                  80

Ile Ile Glu Leu Ile Ser Tyr Leu Trp Ile Ile Thr Ser Gln Leu Asn
                 85                  90                  95

Val Trp Phe Ala Thr Ser Leu Ser Ile Phe Tyr Phe Leu Lys Ile Ala
            100                 105                 110

Asn Phe Ser His His Ile Phe Leu Trp Leu Lys Arg Arg Ile Asn Ile
        115                 120                 125

Val Phe Ala Phe Leu Ile Gly Cys Leu Leu Met Ser Trp Leu Phe Ser
    130                 135                 140

Phe Pro Val Val Val Lys Met Val Lys Asp Lys Lys Met Leu Tyr Ile
145                 150                 155                 160

Asn Ser Ser Trp Gln Ile His Met Lys Lys Ser Glu Leu Ile Ile Asn
                165                 170                 175

Tyr Val Phe Thr Asn Gly Gly Val Phe Leu Leu Phe Ile Ile Met Val
            180                 185                 190

Ile Gly Cys Phe Leu Leu Ile Ile Ser Leu Trp Arg His Ser Lys Trp
        195                 200                 205

Met Gln Ser Asn Glu Ser Gly Phe Arg Asp Leu Asn Thr Glu Val His
    210                 215                 220
```

<210> SEQ ID NO 10
<211> LENGTH: 819
<212> TYPE: DNA
<213> ORGANISM: Rattus sp.
<220> FEATURE:
<223> OTHER INFORMATION: rat GR05

<400> SEQUENCE: 10

```
aagagatttc agatactacc acaaacattt tttaaatata tgtaagtctt taagaaaga      60 agggaaagcc actcctttat tgagcagcca atagattgcc atcttaaaat tctgtggcag     120
aagctatttt aaagatctgc gaagatgctg ggtgcaatgg aaggtgtcct cctttcagtt     180
gcaactagtg aggcttttgct tggcattgta gggaacacat tcattgcact tgtgaactgc    240
atggactgta ccaggaacaa gaatctctat aatattggct tcattctcac tggcttggca    300
```

```
atttccagaa tctgcctcgt gtggatctta atcacagagg catacataaa aatattctct    360
ccacagttgc tgtctcctat caacataatt gaactcatca gttatctatg gataattacc    420
agtcaattga atgtttggtt tgctaccagc ctcagtatct tttatttcct caagatagca    480
aattttcccc accacatatt tctctggtta aaaagaagaa ttaatatagt ttttgccttc    540
ctgatagggt gcttacttat gtcatggcta ttttctttcc cagtagttgt gaagatggtt    600
aaagataaaa aaatgctgta tataaactca tcttggcaaa tccacatgaa gaaaagtgag    660
ttaatcatta actatgtttt caccaatggg ggagtatttt tacttttat aataatggta     720 attggatgtt ttctcttaat tatttcccct tggagacaca gcaagtggat gcaatcaaat    780
gaatcaggat tcagagatct caacacagaa gttcatgtg                            819
```

```
<210> SEQ ID NO 11
<211> LENGTH: 77
<212> TYPE: PRT
<213> ORGANISM: Mus sp.
<220> FEATURE:
<221> NAME/KEY: MOD_RES
<222> LOCATION: (1)..(77)
<223> OTHER INFORMATION: mouse GR01
<223> OTHER INFORMATION: Xaa = any amino acid

<400> SEQUENCE: 11
```

Met Leu Arg His Cys Ser Lys Glu Asn Glu Cys Leu Gly Asp Gly Phe
 1               5                  10                  15

Ile Gly Phe Val Asn Cys Met Asp Trp Val Lys Arg Arg Lys Leu Phe
             20                  25                  30

Leu Val Asn Gln Leu Leu Thr Leu Leu Val Ile Ser Arg Ile Thr Val
         35                  40                  45

Leu Xaa Val Leu Leu Leu Asn Cys Trp Leu Tyr Asn Xaa Tyr Phe Phe
     50                  55                  60

Phe Thr Val Asn Ser Tyr Phe Xaa Xaa Phe Tyr Lys Asn
 65                  70                  75

```
<210> SEQ ID NO 12
<211> LENGTH: 427
<212> TYPE: DNA
<213> ORGANISM: Mus sp.
<220> FEATURE:
<223> OTHER INFORMATION: mouse GR01

<400> SEQUENCE: 12
gaattcaatt tttctttcct ctgtaacaga aggtcataca taactcctgt gtatgaagta    60
catattgtaa agaaggttca gcttattact gaatgtgttc attttcataa tggaaaacat    120
aattgagttt tcatgaagca gatactactc atatttagat gaactaatta agtaatattc    180
atcaggaatg actgatgttg agacattgtt ctaaggagaa tgagtgtttg ggagatggat    240
ttataggatt tgtgaactgc atggactggg tcaagagaag aaagctcttt ttggtgaatc    300
aactcctcac tcttctggtc atctccagaa tcactgtcct ctgagtacta cttctaaatt    360
gttggctata taactaatat tttttttta ctgtaaactc ttatttttga tgattctata    420
agaattc                                                               427
```

```
<210> SEQ ID NO 13
<211> LENGTH: 209
<212> TYPE: PRT
<213> ORGANISM: Mus sp.
```

```
<220> FEATURE:
<223> OTHER INFORMATION: mouse GR02

<400> SEQUENCE: 13

Asn Ser Ser Val Pro Gly Asp Pro Leu Glu Ser Thr Cys Arg His
 1               5                   10                  15

Ala Ser Leu Val Phe Leu Gly Asn Leu Met Gln Ser Met Leu Glu
             20                  25                  30

Glu Arg Phe Tyr Gln Tyr Gly Arg Asn Thr Ser Val Asn Thr Met Ser
         35                  40                  45

Asn Asp Leu Ala Met Trp Thr Glu Leu Ile Phe Phe Asn Met Ala Met
 50                  55                  60

Phe Ser Val Ile Pro Phe Thr Leu Ala Leu Ile Ser Phe Leu Leu Leu
 65                  70                  75                  80

Ile Phe Ser Leu Trp Lys His Leu Gln Lys Met Gln Leu Ile Ser Arg
             85                  90                  95

Arg His Arg Asp Pro Ser Thr Lys Ala His Met Asn Ala Leu Arg Ile
            100                 105                 110

Met Val Ser Phe Leu Leu Leu Tyr Thr Met His Phe Leu Ser Leu Leu
            115                 120                 125

Ile Ser Trp Ile Ala Gln Lys His Gln Ser Glu Leu Ala Asp Ile Ile
130                 135                 140

Gly Met Ile Thr Glu Leu Met Tyr Pro Ser Val His Ser Cys Ile Leu
145                 150                 155                 160

Ile Leu Gly Asn Ser Lys Leu Lys Gln Thr Ser Leu Cys Met Leu Arg
                165                 170                 175

His Leu Arg Cys Arg Leu Lys Gly Glu Asn Ile Thr Ile Ala Tyr Ser
            180                 185                 190

Asn Gln Ile Thr Ser Phe Cys Val Phe Cys Val Ala Asn Lys Ser Met
        195                 200                 205

Arg

<210> SEQ ID NO 14
<211> LENGTH: 1361
<212> TYPE: DNA
<213> ORGANISM: Mus sp.
<220> FEATURE:
<223> OTHER INFORMATION: mouse GR02

<400> SEQUENCE: 14
ggaattcgag ctcggtaccc ggggatcctc tagagtcgac ctgcaggcat gcaagcttgg      60
tgttcttgct tggaaatctg atgcaaagca tgcttgaaga gaggttctat caatatggaa    120
ggaacacaag tgtgaatacc atgagcaatg accttgcaat gtggaccgag ctgatctttt    180
tcaacatggc tatgttctct gtaataccat ttacattggc cttgatttct tttctcctgc    240
taatcttctc tttgtggaaa catctccaga agatgcagct catttccaga agacacagag    300
accctagcac caaggcccac atgaatgcct tgagaattat ggtgtccttc ctcttgctct    360
ataccatgca tttcctgtct cttcttatat catggattgc tcaaaagcat cagagtgaac    420
tggctgatat tattggtatg ataactgaac tcatgtatcc ttcagtccat tcatgtatcc    480
tgattctagg aaattctaaa ttaaagcaga cttctctttg tatgctgagg catttgagat    540
gtaggctgaa aggagagaat atcacaattg catatagcaa ccaaataact agcttttgtg    600
tattctgtgt tgcaaacaaa tctatgaggt agttgttcaa ggaatccttc cttgacttat    660
tgtatcatgg aagtcatatg ggggagtctg aaagagctgt cttctgtaag caaggtttgt    720
```

```
atacactagt gggctggga caccaaccca agcacaaaac ctagctataa cctatcctgg     780
ctgcaggata tgctggaaca atggtggctt ggaaattgtg ggactggcaa agcaatagct    840
agtctaactt gaggcccatt ccacagcagg aagctcatgc ccacctctgc ctggatggcc    900
aggaagcaaa atcttgatgg ccccaagacc tatggtaaac tgaacactac tggaaaaga    960 aagactcgtg ttaatgatct atcaaatatt tcctaatgat attctgataa actcatatat   1020
tagtccctgt cctaatcatc atcactggga ctccttccca gcacctgatg ggagcagata   1080
gagatctaca tccaaatagt aagtgtatct tggggaactc cacttaagaa tagaaggaac   1140
aattatgaga gccagagtga tccagaacac taggatcaca gaatcaacta agcagcatgc   1200 atagggtta atggagactg aagtggcaat cacagagcct gcataggtct acactaagtc    1260
ctctgtgtat atactgtggc tgtttagctt aggaattttg ttggactcct aacaatggat   1320
aaggaattct gcagatatcc atcacactgc cgcccgtcga g                       1361
```

<210> SEQ ID NO 15
<211> LENGTH: 266
<212> TYPE: PRT
<213> ORGANISM: Mus sp.
<220> FEATURE:
<223> OTHER INFORMATION: mouse GR03

<400> SEQUENCE: 15

```
Ala Val Asp Lys Thr Tyr Met Ala Leu Ala Ile Ser Arg Thr Ala Phe
  1               5                  10                  15

Leu Leu Ser Leu Ile Thr Gly Phe Leu Val Ser Leu Leu Asp Pro Ala
             20                  25                  30

Leu Leu Gly Met Arg Thr Met Val Arg Leu Leu Thr Ile Ser Trp Met
         35                  40                  45

Val Thr Asn His Phe Ser Val Trp Phe Ala Thr Cys Leu Ser Ile Phe
     50                  55                  60

Tyr Phe Leu Lys Ile Ala Asn Phe Ser Asn Ser Ile Phe Leu Val Leu
 65                  70                  75                  80

Lys Trp Glu Ala Lys Lys Val Val Ser Val Thr Leu Val Val Ser Val
                 85                  90                  95

Ile Ile Leu Ile Met Asn Ile Ile Val Ile Asn Lys Phe Thr Asp Arg
            100                 105                 110

Leu Gln Val Asn Thr Leu Gln Asn Cys Ser Thr Ser Asn Thr Leu Lys
        115                 120                 125

Asp Tyr Gly Leu Phe Leu Phe Ile Ser Thr Gly Phe Thr Leu Thr Pro
    130                 135                 140

Phe Ala Val Ser Leu Thr Met Phe Leu Leu Ile Phe Ser Leu Trp
145                 150                 155                 160

Arg His Leu Lys Asn Met Cys His Ser Ala Thr Gly Ser Arg Asp Val
                165                 170                 175

Ser Thr Val Ala His Ile Lys Gly Leu Gln Thr Val Thr Phe Leu
            180                 185                 190

Leu Leu Tyr Thr Ala Phe Val Met Ser Leu Ser Glu Ser Leu Asn
        195                 200                 205

Ile Asn Ile Gln His Thr Asn Leu Leu Ser His Phe Leu Arg Ser Ile
    210                 215                 220

Gly Val Ala Phe Pro Thr Gly His Ser Cys Val Leu Ile Leu Gly Asn
225                 230                 235                 240

Ser Lys Leu Arg Gln Ala Ser Leu Ser Val Ile Leu Trp Leu Arg Tyr
```

245                 250                 255
Lys Tyr Lys His Ile Glu Asn Trp Gly Pro
            260                 265

<210> SEQ ID NO 16
<211> LENGTH: 1739
<212> TYPE: DNA
<213> ORGANISM: Mus sp.
<220> FEATURE:
<221> NAME/KEY: modified_base
<222> LOCATION: (1)..(1739)
<223> OTHER INFORMATION: mouse GR03
<223> OTHER INFORMATION: n = g, a, c or t

<400> SEQUENCE: 16

| | | | | | |
|---|---|---|---|---|---|
| ctgcagtgga | taagacctat | atggccctgg | ccatctccag | gactgctttt | ttattgtcac | 60 |
| taatcacagg | gttcttggta | tcattattgg | acccagcttt | attgggaatg | agaacgatgg | 120 |
| taaggctcct | tactatttcc | tggatggtga | ccaatcattt | cagtgtctgg | tttgcaacat | 180 |
| gcctcagtat | ctttatttt | ctcaagatag | ctaatttctc | aaattctatt | ttccttgttc | 240 |
| tcaaatggga | agctaaaaaa | gtggtatcag | tgacattggt | ggtatctgtg | ataatcttga | 300 |
| tcatgaacat | tatagtcata | aacaaattca | ctgacagact | tcaagtaaac | acactccaga | 360 |
| actgtagtac | aagtaacact | ttaaaagatt | atgggctctt | tttattcatt | agcactgggt | 420 |
| ttacactcac | cccattcgct | gtgtctttga | caatgtttct | tctgctcatc | ttctccctgt | 480 |
| ggagacatct | gaagaatatg | tgtcacagtg | ccacaggctc | cagagatgtc | agcacagtgg | 540 |
| cccacataaa | aggcttgcaa | actgtggtaa | ccttcctgtt | actatatact | gcttttgtta | 600 |
| tgtcacttct | ttcagagtct | ttgaatatta | acattcaaca | tacaaatctt | ctttctcatt | 660 |
| ttttacggag | tataggagta | gcttttccca | caggccactc | ctgtgtactg | attcttggaa | 720 |
| acagtaagct | gaggcaagcc | tctctttctg | tgatattgtg | gctgaggtat | aagtacaaac | 780 |
| atatagagaa | ttggggcccc | taaatcatat | cagggatcct | tttccacatt | ctagaaaaaa | 840 |
| atcagttaat | aagaacagga | atttaggaag | gaatctgaaa | ttatgaatct | cataggccat | 900 |
| gaaccttcag | acaaaggatt | cattagagag | atagagagag | aacattgtta | tctgtaactc | 960 |
| gacaggcaac | actgtagatt | atgaaaataa | atgtcagtct | gtaatggaaa | gcaaaacatg | 1020 |
| ctatatttta | ttaattggtt | ttggtttaag | gtcgggatan | gagantaagg | gagtggtgga | 1080 |
| agggttgtgg | catgaggaat | ggcctaaggc | tagctgattc | attgaacccg | agatgagaac | 1140 |
| aaaatggtct | agagtctgac | tataggggtg | ctccagttgn | ccatggcttt | cctggataan | 1200 |
| angccctgca | ggnccatngn | gactagttca | tgtataatac | aatagtggat | aattgttgtg | 1260 |
| tatnaatgtc | cttttccttg | aatcttgctg | tctgnaaaag | ccncaggagt | gagaagaact | 1320 |
| atggtgaatg | aaagatggat | ggaaaaggga | aaacaagact | gaaagggtgc | aggttgattt | 1380 |
| aatgacaatg | gatgcttatt | tgtgtaaatt | tatcctttgt | aaacatgttt | cagtcatgtg | 1440 |
| taactttatg | aagtttaggc | aattctatgt | agatgaataa | gtatccaaac | acagtcgagc | 1500 |
| cctatagaaa | aggagaaatt | atggacattg | acagagaagt | aaaatatagg | tttggcctat | 1560 |
| cttttattgg | gcatacagat | attgttatcc | catgtttcag | gtaaagatca | acttagaaaa | 1620 |
| ttaaaaaaaa | aaatcagtgc | caaatagcaa | gtgtgtttac | ctactgaatt | atcgtcttcc | 1680 |
| tctttaggta | gtcaggaaaa | cagaactaat | gcaacagtct | tgtcttcttt | cctctgcag | 1739 |

<210> SEQ ID NO 17
<211> LENGTH: 300

```
<212> TYPE: PRT
<213> ORGANISM: Mus sp.
<220> FEATURE:
<223> OTHER INFORMATION: mouse GR04

<400> SEQUENCE: 17
```

| | | | | | | | | | | | | | | | |
|---|---|---|---|---|---|---|---|---|---|---|---|---|---|---|---|
| Met | Leu | Ser | Ala | Leu | Glu | Ser | Ile | Leu | Leu | Ser | Val | Ala | Thr | Ser | Glu |
| 1 | | | | 5 | | | | | 10 | | | | | 15 | |
| Ala | Met | Leu | Gly | Val | Leu | Gly | Asn | Thr | Phe | Ile | Val | Leu | Val | Asn | Tyr |
| | | | 20 | | | | | 25 | | | | | 30 | | |
| Thr | Asp | Trp | Val | Arg | Asn | Lys | Lys | Leu | Ser | Lys | Ile | Asn | Phe | Ile | Leu |
| | | 35 | | | | | 40 | | | | | 45 | | | |
| Thr | Gly | Leu | Ala | Ile | Ser | Arg | Ile | Phe | Thr | Ile | Trp | Ile | Ile | Thr | Leu |
| 50 | | | | | 55 | | | | | 60 | | | | | |
| Asp | Ala | Tyr | Thr | Lys | Val | Phe | Leu | Leu | Thr | Met | Leu | Met | Pro | Ser | Ser |
| 65 | | | | | 70 | | | | | 75 | | | | | 80 |
| Leu | His | Glu | Cys | Met | Ser | Tyr | Ile | Trp | Val | Ile | Ile | Asn | His | Leu | Ser |
| | | | | 85 | | | | | 90 | | | | | 95 | |
| Val | Trp | Phe | Ser | Thr | Ser | Leu | Gly | Ile | Phe | Tyr | Phe | Leu | Lys | Ile | Ala |
| | | | | 100 | | | | | 105 | | | | | 110 | |
| Asn | Phe | Ser | His | Tyr | Ile | Phe | Leu | Trp | Met | Lys | Arg | Arg | Ala | Asp | Lys |
| | | | 115 | | | | | 120 | | | | | 125 | | |
| Val | Phe | Val | Phe | Leu | Ile | Val | Phe | Leu | Ile | Ile | Thr | Trp | Leu | Ala | Ser |
| | | 130 | | | | | 135 | | | | | 140 | | | |
| Phe | Pro | Leu | Ala | Val | Lys | Val | Ile | Lys | Asp | Val | Lys | Ile | Tyr | Gln | Ser |
| 145 | | | | | 150 | | | | | 155 | | | | | 160 |
| Asn | Thr | Ser | Trp | Leu | Ile | His | Leu | Glu | Lys | Ser | Glu | Leu | Leu | Ile | Asn |
| | | | | 165 | | | | | 170 | | | | | 175 | |
| Tyr | Val | Phe | Ala | Asn | Met | Gly | Pro | Ile | Ser | Leu | Phe | Ile | Val | Ala | Ile |
| | | | | 180 | | | | | 185 | | | | | 190 | |
| Ile | Ala | Cys | Phe | Leu | Leu | Thr | Ile | Ser | Leu | Trp | Arg | His | Ser | Arg | Gln |
| | | | 195 | | | | | 200 | | | | | 205 | | |
| Met | Gln | Ser | Ile | Gly | Ser | Gly | Phe | Arg | Asp | Leu | Asn | Thr | Glu | Ala | His |
| | | 210 | | | | | 215 | | | | | 220 | | | |
| Met | Lys | Ala | Met | Lys | Val | Leu | Ile | Ala | Phe | Ile | Ile | Leu | Phe | Ile | Leu |
| 225 | | | | | 230 | | | | | 235 | | | | | 240 |
| Tyr | Phe | Leu | Gly | Ile | Leu | Ile | Glu | Thr | Leu | Cys | Leu | Phe | Leu | Thr | Asn |
| | | | | 245 | | | | | 250 | | | | | 255 | |
| Asn | Lys | Leu | Leu | Phe | Ile | Phe | Gly | Phe | Thr | Leu | Ser | Ala | Met | Tyr | Pro |
| | | | | 260 | | | | | 265 | | | | | 270 | |
| Cys | Cys | His | Ser | Phe | Ile | Leu | Ile | Leu | Thr | Ser | Arg | Glu | Leu | Lys | Gln |
| | | | 275 | | | | | 280 | | | | | 285 | | |
| Asp | Thr | Met | Arg | Ala | Leu | Gln | Arg | Leu | Lys | Met | Leu | | | | |
| | | 290 | | | | | 295 | | | | | 300 | | | |

```
<210> SEQ ID NO 18
<211> LENGTH: 1532
<212> TYPE: DNA
<213> ORGANISM: Mus sp.
<220> FEATURE:
<221> NAME/KEY: modified_base
<222> LOCATION: (970)
<223> OTHER INFORMATION: mouse GR04
<223> OTHER INFORMATION: n = g, a, c or t

<400> SEQUENCE: 18
ctgcagcagg taaatcacac cagatccagc agaagccttc ttggaaattg gcagagatgc    60
```

```
tgagtgcact ggaaagcatc ctcctttctg ttgccactag tgaagccatg ctgggagttt      120
tagggaacac atttattgta cttgtaaact acacagactg ggtcaggaat aagaaactct      180
ctaagattaa cttattctc actggcttag caatttccag gattttacc atatggataa        240 taactttaga tgcatataca aaggttttcc ttctgactat gcttatgccg agcagtctac      300
atgaatgcat gagttacata tgggtaatta ttaaccatct gagcgtttgg tttagcacca     360
gcctcggcat ctttattt ctgaagatag caaattttc ccactacata tttctctgga         420
tgaagagaag agctgataaa gttttgtct ttctaattgt attcttaatt ataacgtggc        480
tagcttcctt tccgctagct gtgaaggtca ttaaagatgt taaaatatat cagagcaaca     540
catcctggct gatccacctg gagaagagtg agttacttat aaactatgtt tttgccaata      600
tggggcccat ttccctcttt attgtagcca taattgcttg tttcttgtta accatttccc     660
tttggagaca cagcaggcag atgcaatcca ttggatcagg attcagagat ctcaacacag    720
aagctcacat gaaagccatg aaagttttaa ttgcatttat catcctcttt atcttatatt     780
ttttgggtat tctcatagaa acattatgct tgtttcttac aaacaataaa cttctcttta     840
tttttggctt cactttgtca gccatgtatc cctgttgcca ttcctttatc ctaattctaa      900
caagcaggga gctgaagcaa gacactatga gggcactgca gagattaaaa atgctgtgag    960
actttgacan agaaatgaat gttctggcac agttcaagca gggaatccct ggagcccttt   1020
ccattcccac tatgttctca cactgtcttt agttgaattg ttaaaagttt tgaaaccttt    1080
tggcaactga ttgactgcag ctacgccagt gtaagatttt catagtaaga gcaaacattg    1140
aaaataagac ttctcagtct tatttcattg agtttctaaa gcattgacac ccattcacca   1200
gaaaaaccaa aggggaagag aggagttttc agacatgtgt gatgaatctt gatatttagg    1260
acatggaatt gaggagccag agggatgcta ccgtgtgtct acagctttgt tgttaaata      1320 gctactttc ctttcccagt tagttaaagt agatgcttgg agtagtggtg aaaatcatgg     1380
cagtagatgg gatctgtggg aagtggttga ggaagcaggc tgtttctgaa cgaagagacc    1440
agaggactga ttgaactggt cattgtgtat atcaaaaata gtgatttcag atgaagccaa    1500
gttgtagagc aaagatatct gaggaagaat tc                                  1532
```

<210> SEQ ID NO 19
<211> LENGTH: 300
<212> TYPE: PRT
<213> ORGANISM: Mus sp.
<220> FEATURE:
<223> OTHER INFORMATION: mouse GR05

<400> SEQUENCE: 19

```
Met Leu Ser Ala Ala Glu Gly Ile Leu Leu Ser Ile Ala Thr Val Glu
 1               5                  10                  15

Ala Gly Leu Gly Val Leu Gly Asn Thr Phe Ile Ala Leu Val Asn Cys
            20                  25                  30

Met Asp Trp Ala Lys Asn Asn Lys Leu Ser Met Thr Gly Phe Leu Leu
        35                  40                  45

Ile Gly Leu Ala Thr Ser Arg Ile Phe Ile Val Trp Leu Leu Thr Leu
    50                  55                  60

Asp Ala Tyr Ala Lys Leu Phe Tyr Pro Ser Lys Tyr Phe Ser Ser Ser
65                  70                  75                  80

Leu Ile Glu Ile Ile Ser Tyr Ile Trp Met Thr Val Asn His Leu Thr
                85                  90                  95

Val Trp Phe Ala Thr Ser Leu Ser Ile Phe Tyr Phe Leu Lys Ile Ala
```

```
                 100                 105                 110
Asn Phe Ser Asp Cys Val Phe Leu Trp Leu Lys Arg Arg Thr Asp Lys
            115                 120                 125

Ala Phe Val Phe Leu Leu Gly Cys Leu Leu Thr Ser Trp Val Ile Ser
130                 135                 140

Phe Ser Phe Val Val Lys Val Met Lys Asp Gly Lys Val Asn His Arg
145                 150                 155                 160

Asn Arg Thr Ser Glu Met Tyr Trp Glu Lys Arg Gln Phe Thr Ile Asn
                165                 170                 175

Tyr Val Phe Leu Asn Ile Gly Val Ile Ser Leu Phe Met Met Thr Leu
            180                 185                 190

Thr Ala Cys Phe Leu Leu Ile Met Ser Leu Trp Arg His Ser Arg Gln
        195                 200                 205

Met Gln Ser Gly Val Ser Gly Phe Arg Asp Leu Asn Thr Glu Ala His
    210                 215                 220

Val Lys Ala Ile Lys Phe Leu Ile Ser Phe Ile Leu Phe Val Leu
225                 230                 235                 240

Tyr Phe Ile Gly Val Ser Ile Glu Ile Cys Ile Phe Ile Pro Glu
                245                 250                 255

Asn Lys Leu Leu Phe Ile Phe Gly Phe Thr Thr Ala Ser Ile Tyr Pro
            260                 265                 270

Cys Cys His Ser Phe Ile Leu Ile Leu Ser Asn Ser Gln Leu Lys Gln
        275                 280                 285

Ala Phe Val Lys Val Leu Gln Gly Leu Lys Phe Phe
    290                 295                 300

<210> SEQ ID NO 20
<211> LENGTH: 1084
<212> TYPE: DNA
<213> ORGANISM: Mus sp.
<220> FEATURE:
<223> OTHER INFORMATION: mouse GR05

<400> SEQUENCE: 20
ctgcagcaga tctactatag atgcaacaga tacaacttga gggacctgga gatatgctga      60
gtgcggcaga aggcatcctc ctttccattg caactgttga agctgggctg ggagttttag     120
ggaacacatt tattgcactg gtaaactgca tggactgggc aagaacaat aagctttcta     180
tgactggctt ccttctcatc ggcttagcaa cttccaggat tttatttgtg tggctattaa     240
ctttagatgc atatgcaaag ctattctatc caagtaagta ttttttctagt agtctgattg     300
aaatcatctc ttatatatgg atgactgtga atcacctgac tgtctggttt gccaccagcc     360
taagcatctt ctatttcctg aagatagcca attttttccga ctgtgtattt ctctggttga     420
agaggagaac ggataaagct tttgtttttc tcttggggtg tttgctaact tcatgggtaa     480
tctccttctc atttgttgtg aaggtgatga aggacgttaa agtgaatcat agaaacagga     540
cctcggagat gtactgggag aaaaggcaat tcactattaa ctacgttttc ctcaatattg     600
gagtcatttc tctctttatg atgaccttaa ctgcatgttt cttgttaatt atgtcacttt     660
ggagacacag caggcagatg cagtctggtg tttcaggatt cagagacctc aacacagaag     720
ctcatgtgaa agccataaaa ttttaatttt catttatcat ccttttcgtc ttgtatttta     780
taggtgtttc aatagaaatt atctgcatat ttataccaga aaacaaactg ctatttattt     840
ttggtttcac aactgcatcc atatatcctt gctgtcactc atttattcta attctatcta     900
acagccagct aaagcaagcc tttgtaaagg tactgcaagg attaaagttc ttttagaaaa     960
```

```
gaaaagctct cagggtcaca tgcgtctgaa acagaaatgc gtaatttaga ataataatga    1020
gggaatcata aaagtctttt tcatgtgcac agtgttcttt gcattgggtt tggggaagat    1080
gtaa                                                                 1084
```

<210> SEQ ID NO 21
<211> LENGTH: 155
<212> TYPE: PRT
<213> ORGANISM: Mus sp.
<220> FEATURE:
<223> OTHER INFORMATION: mouse GR06

<400> SEQUENCE: 21

```
Met Leu Thr Val Ala Glu Gly Ile Leu Leu Cys Phe Val Thr Ser Gly
 1               5                  10                  15

Ser Val Leu Gly Val Leu Gly Asn Gly Phe Ile Leu His Ala Asn Tyr
                20                  25                  30

Ile Asn Cys Val Arg Lys Lys Phe Ser Thr Ala Gly Phe Ile Leu Thr
            35                  40                  45

Gly Leu Ala Ile Cys Arg Ile Phe Val Ile Cys Ile Ile Ile Ser Asp
        50                  55                  60

Gly Tyr Leu Lys Leu Phe Ser Pro His Met Val Ala Ser Asp Ala His
    65                  70                  75                  80

Ile Ile Val Ile Ser Tyr Ile Trp Val Ile Asn His Thr Ser Ile
                85                  90                  95

Trp Phe Ala Thr Ser Leu Asn Leu Phe Tyr Leu Leu Lys Ile Ala Asn
                100                 105                 110

Phe Ser His Tyr Ile Phe Phe Cys Leu Lys Arg Arg Ile Asn Thr Val
            115                 120                 125

Phe Ile Phe Leu Leu Gly Cys Leu Phe Ile Ser Trp Ser Ile Ala Phe
        130                 135                 140

Pro Gln Thr Val Lys Ile Phe Asn Val Lys Lys
145                 150                 155
```

<210> SEQ ID NO 22
<211> LENGTH: 538
<212> TYPE: DNA
<213> ORGANISM: Mus sp.
<220> FEATURE:
<223> OTHER INFORMATION: mouse GR06

<400> SEQUENCE: 22

```
ctgcagcagg taaaaaaaaa aaagctaaaa tagttatagt tgcagcagaa gcaacgttag     60
ggatctgtag agatgctgac tgtagcagaa ggaatcctcc tttgttttgt aactagtggt    120
tcagtcctgg gagttctagg aaatggattt atcctgcatg caaactacat taactgtgtc    180
agaaagaagt tctccacagc tggctttatt ctcacaggct ggctatttg cagaatcttt     240 gtcatatgta taataatctc tgatggatat ttaaaattgt ttctccaca tatggttgcc     300 tctgatgccc acattatagt gatttcttac atatgggtaa ttatcaatca tacaagtata    360
tggtttgcca ccagcctcaa cctcttctat ctcctgaaga tagcaaattt ttctcactac    420
atcttcttct gcttgaagag aagaatcaat acagtattta tctttctcct gggatgctta    480
tttatatcat ggtcaattgc tttcccacaa acagtgaaga tatttaatgt taaaaagc      538
```

<210> SEQ ID NO 23
<211> LENGTH: 173
<212> TYPE: PRT

<213> ORGANISM: Mus sp.
<220> FEATURE:
<223> OTHER INFORMATION: mouse GR07

<400> SEQUENCE: 23

```
Asn Ser Ala Glu Gly Ile Leu Leu Cys Val Val Thr Ser Glu Ala Val
1               5                   10                  15

Leu Gly Val Leu Gly Asp Thr Tyr Ile Ala Leu Phe Asn Cys Met Asp
            20                  25                  30

Tyr Ala Lys Asn Lys Leu Ser Lys Ile Gly Phe Ile Leu Ile Gly
        35                  40                  45

Leu Ala Ile Ser Arg Ile Gly Val Val Trp Ile Ile Leu Gln Gly
    50                  55                  60

Tyr Ile Gln Val Phe Phe Pro His Met Leu Thr Ser Gly Asn Ile Thr
65                  70                  75                  80

Glu Tyr Ile Thr Tyr Ile Trp Val Phe Leu Asn His Leu Ser Val Trp
                85                  90                  95

Phe Val Thr Asn Leu Asn Ile Leu Tyr Phe Leu Lys Ile Ala Asn Phe
            100                 105                 110

Ser Asn Ser Val Phe Leu Trp Leu Lys Arg Arg Val Asn Ala Val Phe
        115                 120                 125

Ile Phe Leu Ser Gly Cys Leu Leu Thr Ser Trp Leu Leu Cys Phe Pro
    130                 135                 140

Gln Met Thr Lys Ile Leu Gln Asn Ser Lys Met His Gln Arg Asn Thr
145                 150                 155                 160

Ser Trp Ala Thr Ser Gly Lys Ile Leu Leu Leu Pro Lys
                165                 170
```

<210> SEQ ID NO 24
<211> LENGTH: 520
<212> TYPE: DNA
<213> ORGANISM: Mus sp.
<220> FEATURE:
<223> OTHER INFORMATION: mouse GR07

<400> SEQUENCE: 24

```
gaattcagca gaaggcatcc tcctttgtgt tgtcactagt gaggctgtgc tcggagtttt      60
aggggacaca tatattgcac ttttaactg catggactat gctaagaaca agaagctctc     120
taagatcggt ttcattctca ttggcttggc gatttccaga attggtgttg tatggataat     180
aattttacaa gggtatatac aagtattttt tccacacatg cttacctctg gaaacataac     240
tgaatatatt acttacatat gggtatttct caatcactta agtgtctggt ttgtcaccaa     300
cctcaacatc ctctactttc taaagatagc taatttttcc aactctgtat ttctctggct     360
gaaaaggaga gtcaatgcag tttttatctt tctgtcagga tgcttactta cctcatggtt     420
actatgtttt ccacaaatga caaagatact tcaaaatagt aaaatgcacc agagaaacac     480
atcttgggcc accagcggaa aaatacttct attaccaaag                           520
```

<210> SEQ ID NO 25
<211> LENGTH: 94
<212> TYPE: PRT
<213> ORGANISM: Mus sp.
<220> FEATURE:
<223> OTHER INFORMATION: mouse GR08

<400> SEQUENCE: 25

```
Met Leu Trp Glu Leu Tyr Val Phe Val Phe Ala Ala Ser Val Phe Leu
1               5                   10                  15
```

Asn Phe Val Gly Ile Ile Ala Asn Leu Phe Ile Ile Val Ile Ile
                20                  25                  30

Lys Thr Trp Val Asn Ser Arg Arg Ile Ala Ser Pro Asp Arg Ile Leu
        35                  40                  45

Phe Ser Leu Ala Ile Thr Arg Phe Leu Thr Leu Gly Leu Phe Leu Leu
    50                  55                  60

Asn Ser Val Tyr Ile Ala Thr Asn Thr Gly Arg Ser Ser Leu Leu Phe
65                  70                  75                  80

His Ile Phe Ser Ile Val Leu Glu Val Ser Gly Cys Lys Gln
                85                  90

<210> SEQ ID NO 26
<211> LENGTH: 825
<212> TYPE: DNA
<213> ORGANISM: Mus sp.
<220> FEATURE:
<221> NAME/KEY: modified_base
<222> LOCATION: (1)..(825)
<223> OTHER INFORMATION: mouse GR08
<223> OTHER INFORMATION: n = g, a, c or t

<400> SEQUENCE: 26
ggcattccta agaaaataag aacaggagtg aagaaatagt aatttaatcc ttgaaagatt        60
tgcatctcag taaaagcagc tgcctcttag accagaaatg gtgtttgcca tgctggaaaa      120
taaaaaggag acctctttcc aggctgcatc ctgtgtctgc ttacttattt cagtttgttt      180
tcatcggcac caaacgagga aagatgctct gggaactgta tgtatttgtg tttgctgcct      240
cggttttttt aaattttgta ggaatcattg caaatctatt tattatagtg ataattatta      300
agacttgggt caacagtcgc agaattgcct ctccggatag gatcctgttc agcttggcca      360
tcactagatt cctgactttg gggttgtttc tactgaacag tgtctacatt gctacaaata      420
ctggaaggtc aagtctactt ttccacattt tttctattgt gttggaagtt tctggatgca      480
aacagtctct ggttagtgac cattctgaac agcttgtatt gtgtgaaara tactaatttt      540
caacacccag kgtttcttct gttgaaacgg actatctcta tgaagacccc aacctgctgg      600
tggcctgtct tntganttca accctmccac tcttctatat tatatgctct cacaaawatt      660
nacgttttnc tgaaccataa ttgggagaaa wgacaccgca tttgacctca gngatggnat      720
cttgacgnta gtagcccttt gckgccgaac tccaktwtac atgnnttgtc tgtanntgct      780
cannagggac ctttgcttcc ttgtaaaaca ttcctgggna anaaa                       825

<210> SEQ ID NO 27
<211> LENGTH: 115
<212> TYPE: PRT
<213> ORGANISM: Mus sp.
<220> FEATURE:
<223> OTHER INFORMATION: mouse GR09

<400> SEQUENCE: 27

Met Glu His Leu Leu Lys Arg Thr Phe Asp Ile Thr Glu Asn Ile Leu
1               5                   10                  15

Leu Ile Ile Leu Phe Ile Glu Leu Ile Ile Gly Leu Ile Gly Asn Gly
                20                  25                  30

Phe Thr Ala Leu Val His Cys Met Asp Trp Val Lys Arg Lys Lys Met
        35                  40                  45

Ser Leu Val Asn Lys Ile Leu Thr Ala Leu Ala Thr Ser Arg Ile Phe
    50                  55                  60

```
Leu Leu Trp Phe Met Leu Val Gly Phe Pro Ile Ser Ser Leu Tyr Pro
 65                  70                  75                  80

Tyr Leu Val Thr Thr Arg Leu Met Ile Gln Phe Thr Ser Thr Leu Trp
                 85                  90                  95

Thr Ile Ala Asn His Ile Ser Val Trp Phe Ala Thr Cys Leu Ser Val
            100                 105                 110

Phe Tyr Phe
        115

<210> SEQ ID NO 28
<211> LENGTH: 441
<212> TYPE: DNA
<213> ORGANISM: Mus sp.
<220> FEATURE:
<223> OTHER INFORMATION: mouse GR09

<400> SEQUENCE: 28
gaattcagaa atcatcaaaa aatcttcaaa actacatgtt taaaatagca cttcaaatga    60
atacatttgc aaatctttac aactaataca taaaatggag catcttttga agagaacatt   120
tgatatcacc gagaacatac ttctaattat tttattcatt gaattaataa ttggacttat   180
aggaaacgga ttcacagcct tggtgcactg catggactgg gttaagagaa aaaaaatgtc   240
attagttaat aaaatcctca ccgctttggc aacttctaga attttcctgc tctggttcat   300
gctagtaggt tttccaatta gctcactgta cccatattta gttactacta gactgatgat   360
acagttcact agtactctat ggactatagc taaccatatt agtgtctggt ttgctacatg   420
cctcagtgtc ttttattttc t                                             441

<210> SEQ ID NO 29
<211> LENGTH: 68
<212> TYPE: PRT
<213> ORGANISM: Mus sp.
<220> FEATURE:
<223> OTHER INFORMATION: mouse GR10

<400> SEQUENCE: 29

Met Phe Ser Gln Ile Ile Ser Thr Ser Asp Ile Phe Thr Phe Thr Ile
  1               5                  10                  15

Ile Leu Phe Val Glu Leu Val Ile Gly Ile Leu Gly Asn Gly Phe Ile
             20                  25                  30

Ala Leu Val Asn Ile Met Asp Trp Thr Lys Arg Arg Ser Ile Ser Ser
         35                  40                  45

Ala Asp Gln Ile Leu Thr Ala Leu Ala Ile Thr Arg Phe Leu Tyr Val
     50                  55                  60

Trp Val Met Ile
 65

<210> SEQ ID NO 30
<211> LENGTH: 782
<212> TYPE: DNA
<213> ORGANISM: Mus sp.
<220> FEATURE:
<221> NAME/KEY: modified_base
<222> LOCATION: (1)..(782)
<223> OTHER INFORMATION: mouse GR10
<223> OTHER INFORMATION: n = g, a, c or t

<400> SEQUENCE: 30
ctgcagaatt caacatctta ttcaacttca gaaaactgga tattagacac agtgtctgga    60
tgaagcagag gtgatctctt tgggaaaaaa agccaagtag tcataaagaa tttatgaaac   120
```

```
aattcctggg attgtttata tttgttacaa acaaatttat atgtttgtta gtcagtaatg    180
tataagtggg attttaaagc atgattatct tgaatttttta acaaaaaaca tgtagtgctt    240
tttaaatgta gcagaaacat taaaaattga agcatgttct cacagataat aagcaccagt    300 gatatttttta cttttacaat agatattatt tgtggaatta gtaataggaa ttttaggaaa    360
tggattcata gcactagtga atatcatgga ctggaccaag agaagaagca tttcatcagc    420
ggatcagatt ctcactgctt tggccattac cagatttctc tatgtgtggg ttatgatcat    480
ttgtatattg ttattcatgc tgngcccaca tttgcttacc agatcagaaa tagtnacatc    540
aattggtntt atttggatag ngaataacca tttcagccgt ttggcttgcc ccatgcctcg    600 gggncttttta ttttntgaag atagccaanc tttctaaccc ctttgtttct tttaccctaa    660 aggggggggag gggaaaaaaa gtaagttttt aatggataat tacanggnnt tcaatggatt    720
tttnttggat ttttaaaccc cggttntncn tttaaaccnt ggtnttggac caggntntcc    780 cn                                                                     782
```

<210> SEQ ID NO 31
<211> LENGTH: 126
<212> TYPE: PRT
<213> ORGANISM: Mus sp.
<220> FEATURE:
<223> OTHER INFORMATION: mouse GR11

<400> SEQUENCE: 31

```
Lys Asn Tyr Phe Leu Ile Asn Gln Ser Val Thr Asn Leu Gly Ile Phe
 1               5                  10                  15

Phe Phe Ile Ile Val Ser Leu Ile Thr Cys Phe Leu Leu Ile Val Phe
                20                  25                  30

Leu Trp Arg His Val Arg Gln Met His Ser Asp Val Ser Gly Phe Arg
            35                  40                  45

Asp His Ser Thr Lys Val His Val Lys Ala Met Lys Phe Leu Ile Ser
        50                  55                  60

Phe Met Val Phe Phe Ile Leu His Phe Val Gly Leu Ser Ile Glu Val
 65                  70                  75                  80

Leu Cys Phe Ile Leu Pro Gln Asn Lys Leu Leu Phe Ile Thr Gly Leu
                85                  90                  95

Thr Ala Thr Cys Leu Tyr Pro Cys Gly His Ser Ile Ile Val Ile Leu
            100                 105                 110

Gly Asn Lys Gln Leu Lys Gln Ala Ser Leu Lys Ala Leu Gln
        115                 120                 125
```

<210> SEQ ID NO 32
<211> LENGTH: 380
<212> TYPE: DNA
<213> ORGANISM: Mus sp.
<220> FEATURE:
<223> OTHER INFORMATION: mouse GR11

<400> SEQUENCE: 32

```
ggaaaaatta ctttcttatt aaccaaagtg tgaccaatct gggaatcttt ttcttcatta     60
ttgtatccct gattacctgc tttctgttga ttgttttcct ctggagacat gtcagacaaa    120
tgcactcaga tgtttcagga ttcagagacc acagcacaaa agtacatgtg aaagctatga    180
aatttctaat atcttttatg gtcttcttta ttctgcattt tgtaggcctt tccatagaag    240
tgctatgctt tattctgcca caaaataaac tgctctttat aactggtttg acagccacat    300
```

```
gcctctatcc ctgcggtcac tcaatcatcg taattttagg aaataagcag ttaaagcaag      360
cctctttgaa ggcactgcag                                                  380
```

<210> SEQ ID NO 33
<211> LENGTH: 180
<212> TYPE: PRT
<213> ORGANISM: Mus sp.
<220> FEATURE:
<223> OTHER INFORMATION: mouse GR13

<400> SEQUENCE: 33

```
Glu Phe Ile Met Gly Thr Leu Gly Asn Gly Phe Ile Phe Leu Ile Val
  1               5                  10                  15

Cys Ile Asp Trp Val Gln Arg Arg Lys Ile Ser Leu Val Asp Gln Ile
             20                  25                  30

Arg Thr Ala Leu Ala Ile Ser Arg Ile Ala Leu Ile Trp Leu Ile Phe
         35                  40                  45

Leu Asp Trp Trp Val Ser Val His Tyr Pro Ala Leu His Glu Thr Gly
     50                  55                  60

Lys Met Leu Ser Thr Tyr Leu Ile Ser Trp Thr Val Ile Asn His Cys
 65                  70                  75                  80

Asn Phe Trp Leu Thr Ala Asn Leu Ser Ile Leu Tyr Phe Leu Lys Ile
                 85                  90                  95

Ala Asn Phe Ser Asn Ile Ile Phe Leu Tyr Leu Lys Phe Arg Ser Lys
            100                 105                 110

Asn Val Val Leu Val Thr Leu Leu Ala Ser Leu Phe Phe Leu Phe Leu
        115                 120                 125

Asn Thr Val Ile Ile Lys Ile Phe Ser Asp Val Cys Phe Asp Ser Val
    130                 135                 140

Gln Arg Asn Val Ser Gln Ile Phe Ile Met Tyr Asn His Glu Gln Ile
145                 150                 155                 160

Cys Lys Phe Leu Ser Phe Thr Asn Pro Met Phe Thr Phe Ile Pro Phe
                165                 170                 175

Val Tyr Val His
            180
```

<210> SEQ ID NO 34
<211> LENGTH: 540
<212> TYPE: DNA
<213> ORGANISM: Mus sp.
<220> FEATURE:
<223> OTHER INFORMATION: mouse GR13

<400> SEQUENCE: 34

```
gaattcataa tgggaacctt aggaaatgga ttcatttttc tgatagtctg catagactgg      60
gtccaaagaa gaaaatctc tttagtggat caaatccgca ctgctctggc aattagcaga      120
atcgctctaa tttggttgat attcctagat tggtgggtgt ctgttcatta cccagcatta     180
catgaaactg gtaagatgtt atcaacatat ttgatttcct ggacggtgat caatcattgt     240 aactttggc ttactgcaaa cttgagcatc ctttattttc tcaagatagc caacttttct      300
aacattattt ttctttatct aaagtttaga tctaaaaatg tggtattagt gaccctgtta     360
gcgtctctat ttttcttgtt cttaaatact gtaattataa aaatattttc tgatgtgtgt    420
tttgatagtg ttcaaagaaa tgtgtctcaa atttcataa tgtataacca tgaacaaatt      480
tgcaaatttc tttcctttac taaccctatg ttcacattca tacctttgt ttatgtccac      540
```

<210> SEQ ID NO 35
<211> LENGTH: 299
<212> TYPE: PRT
<213> ORGANISM: Homo sapiens
<220> FEATURE:
<223> OTHER INFORMATION: human GR01, Sf01

<400> SEQUENCE: 35

```
Met Leu Glu Ser His Leu Ile Ile Tyr Phe Leu Leu Ala Val Ile Gln
 1               5                  10                  15

Phe Leu Leu Gly Ile Phe Thr Asn Gly Ile Val Val Val Asn Gly
             20                  25                  30

Ile Asp Leu Ile Lys His Arg Lys Met Ala Pro Leu Asp Leu Leu Leu
         35                  40                  45

Ser Cys Leu Ala Val Ser Arg Ile Phe Leu Gln Leu Phe Ile Phe Tyr
     50                  55                  60

Val Asn Val Ile Val Ile Phe Phe Ile Glu Phe Ile Met Cys Ser Ala
 65                  70                  75                  80

Asn Cys Ala Ile Leu Leu Phe Ile Asn Glu Leu Glu Leu Trp Leu Ala
                 85                  90                  95

Thr Trp Leu Gly Val Phe Tyr Cys Ala Lys Val Ala Ser Val Arg His
            100                 105                 110

Pro Leu Phe Ile Trp Leu Lys Met Arg Ile Ser Lys Leu Val Pro Trp
        115                 120                 125

Met Ile Leu Gly Ser Leu Leu Tyr Val Ser Met Ile Cys Val Phe His
    130                 135                 140

Ser Lys Tyr Ala Gly Phe Met Val Pro Tyr Phe Leu Arg Lys Phe Phe
145                 150                 155                 160

Ser Gln Asn Ala Thr Ile Gln Lys Glu Asp Thr Leu Ala Ile Gln Ile
                165                 170                 175

Phe Ser Phe Val Ala Glu Phe Ser Val Pro Leu Leu Ile Phe Leu Phe
            180                 185                 190

Ala Val Leu Leu Leu Ile Phe Ser Leu Gly Arg His Thr Arg Gln Met
        195                 200                 205

Arg Asn Thr Val Ala Gly Ser Arg Val Pro Gly Arg Gly Ala Pro Ile
    210                 215                 220

Ser Ala Leu Leu Ser Ile Leu Ser Phe Leu Ile Leu Tyr Phe Ser His
225                 230                 235                 240

Cys Met Ile Lys Val Phe Leu Ser Ser Leu Lys Phe His Ile Arg Arg
                245                 250                 255

Phe Ile Phe Leu Phe Phe Ile Leu Val Ile Gly Ile Tyr Pro Ser Gly
            260                 265                 270

His Ser Leu Ile Leu Ile Leu Gly Asn Pro Lys Leu Lys Gln Asn Ala
        275                 280                 285

Lys Lys Phe Leu Leu His Ser Lys Cys Cys Gln
    290                 295
```

<210> SEQ ID NO 36
<211> LENGTH: 900
<212> TYPE: DNA
<213> ORGANISM: Homo sapiens
<220> FEATURE:
<223> OTHER INFORMATION: human GR01, Sf01

<400> SEQUENCE: 36

```
atgctagagt ctcacctcat tatctatttt cttcttgcag tgatacaatt tcttcttggg      60
attttcacaa atggcatcat tgtggtggtg aatggcattg acttgatcaa gcacagaaaa     120
```

-continued

```
atggctccgc tggatctcct tctttcttgt ctggcagttt ctagaatttt tctgcagttg    180
ttcatcttct acgttaatgt gattgttatc ttcttcatag aattcatcat gtgttctgcg    240
aattgtgcaa ttctcttatt tataaatgaa ttggaacttt ggcttgccac atggctcggc    300
gttttctatt gtgccaaggt tgccagcgtc cgtcacccac tcttcatctg gttgaagatg    360
aggatatcca agctggtccc atggatgatc ctggggtctc tgctatatgt atctatgatt    420
tgtgttttcc atagcaaata tgcagggttt atggtcccat acttcctaag gaaattttc    480 tcccaaaatg ccacaattca aaagaagat acactggcta tacagatttt ctcttttgtt    540
gctgagttct cagtgccatt gcttatcttc cttttgctg ttttgctctt gattttctct    600
ctggggaggc acaccggca atgagaaac acagtggccg gcagcagggt tcctggcagg    660
ggtgcaccca tcagcgcgtt gctgtctatc ctgtccttcc tgatcctcta cttctcccac    720
tgcatgataa agttttttct ctcttctcta agtttcaca tcagaaggtt catctttctg    780
ttcttcatcc ttgtgattgg tatatacct tctggacact ctctcatctt aattttagga    840
aatcctaaat tgaaacaaaa tgcaaaaaag ttcctcctcc acagtaagtg ctgtcagtga    900
```

<210> SEQ ID NO 37
<211> LENGTH: 302
<212> TYPE: PRT
<213> ORGANISM: Homo sapiens
<220> FEATURE:
<221> NAME/KEY: MOD_RES
<222> LOCATION: (143)
<223> OTHER INFORMATION: human GR02
<223> OTHER INFORMATION: Xaa = any amino acid

<400> SEQUENCE: 37

```
Met Ala Leu Ser Phe Ser Ala Ile Leu His Ile Ile Met Met Ser Ala
 1               5                  10                  15

Glu Phe Phe Thr Gly Ile Thr Val Asn Gly Phe Leu Ile Ile Val Asn
             20                  25                  30

Cys Asn Glu Leu Ile Lys His Arg Lys Leu Met Pro Ile Gln Ile Leu
         35                  40                  45

Leu Met Cys Ile Gly Met Ser Arg Phe Gly Leu Gln Met Val Leu Met
     50                  55                  60

Val Gln Ser Phe Phe Ser Val Phe Phe Pro Leu Leu Tyr Val Lys Ile
 65                  70                  75                  80

Ile Tyr Gly Ala Ala Met Met Phe Leu Trp Met Phe Ser Ser Ile
                 85                  90                  95

Ser Leu Trp Phe Ala Thr Cys Leu Ser Val Phe Tyr Cys Leu Lys Ile
            100                 105                 110

Ser Gly Phe Thr Gln Ser Cys Phe Leu Trp Leu Lys Phe Arg Ile Pro
        115                 120                 125

Lys Leu Ile Pro Trp Leu Phe Trp Glu Ala Phe Trp Pro Leu Xaa Ala
    130                 135                 140

Leu His Leu Cys Val Glu Val Asp Tyr Ala Lys Asn Val Glu Glu Asp
145                 150                 155                 160

Ala Leu Arg Asn Thr Thr Leu Lys Lys Ser Lys Thr Lys Ile Lys Lys
                165                 170                 175

Ile Ser Glu Val Leu Leu Val Asn Leu Ala Leu Ile Phe Pro Leu Ala
            180                 185                 190

Ile Phe Val Met Cys Thr Ser Met Leu Leu Ile Ser Leu Tyr Lys His
        195                 200                 205
```

-continued

```
Thr His Arg Met Gln His Gly Ser His Gly Phe Arg Asn Ala Asn Thr
    210                 215                 220

Glu Ala His Ile Asn Ala Leu Lys Thr Val Ile Thr Phe Phe Cys Phe
225                 230                 235                 240

Phe Ile Ser Tyr Phe Ala Ala Phe Met Thr Asn Met Thr Phe Ser Leu
                245                 250                 255

Pro Tyr Arg Ser His Gln Phe Phe Met Leu Lys Asp Ile Met Ala Ala
            260                 265                 270

Tyr Pro Ser Gly His Ser Val Ile Ile Leu Ser Asn Ser Lys Phe
        275                 280                 285

Gln Gln Ser Phe Arg Arg Ile Leu Cys Leu Lys Lys Lys Leu
    290                 295                 300

<210> SEQ ID NO 38
<211> LENGTH: 910
<212> TYPE: DNA
<213> ORGANISM: Homo sapiens
<220> FEATURE:
<223> OTHER INFORMATION: human GR02

<400> SEQUENCE: 38
atggccttgt cttttcagc tattcttcat attatcatga tgtcagcaga attcttcaca      60
gggatcacag taaatggatt tcttatcatt gttaactgta atgaattgat caaacataga    120
aagctaatgc caattcaaat cctcttaatg tgcataggga tgtctagatt tggtctgcag    180
atggtgttaa tggtacaaag ttttttctct gtgttctttc cactcccttta cgtcaaaata    240
atttatggtg cagcaatgat gttcctttgg atgtttttta gctctatcag cctatggttt    300
gccacttgcc tttctgtatt ttactgcctc aagatttcag gcttcactca gtcctgtttt    360
ctttggttga aattcaggat cccaaagtta ataccttggc tgcttctggg aagcgttctg    420
gcctctgtga gcattgcatc tgtgtgtcga ggtagattac gctaaaaatg tggaagagga    480
tgccctcaga acaccacac taaaaagag taaacaaag ataagaaaa ttagtgaagt        540
gcttcttgtc aacttggcat taatatttcc tctagccata tttgtgatgt gcacttctat    600
gttactcatc tctctttaca agcacactca tcggatgcaa catggatctc atggctttag    660
aaatgccaac acagaagccc atataaatgc attaaaaaca gtgataacat tcttttgctt    720
ctttattct tattttgctg ccttcatgac aaatatgaca tttagtttac cttacagaag     780
tcaccagttc tttatgctga aggacataat ggcagcatat ccctctggcc actcggttat   840
aataatcttg agtaattcta agttccaaca atcatttaga gaattctct gcctcaaaaa    900
gaaactatga                                                           910

<210> SEQ ID NO 39
<211> LENGTH: 316
<212> TYPE: PRT
<213> ORGANISM: Homo sapiens
<220> FEATURE:
<223> OTHER INFORMATION: human GR03

<400> SEQUENCE: 39

Met Met Gly Leu Thr Glu Gly Val Phe Leu Ile Leu Ser Gly Thr Gln
1               5                   10                  15

Phe Thr Leu Gly Ile Leu Val Asn Cys Phe Ile Glu Leu Val Asn Gly
            20                  25                  30

Ser Ser Trp Phe Lys Thr Lys Arg Met Ser Leu Ser Asp Phe Ile Ile
        35                  40                  45
```

```
Thr Thr Leu Ala Leu Leu Arg Ile Ile Leu Leu Cys Ile Ile Leu Thr
     50                  55                  60
Asp Ser Phe Leu Ile Glu Phe Ser Pro Asn Thr His Asp Ser Gly Ile
 65                  70                  75                  80
Ile Met Gln Ile Ile Asp Val Ser Trp Thr Phe Thr Asn His Leu Ser
                 85                  90                  95
Ile Trp Leu Ala Thr Cys Leu Gly Val Leu Tyr Cys Leu Lys Ile Ala
                100                 105                 110
Ser Phe Ser His Pro Thr Phe Leu Trp Leu Lys Trp Arg Val Ser Arg
            115                 120                 125
Val Met Val Trp Met Leu Leu Gly Ala Leu Leu Leu Ser Cys Gly Ser
        130                 135                 140
Thr Ala Ser Leu Ile Asn Glu Phe Lys Leu Tyr Ser Val Phe Arg Gly
145                 150                 155                 160
Ile Glu Ala Thr Arg Asn Val Thr Glu His Phe Arg Lys Arg Ser
                165                 170                 175
Glu Tyr Tyr Leu Ile His Val Leu Gly Thr Leu Trp Tyr Leu Pro Pro
                180                 185                 190
Leu Ile Val Ser Leu Ala Ser Tyr Ser Leu Leu Ile Phe Ser Leu Gly
                195                 200                 205
Arg His Thr Arg Gln Met Leu Gln Asn Gly Thr Ser Ser Arg Asp Pro
        210                 215                 220
Thr Thr Glu Ala His Lys Arg Ala Ile Arg Ile Leu Ser Phe Phe
225                 230                 235                 240
Phe Leu Phe Leu Leu Tyr Phe Leu Ala Phe Leu Ile Ala Ser Phe Gly
                245                 250                 255
Asn Phe Leu Pro Lys Thr Lys Met Ala Lys Met Ile Gly Glu Val Met
                260                 265                 270
Thr Met Phe Tyr Pro Ala Gly His Ser Phe Ile Leu Ile Leu Gly Asn
                275                 280                 285
Ser Lys Leu Lys Gln Thr Phe Val Val Met Leu Arg Cys Glu Ser Gly
            290                 295                 300
His Leu Lys Pro Gly Ser Lys Gly Pro Ile Phe Ser
305                 310                 315

<210> SEQ ID NO 40
<211> LENGTH: 951
<212> TYPE: DNA
<213> ORGANISM: Homo sapiens
<220> FEATURE:
<223> OTHER INFORMATION: human GR03

<400> SEQUENCE: 40
atgatgggac tcaccgaggg ggtgttcctg attctgtctg gcactcagtt cacactggga      60
attctggtca attgtttcat tgagttggtc aatggtagca gctggttcaa gaccaagaga     120
atgtctttgt ctgacttcat catcaccacc ctggcactct gaggatcat tctgctgtgt     180
attatcttga ctgatagttt tttaatagaa ttctctccca acacacatga ttcagggata     240
ataatgcaaa ttattgatgt tcctggaca tttacaaacc atctgagcat tggcttgcc      300
acctgtcttg gtgtcctcta ctgcctgaaa atcgccagtt tctctcaccc cacattcctc     360
tggctcaagt ggagagtttc tagggtgatg gtatggatgc tgttgggtgc actgctctta     420
tcctgtggta gtaccgcatc tctgatcaat gagtttaagc tctattctgt ctttagggga     480
attgaggcca ccaggaatgt gactgaacac ttcagaaaga agaggagtga gtattatctg     540
```

```
atccatgttc ttgggactct gtggtacctg cctcccttaa ttgtgtccct ggcctcctac    600
tctttgctca tcttctccct ggggaggcac acacggcaga tgctgcaaaa tgggacaagc    660
tccagagatc caaccactga ggcccacaag agggccatca gaatcatcct ttccttcttc    720
tttctcttct tactttactt tcttgctttc ttaattgcat catttggtaa tttcctacca    780
aaaaccaaga tggctaagat gattggcgaa gtaatgacaa tgttttatcc tgctggccac    840
tcatttattc tcattctggg gaacagtaag ctgaagcaga catttgtagt gatgctccgg    900
tgtgagtctg tcatctgaa gcctggatcc aagggaccca ttttctctta g              951
```

<210> SEQ ID NO 41
<211> LENGTH: 299
<212> TYPE: PRT
<213> ORGANISM: Homo sapiens
<220> FEATURE:
<223> OTHER INFORMATION: human GR04

<400> SEQUENCE: 41

| Met | Leu | Arg | Leu | Phe | Tyr | Phe | Ser | Ala | Ile | Ile | Ala | Ser | Val | Ile | Leu |
|---|---|---|---|---|---|---|---|---|---|---|---|---|---|---|---|
| 1 | | | | 5 | | | | | 10 | | | | | 15 | |

| Asn | Phe | Val | Gly | Ile | Ile | Met | Asn | Leu | Phe | Ile | Thr | Val | Val | Asn | Cys |
| | | | 20 | | | | | 25 | | | | | 30 | | |

| Lys | Thr | Trp | Val | Lys | Ser | His | Arg | Ile | Ser | Ser | Ser | Asp | Arg | Ile | Leu |
| | | 35 | | | | | 40 | | | | | 45 | | | |

| Phe | Ser | Leu | Gly | Ile | Thr | Arg | Phe | Leu | Met | Leu | Gly | Leu | Phe | Leu | Val |
| 50 | | | | | 55 | | | | | 60 | | | | | |

| Asn | Thr | Ile | Tyr | Phe | Val | Ser | Ser | Asn | Thr | Glu | Arg | Ser | Val | Tyr | Leu |
| 65 | | | | 70 | | | | | 75 | | | | | 80 | |

| Ser | Ala | Phe | Phe | Val | Leu | Cys | Phe | Met | Phe | Leu | Asp | Ser | Ser | Ser | Val |
| | | | | 85 | | | | | 90 | | | | | 95 | |

| Trp | Phe | Val | Thr | Leu | Leu | Asn | Ile | Leu | Tyr | Cys | Val | Lys | Ile | Thr | Asn |
| | | | 100 | | | | | 105 | | | | | 110 | | |

| Phe | Gln | His | Ser | Val | Phe | Leu | Leu | Leu | Lys | Arg | Asn | Ile | Ser | Pro | Lys |
| | | | 115 | | | | | 120 | | | | | 125 | | |

| Ile | Pro | Arg | Leu | Leu | Leu | Ala | Cys | Val | Leu | Ile | Ser | Ala | Phe | Thr | Thr |
| 130 | | | | | 135 | | | | | 140 | | | | | |

| Cys | Leu | Tyr | Ile | Thr | Leu | Ser | Gln | Ala | Ser | Pro | Phe | Pro | Glu | Leu | Val |
| 145 | | | | | 150 | | | | | 155 | | | | | 160 |

| Thr | Thr | Arg | Asn | Asn | Thr | Ser | Phe | Asn | Ile | Ser | Glu | Gly | Ile | Leu | Ser |
| | | | | 165 | | | | | 170 | | | | | 175 | |

| Leu | Val | Val | Ser | Leu | Val | Leu | Ser | Ser | Ser | Leu | Gln | Phe | Ile | Ile | Asn |
| | | | 180 | | | | | 185 | | | | | 190 | | |

| Val | Thr | Ser | Ala | Ser | Leu | Leu | Ile | His | Ser | Leu | Arg | Arg | His | Ile | Gln |
| | | | | 195 | | | | | 200 | | | | | 205 | |

| Lys | Met | Gln | Lys | Asn | Ala | Thr | Gly | Phe | Trp | Asn | Pro | Gln | Thr | Glu | Ala |
| | | | 210 | | | | | 215 | | | | | 220 | | |

| His | Val | Gly | Ala | Met | Lys | Leu | Met | Val | Tyr | Phe | Leu | Ile | Leu | Tyr | Ile |
| 225 | | | | | 230 | | | | | 235 | | | | | 240 |

| Pro | Tyr | Ser | Val | Ala | Thr | Leu | Val | Gln | Tyr | Leu | Pro | Phe | Tyr | Ala | Gly |
| | | | | 245 | | | | | 250 | | | | | 255 | |

| Met | Asp | Met | Gly | Thr | Lys | Ser | Ile | Cys | Leu | Ile | Phe | Ala | Thr | Leu | Tyr |
| | | | 260 | | | | | 265 | | | | | 270 | | |

| Ser | Pro | Gly | His | Ser | Val | Leu | Ile | Ile | Ile | Thr | His | Pro | Lys | Leu | Lys |
| | | | | 275 | | | | | 280 | | | | | 285 | |

| Thr | Thr | Ala | Lys | Lys | Ile | Leu | Cys | Phe | Lys | Lys |
| | | | 290 | | | | | 295 | | |

-continued

```
       290                295
```

<210> SEQ ID NO 42
<211> LENGTH: 900
<212> TYPE: DNA
<213> ORGANISM: Homo sapiens
<220> FEATURE:
<223> OTHER INFORMATION: human GR04

<400> SEQUENCE: 42

```
atgcttcggt tattctattt ctctgctatt attgcctcag ttatttaaa ttttgtagga      60
atcattatga atctgtttat tacagtggtc aattgcaaaa cttgggtcaa aagccataga    120
atctcctctt ctgataggat tctgttcagc ctgggcatca ccaggtttct tatgctggga    180
ctatttctgg tgaacaccat ctacttcgtc tcttcaaata cggaaaggtc agtctacctg    240
tctgctttt ttgtgttgtg tttcatgttt ttggactcga gcagtgtctg gtttgtgacc    300
ttgctcaata tcttgtactg tgtgaagatt actaacttcc aacactcagt gtttctcctg    360
ctgaagcgga atatctcccc aaagatcccc aggctgctgc tggcctgtgt gctgatttct    420
gctttcacca cttgcctgta catcacgctt agccaggcat caccttttcc tgaacttgtg    480
actacgagaa ataacacatc atttaatatc agtgagggca tcttgtcttt agtggtttct    540
ttggtcttga gctcatctct ccagttcatc attaatgtga cttctgcttc cttgctaata    600
cactccttga ggagacatat acagaagatg cagaaaaatg ccactggttt ctggaatccc    660
cagacggaag ctcatgtagg tgctatgaag ctgatggtct atttcctcat cctctacatt    720
ccatattcag ttgctaccct ggtccagtat ctccccttt atgcagggat ggatatgggg    780
accaaatcca tttgtctgat ttttgccacc ctttactctc caggacattc tgttctcatt    840
attatcacac atcctaaact gaaacaaca gcaagaaga ttctttgttt caaaaaatag    900
```

<210> SEQ ID NO 43
<211> LENGTH: 299
<212> TYPE: PRT
<213> ORGANISM: Homo sapiens
<220> FEATURE:
<223> OTHER INFORMATION: human GR05

<400> SEQUENCE: 43

```
Met Leu Ser Ala Gly Leu Gly Leu Leu Met Leu Val Ala Val Val Glu
 1               5                  10                  15

Phe Leu Ile Gly Leu Ile Gly Asn Gly Ser Leu Val Val Trp Ser Phe
            20                  25                  30

Arg Glu Trp Ile Arg Lys Phe Asn Trp Ser Ser Tyr Asn Leu Ile Ile
        35                  40                  45

Leu Gly Leu Ala Gly Cys Arg Phe Leu Leu Gln Trp Leu Ile Ile Leu
    50                  55                  60

Asp Leu Ser Leu Phe Pro Leu Phe Gln Ser Ser Arg Trp Leu Arg Tyr
65                  70                  75                  80

Leu Ser Ile Phe Trp Val Leu Ser Gln Ala Ser Leu Trp Phe Ala
            85                  90                  95

Thr Phe Leu Ser Val Phe Tyr Cys Lys Lys Ile Thr Thr Phe Asp Arg
           100                 105                 110

Pro Ala Tyr Leu Trp Leu Lys Gln Arg Ala Tyr Asn Leu Ser Leu Trp
       115                 120                 125

Cys Leu Leu Gly Tyr Phe Ile Ile Asn Leu Leu Leu Thr Val Gln Ile
   130                 135                 140
```

```
Gly Leu Thr Phe Tyr His Pro Pro Gln Gly Asn Ser Ser Ile Arg Tyr
145                 150                 155                 160

Pro Phe Glu Ser Trp Gln Tyr Leu Tyr Ala Phe Gln Leu Asn Ser Gly
            165                 170                 175

Ser Tyr Leu Pro Leu Val Val Phe Leu Val Ser Ser Gly Met Leu Ile
        180                 185                 190

Val Ser Leu Tyr Thr His His Lys Lys Met Lys Val His Ser Ala Gly
        195                 200                 205

Arg Arg Asp Val Arg Ala Lys Ala His Ile Thr Ala Leu Lys Ser Leu
        210                 215                 220

Gly Cys Phe Leu Leu Leu His Leu Val Tyr Ile Met Ala Ser Pro Phe
225                 230                 235                 240

Ser Ile Thr Ser Lys Thr Tyr Pro Pro Asp Leu Thr Ser Val Phe Ile
            245                 250                 255

Trp Glu Thr Leu Met Ala Ala Tyr Pro Ser Leu His Ser Leu Ile Leu
            260                 265                 270

Ile Met Gly Ile Pro Arg Val Lys Gln Thr Cys Gln Lys Ile Leu Trp
        275                 280                 285

Lys Thr Val Cys Ala Arg Arg Cys Trp Gly Pro
        290                 295

<210> SEQ ID NO 44
<211> LENGTH: 900
<212> TYPE: DNA
<213> ORGANISM: Homo sapiens
<220> FEATURE:
<223> OTHER INFORMATION: human GR05

<400> SEQUENCE: 44
atgctgagcg ctggcctagg actgctgatg ctggtggcag tggttgaatt tctcatcggt      60
ttaattggaa atggaagcct ggtggtctgg agttttagag aatggatcag aaaattcaac     120
tggtcctcat ataacctcat tatcctgggc ctggctggct gccgatttct cctgcagtgg     180
ctgatcattt tggacttaag cttgttttcca ctttttccaga gcagccgttg gcttcgctat     240
cttagtatct tctgggtcct ggtaagccag gccagcttat ggtttgccac cttcctcagt     300
gtcttctatt gcaagaagat cacgaccttc gatcgcccgg cctacttgtg gctgaagcag     360
agggcctata acctgagtct ctggtgcctt ctgggctact ttataatcaa tttgttactt     420
acagtccaaa ttggcttaac attctatcat cctccccaag aaacagcag cattcggtat     480 ccctttgaaa gctggcagta cctgtatgca tttcagctca attcaggaag ttatttgcct     540
ttagtggtgt tcttgttttc ctctgggatg ctgattgtct ctttgtatac acaccacaag     600
aagatgaagg tccattcagc tggtaggagg gatgtccggg ccaaggctca catcactgcg     660
ctgaagtcct gggctgctt cctcttactt cacctggttt atatcatggc cagccccttc     720
tccatcacct ccaagactta tcctcctgat ctcaccagtg tcttcatctg ggagacactc     780
atggcagcct atccttctct tcattctctc atattgatca tggggattcc tagggtgaag     840
cagacttgtc agaagatcct gtggaagaca gtgtgtgctc ggagatgctg ggcccatga     900

<210> SEQ ID NO 45
<211> LENGTH: 286
<212> TYPE: PRT
<213> ORGANISM: Homo sapiens
<220> FEATURE:
<221> NAME/KEY: MOD_RES
<222> LOCATION: (1)..(286)
<223> OTHER INFORMATION: human GR06
```

<223> OTHER INFORMATION: Xaa = any amino acid

<400> SEQUENCE: 45

```
Met Leu Ala Ala Ala Leu Gly Leu Leu Met Pro Ile Ala Gly Ala Glu
 1               5                  10                  15
Phe Leu Ile Gly Leu Val Gly Asn Gly Val Pro Val Val Cys Ser Phe
             20                  25                  30
Arg Gly Trp Val Lys Lys Met Xaa Gly Val Pro Ile Asn Ser His Asp
         35                  40                  45
Ser Gly Lys Xaa Pro Leu Ser Pro Thr Gln Ala Asp His Val Gly His
     50                  55                  60
Lys Ser Val Ser Thr Phe Pro Glu Gln Trp Leu Ala Leu Leu Ser Xaa
 65                  70                  75                  80
Cys Leu Arg Val Leu Val Ser Gln Ala Asn Met Xaa Phe Ala Thr Phe
                 85                  90                  95
Phe Ser Gly Phe Cys Cys Met Glu Ile Met Thr Phe Val Xaa Xaa Xaa
            100                 105                 110
Xaa Xaa Xaa Xaa Xaa Xaa Xaa Xaa Xaa Xaa Xaa Xaa Xaa Xaa Xaa Xaa
            115                 120                 125
Xaa Leu Leu Val Ser Phe Lys Ile Thr Phe Tyr Phe Ser Ala Leu Val
130                 135                 140
Gly Trp Thr Leu Xaa Lys Pro Leu Thr Gly Asn Ser Asn Ile Leu His
145                 150                 155                 160
Pro Ile Leu Asn Leu Leu Phe Leu Xaa Ile Ala Val Gln Xaa Arg Arg
                165                 170                 175
Leu Ile Ala Ile Cys Asp Val Ser Val Pro Leu Val Phe Leu Xaa Arg
            180                 185                 190
His His Arg Lys Met Glu Asp His Thr Ala Val Arg Arg Leu Lys
            195                 200                 205
Pro Arg Xaa Xaa Xaa Xaa Xaa Xaa Xaa Xaa Xaa Xaa Xaa Xaa Xaa
        210                 215                 220
Xaa Leu Tyr Met Val Ser Ala Leu Ala Arg His Phe Ser Met Thr Phe
225                 230                 235                 240
Xaa Ser Pro Ser Asp Leu Thr Ile Leu Ala Ile Ser Ala Thr Leu Met
                245                 250                 255
Ala Val Tyr Thr Ser Phe Pro Ser Ile Val Met Val Met Arg Asn Gln
            260                 265                 270
Thr Cys Gln Arg Ile Leu Glu Met Ile Cys Thr Trp Lys Ser
        275                 280                 285
```

<210> SEQ ID NO 46
<211> LENGTH: 823
<212> TYPE: DNA
<213> ORGANISM: Homo sapiens
<220> FEATURE:
<223> OTHER INFORMATION: human GR06

<400> SEQUENCE: 46

| | | |
|---|---|---|
| atgttggcgg ctgccctagg attgctgatg cccattgcag ggctgaatt tctcattggc | 60 |
| ctggttggaa atggagtccc tgtggtctgc agttttagag atgggtcaa aaaaatgtaa | 120 |
| ggagtcccta taaattctca tgattctggt aagtagccac tttctcctac tcaggccgat | 180 |
| catgttggac ataagtctgt ttccactttc ccagagcagt ggttggcttt actatcttaa | 240 |
| tgtcttcgag tcctggtaag ccaggccaac atgtagtttg ccactttctt cagtggcttc | 300 |
| tgctgcatgg agatcatgac ctttgtcccg ctgacttctt gtagctgaaa agactgggtt | 360 |

```
tttgttttttt gctagtgtct ttcaagatca cttttttattt ctcagctctt gttggctgga    420 cccttttaaaa acccttaaca ggaaacagca acatcctgca tcccatttta aatctgttat    480
ttttatagat tgctgtccag tgaaggagac tgattgctat tgtgatgtt tctgttccac      540 ttgtcttttt gtaaagacat cacaggaaga tggaggacca cacagctgtc aggaggaggc    600
tcaaaccaag gtgctcatcg ctctgaactt ccccctttac atggtttctg ccttggccag    660 acactttttcc atgaccttct aatctccctc tgatctcacc attcttgcca tctctgcaac    720
actcatggct gttatactt catttccgtc tattgtaatg gttatgagga atcagacttg      780
tcagagaatt ctgtaggaga tgatatgtac atggaaatcc tag                      823
```

<210> SEQ ID NO 47
<211> LENGTH: 318
<212> TYPE: PRT
<213> ORGANISM: Homo sapiens
<220> FEATURE:
<223> OTHER INFORMATION: human GR07

<400> SEQUENCE: 47

```
Met Ala Asp Lys Val Gln Thr Thr Leu Leu Phe Leu Ala Val Gly Glu
  1               5                  10                  15

Phe Ser Val Gly Ile Leu Gly Asn Ala Phe Ile Gly Leu Val Asn Cys
             20                  25                  30

Met Asp Trp Val Lys Lys Arg Lys Ile Ala Ser Ile Asp Leu Ile Leu
         35                  40                  45

Thr Ser Leu Ala Ile Ser Arg Ile Cys Leu Leu Cys Val Ile Leu Leu
     50                  55                  60

Asp Cys Phe Ile Leu Val Leu Tyr Pro Asp Val Tyr Ala Thr Gly Lys
 65                  70                  75                  80

Glu Met Arg Ile Ile Asp Phe Phe Trp Thr Leu Thr Asn His Leu Ser
                 85                  90                  95

Ile Trp Phe Ala Thr Cys Leu Ser Ile Tyr Tyr Phe Phe Lys Ile Gly
            100                 105                 110

Asn Phe Phe His Pro Leu Phe Leu Trp Met Lys Trp Arg Ile Asp Arg
        115                 120                 125

Val Ile Ser Trp Ile Leu Leu Gly Cys Val Val Leu Ser Val Phe Ile
    130                 135                 140

Ser Leu Pro Ala Thr Glu Asn Leu Asn Ala Asp Phe Arg Phe Cys Val
145                 150                 155                 160

Lys Ala Lys Arg Lys Thr Asn Leu Thr Trp Ser Cys Arg Val Asn Lys
                165                 170                 175

Thr Gln His Ala Ser Thr Lys Leu Phe Leu Asn Leu Ala Thr Leu Leu
            180                 185                 190

Pro Phe Cys Val Cys Leu Met Ser Phe Phe Leu Leu Ile Leu Ser Leu
        195                 200                 205

Arg Arg His Ile Arg Arg Met Gln Leu Ser Ala Thr Gly Cys Arg Asp
    210                 215                 220

Pro Ser Thr Glu Ala His Val Arg Ala Leu Lys Ala Val Ile Ser Phe
225                 230                 235                 240

Leu Leu Leu Phe Ile Ala Tyr Tyr Leu Ser Phe Leu Ile Ala Thr Ser
                245                 250                 255

Ser Tyr Phe Met Pro Glu Thr Glu Leu Ala Val Ile Phe Gly Glu Ser
            260                 265                 270

Ile Ala Leu Ile Tyr Pro Ser Ser His Ser Phe Ile Leu Ile Leu Gly
```

```
                    275                 280                 285
Asn Asn Lys Leu Arg His Ala Ser Leu Lys Val Ile Trp Lys Val Met
        290                 295                 300

Ser Ile Leu Lys Gly Arg Lys Phe Gln Gln His Lys Gln Ile
305                 310                 315

<210> SEQ ID NO 48
<211> LENGTH: 954
<212> TYPE: DNA
<213> ORGANISM: Homo sapiens
<220> FEATURE:
<223> OTHER INFORMATION: human GR07

<400> SEQUENCE: 48
atggcagata aagtgcagac tactttattg ttcttagcag ttggagagtt ttcagtgggg      60
atcttaggga atgcattcat tggattggta aactgcatgg actgggtcaa gaagaggaaa     120
attgcctcca ttgatttaat cctcacaagt ctggccatat ccagaatttg tctattgtgc     180
gtaatactat tagattgttt tatattggtg ctatatccag atgtctatgc cactggtaaa     240
gaaatgagaa tcattgactt cttctggaca ctaaccaatc atttaagtat ctggtttgca     300
acctgcctca gcatttacta tttcttcaag ataggtaatt tctttcaccc acttttcctc     360
tggatgaagt ggagaattga cagggtgatt tcctggattc tactggggtg cgtggttctc     420
tctgtgttta ttagccttcc agccactgag aatttgaacg ctgatttcag gttttgtgtg     480
aaggcaaaga ggaaaacaaa cttaacttgg agttgcagag taaataaaac tcaacatgct     540
tctaccaagt tatttctcaa cctggcaacg ctgctcccct tttgtgtgtg cctaatgtcc     600
tttttcctct tgatcctctc cctgcggaga catatcaggc gaatgcagct cagtgccaca     660
gggtgcagag accccagcac agaagcccat gtgagagccc tgaaagctgt catttccttc     720
cttctcctct ttattgccta ctatttgtcc tttctcattg ccacctccag ctactttatg     780
ccagagacgg aattagctgt gattttggt gagtccatag ctctaatcta cccctcaagt     840
cattcattta tcctaaatact ggggaacaat aaattaagac atgcatctct aaaggtgatt     900
tggaaagtaa tgtctattct aaaaggaaga aaattccaac aacataaaat ctga          954

<210> SEQ ID NO 49
<211> LENGTH: 309
<212> TYPE: PRT
<213> ORGANISM: Homo sapiens
<220> FEATURE:
<223> OTHER INFORMATION: human GR08

<400> SEQUENCE: 49

Met Phe Ser Pro Ala Asp Asn Ile Phe Ile Ile Leu Ile Thr Gly Glu
  1               5                  10                  15

Phe Ile Leu Gly Ile Leu Gly Asn Gly Tyr Ile Ala Leu Val Asn Trp
             20                  25                  30

Ile Asp Trp Ile Lys Lys Lys Ile Ser Thr Val Asp Tyr Ile Leu
         35                  40                  45

Thr Asn Leu Val Ile Ala Arg Ile Cys Leu Ile Ser Val Met Val Val
     50                  55                  60

Asn Gly Ile Val Ile Val Leu Asn Pro Asp Val Tyr Thr Lys Asn Lys
 65                  70                  75                  80

Gln Gln Ile Val Ile Phe Thr Phe Trp Thr Phe Ala Asn Tyr Leu Asn
                 85                  90                  95
```

```
Met Trp Ile Thr Thr Cys Leu Asn Val Phe Tyr Phe Leu Lys Ile Ala
            100                 105                 110
Ser Ser Ser His Pro Leu Phe Leu Trp Leu Lys Trp Lys Ile Asp Met
        115                 120                 125
Val Val His Trp Ile Leu Leu Gly Cys Phe Ala Ile Ser Leu Leu Val
    130                 135                 140
Ser Leu Ile Ala Ala Ile Val Leu Ser Cys Asp Tyr Arg Phe His Ala
145                 150                 155                 160
Ile Ala Lys His Lys Arg Asn Ile Thr Glu Met Phe His Val Ser Lys
                165                 170                 175
Ile Pro Tyr Phe Glu Pro Leu Thr Leu Phe Asn Leu Phe Ala Ile Val
            180                 185                 190
Pro Phe Ile Val Ser Leu Ile Ser Phe Phe Leu Leu Val Arg Ser Leu
        195                 200                 205
Trp Arg His Thr Lys Gln Ile Lys Leu Tyr Ala Thr Gly Ser Arg Asp
    210                 215                 220
Pro Ser Thr Glu Val His Val Arg Ala Ile Lys Thr Met Thr Ser Phe
225                 230                 235                 240
Ile Phe Phe Phe Phe Leu Tyr Tyr Ile Ser Ser Ile Leu Met Thr Phe
                245                 250                 255
Ser Tyr Leu Met Thr Lys Tyr Lys Leu Ala Val Glu Phe Gly Glu Ile
            260                 265                 270
Ala Ala Ile Leu Tyr Pro Leu Gly His Ser Leu Ile Leu Ile Val Leu
        275                 280                 285
Asn Asn Lys Leu Arg Gln Thr Phe Val Arg Met Leu Thr Cys Arg Lys
    290                 295                 300
Ile Ala Cys Met Ile
305

<210> SEQ ID NO 50
<211> LENGTH: 930
<212> TYPE: DNA
<213> ORGANISM: Homo sapiens
<220> FEATURE:
<223> OTHER INFORMATION: human GR08

<400> SEQUENCE: 50
atgttcagtc ctgcagataa catctttata atcctaataa ctggagaatt catactagga      60
atattgggga atggatacat tgcactagtc aactggattg actggattaa gaagaaaaag     120
atttccacag ttgactacat ccttaccaat ttagttatcg ccagaatttg tttgatcagt     180
gtaatggttg taaatggcat tgtaatagta ctgaacccag atgtttatac aaaaaataaa     240
caacagatag tcattttttac cttctggaca tttgccaact acttaaatat gtggattacc     300
acctgcctta atgtcttcta ttttctgaag atagccagtt cctctcatcc acttttctc     360 tggctgaagt ggaaaattga tatggtggtg cactggatcc tgctgggatg ctttgccatt     420
tccttgttgg tcagccttat agcagcaata gtactgagtt gtgattatag gtttcatgca     480
attgccaaac ataaaagaaa cattactgaa atgttccatg tgagtaaaat accatacttt     540
gaacccttga ctctctttaa cctgtttgca attgtcccat ttattgtgtc actgatatca     600 ttttttcctttt tagtaagatc tttatggaga cataccaagc aaataaaact ctatgctacc     660
ggcagtagag accccagcac agaagttcat gtgagagcca ttaaaactat gacttcattt     720
atcttctttt ttttcctata ctatatttct tctattttga tgaccttta g ctatcttatg     780 acaaaataca agttagctgt ggagtttgga gagattgcag caattctcta ccccttgggt     840
```

```
cactcactta ttttaattgt tttaaataat aaactgaggc agacatttgt cagaatgctg      900
acatgtagaa aaattgcctg catgatatga                                      930
```

<210> SEQ ID NO 51
<211> LENGTH: 312
<212> TYPE: PRT
<213> ORGANISM: Homo sapiens
<220> FEATURE:
<223> OTHER INFORMATION: human GR09

<400> SEQUENCE: 51

```
Met Pro Ser Ala Ile Glu Ala Ile Tyr Ile Ile Leu Ile Ala Gly Glu
 1               5                  10                  15

Leu Thr Ile Gly Ile Trp Gly Asn Gly Phe Ile Val Leu Val Asn Cys
            20                  25                  30

Ile Asp Trp Leu Lys Arg Arg Asp Ile Ser Leu Ile Asp Ile Ile Leu
        35                  40                  45

Ile Ser Leu Ala Ile Ser Arg Ile Cys Leu Leu Cys Val Ile Ser Leu
    50                  55                  60

Asp Gly Phe Phe Met Leu Leu Phe Pro Gly Thr Tyr Gly Asn Ser Val
65                  70                  75                  80

Leu Val Ser Ile Val Asn Val Val Trp Thr Phe Ala Asn Asn Ser Ser
                85                  90                  95

Leu Trp Phe Thr Ser Cys Leu Ser Ile Phe Tyr Leu Leu Lys Ile Ala
           100                 105                 110

Asn Ile Ser His Pro Phe Phe Phe Trp Leu Lys Leu Lys Ile Asn Lys
        115                 120                 125

Val Met Leu Ala Ile Leu Leu Gly Ser Phe Leu Ile Ser Leu Ile Ile
    130                 135                 140

Ser Val Pro Lys Asn Asp Asp Met Trp Tyr His Leu Phe Lys Val Ser
145                 150                 155                 160

His Glu Glu Asn Ile Thr Trp Lys Phe Lys Val Ser Lys Ile Pro Gly
                165                 170                 175

Thr Phe Lys Gln Leu Thr Leu Asn Leu Gly Val Met Val Pro Phe Ile
            180                 185                 190

Leu Cys Leu Ile Ser Phe Phe Leu Leu Phe Ser Leu Val Arg His
        195                 200                 205

Thr Lys Gln Ile Arg Leu His Ala Thr Gly Phe Arg Asp Pro Ser Thr
    210                 215                 220

Glu Ala His Met Arg Ala Ile Lys Ala Val Ile Ile Phe Leu Leu Leu
225                 230                 235                 240

Leu Ile Val Tyr Tyr Pro Val Phe Leu Val Met Thr Ser Ser Ala Leu
                245                 250                 255

Ile Pro Gln Gly Lys Leu Val Leu Met Ile Gly Asp Ile Val Thr Val
            260                 265                 270

Ile Phe Pro Ser Ser His Ser Phe Ile Leu Ile Met Gly Asn Ser Lys
        275                 280                 285

Leu Arg Glu Ala Phe Leu Lys Met Leu Arg Phe Val Lys Cys Phe Leu
    290                 295                 300

Arg Arg Arg Lys Pro Phe Val Pro
305                 310
```

<210> SEQ ID NO 52
<211> LENGTH: 939
<212> TYPE: DNA

<213> ORGANISM: Homo sapiens
<220> FEATURE:
<223> OTHER INFORMATION: human GR09

<400> SEQUENCE: 52

```
atgccaagtg caatagaggc aatatatatt attttaattg ctggtgaatt gaccataggg      60
atttggggaa atggattcat tgtactagtt aactgcattg actggctcaa aagaagagat     120
atttccttga ttgacatcat cctgatcagc ttggccatct ccagaatctg tctgctgtgt     180
gtaatatcat tagatggctt ctttatgctg ctctttccag gtacatatgg caatagcgtg     240
ctagtaagca ttgtgaatgt tgtctggaca tttgccaata attcaagtct ctggtttact     300
tcttgcctca gtatcttcta tttactcaag atagccaata tatcgcaccc atttttcttc     360
tggctgaagc taaagatcaa caaggtcatg cttgcgattc ttctggggtc ctttcttatc     420
tctttaatta ttagtgttcc aaagaatgat gatatgtggt atcacctttt caaagtcagt     480
catgaagaaa acattacttg gaaattcaaa gtgagtaaaa ttccaggtac tttcaaacag     540
ttaaccctga acctgggggt gatggttccc tttatccttt gcctgatctc attttttcttg     600
ttacttttct ccctagttag acacaccaag cagattcgac tgcatgctac agggttcaga     660
gaccccagta cagaggccca catgagggcc ataaaggcag tgatcatctt tctgctcctc     720
ctcatcgtgt actacccagt ctttcttgtt atgacctcta cgctctgat tcctcaggga     780
aaattagtgt tgatgattgg tgacatagta actgtcattt cccatcaag ccattcattc     840
attctaatta tgggaaatag caagttgagg gaagcttttc tgaagatgtt aagatttgtg     900
aagtgtttcc ttagaagaag aaagcctttt gttccatag                            939
```

<210> SEQ ID NO 53
<211> LENGTH: 307
<212> TYPE: PRT
<213> ORGANISM: Homo sapiens
<220> FEATURE:
<223> OTHER INFORMATION: human GR10

<400> SEQUENCE: 53

```
Met Leu Arg Val Val Glu Gly Ile Phe Ile Phe Val Val Ser Glu
  1               5                  10                  15

Ser Val Phe Gly Val Leu Gly Asn Gly Phe Ile Gly Leu Val Asn Cys
                 20                  25                  30

Ile Asp Cys Ala Lys Asn Lys Leu Ser Thr Ile Gly Phe Ile Leu Thr
             35                  40                  45

Gly Leu Ala Ile Ser Arg Ile Phe Leu Ile Trp Ile Ile Thr Asp
         50                  55                  60

Gly Phe Ile Gln Ile Phe Ser Pro Asn Ile Tyr Ala Ser Gly Asn Leu
 65                  70                  75                  80

Ile Glu Tyr Ile Ser Tyr Phe Trp Val Ile Gly Asn Gln Ser Ser Met
                 85                  90                  95

Trp Phe Ala Thr Ser Leu Ser Ile Phe Tyr Phe Leu Lys Ile Ala Asn
            100                 105                 110

Phe Ser Asn Tyr Ile Phe Leu Trp Leu Lys Ser Arg Thr Asn Met Val
            115                 120                 125

Leu Pro Phe Met Ile Val Phe Leu Ile Ser Leu Leu Asn Phe
        130                 135                 140

Ala Tyr Ile Ala Lys Ile Leu Asn Asp Tyr Lys Thr Lys Asn Asp Thr
145                 150                 155                 160

Val Trp Asp Leu Asn Met Tyr Lys Ser Glu Tyr Phe Ile Lys Gln Ile
```

Leu Leu Asn Leu Gly Val Ile Phe Phe Thr Leu Ser Leu Ile Thr
                165                 170                 175

Cys Ile Phe Leu Ile Ile Ser Leu Trp Arg His Asn Arg Gln Met Gln
        180                 185                 190

Ser Asn Val Thr Gly Leu Arg Asp Ser Asn Thr Glu Ala His Val Lys
195                 200                 205

Ala Met Lys Val Leu Ile Ser Phe Ile Ile Leu Phe Ile Leu Tyr Phe
210                 215                 220

Ile Gly Met Ala Ile Glu Ile Ser Cys Phe Thr Val Arg Glu Asn Lys
225                 230                 235                 240

Leu Leu Leu Met Phe Gly Met Thr Thr Thr Ala Ile Tyr Pro Trp Gly
        245                 250                 255

His Ser Phe Ile Leu Ile Leu Gly Asn Ser Lys Leu Lys Gln Ala Ser
    260                 265                 270

Leu Arg Val Leu Gln Gln Leu Lys Cys Cys Glu Lys Arg Lys Asn Leu
275                 280                 285

Arg Val Thr
        290                 295                 300

305

<210> SEQ ID NO 54
<211> LENGTH: 924
<212> TYPE: DNA
<213> ORGANISM: Homo sapiens
<220> FEATURE:
<223> OTHER INFORMATION: human GR10

<400> SEQUENCE: 54
atgctacgtg tagtggaagg catcttcatt tttgttgtag ttagtgagtc agtgtttggg      60
gttttgggga atggatttat tggacttgta aactgcattg actgtgccaa gaataagtta     120
tctacgattg gctttattct caccggctta gctatttcaa gaatttttct gatatggata     180
ataattacag atggatttat acagatattc tctccaaata tatatgcctc cggtaaccta     240
attgaatata ttagttactt ttgggtaatt ggtaatcaat caagtatgtg gtttgccacc     300
agcctcagca tcttctattt cctgaagata gcaaattttt ccaactacat atttctctgg     360
ttgaagagca gaacaaatat ggttcttccc ttcatgatag tattcttact tatttcatcg     420
ttacttaatt ttgcatacat tgcgaagatt cttaatgatt ataaaacgaa gaatgacaca     480
gtctgggatc tcaacatgta taaaagtgaa tactttatta aacagatttt gctaaatctg     540
ggagtcattt tcttctttac actatcccta attacatgta ttttttttaat catttcccct     600
tggagacaca acaggcagat gcaatcgaat gtgacaggat tgagagactc caacacagaa     660
gctcatgtga aggcaatgaa agttttgata tctttcatca tcctctttat cttgtatttt     720
ataggcatgg ccatagaaat atcatgtttt actgtgcgag aaaacaaact gctgcttatg     780
tttggaatga caaccacagc catctatccc tggggtcact catttatctt aattctagga     840
aacagcaagc taaagcaagc ctctttgagg gtactgcagc aattgaagtg ctgtgagaaa     900
aggaaaaatc tcagagtcac atag                                            924

<210> SEQ ID NO 55
<211> LENGTH: 245
<212> TYPE: PRT
<213> ORGANISM: Homo sapiens
<220> FEATURE:
<221> NAME/KEY: MOD_RES
<222> LOCATION: (1)..(245)

-continued

```
<223> OTHER INFORMATION: human GR11
<223> OTHER INFORMATION: Xaa = any amino acid

<400> SEQUENCE: 55

Met Ala Asn Met Leu Lys Asn Met Leu Thr Met Ile Ser Ala Ile Asp
  1               5                  10                  15

Phe Ile Met Gly Ile Gln Arg Ser Arg Val Met Val Leu Val His Cys
               20                  25                  30

Ile Asp Trp Ile Arg Arg Trp Lys Leu Ser Leu Ile Asp Phe Ile Leu
           35                  40                  45

Thr Cys Trp Ala Ile Ser Arg Ile Phe Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Asn His Leu Cys Thr Xaa Phe
                 85                  90                  95

Ala Thr Cys Leu Ala Val Phe Tyr Phe Leu Lys Ile Val Asn Phe Ser
                100                 105                 110

Tyr Leu Phe Tyr Phe Trp Leu Lys Trp Arg Ile Asn Lys Val Ala Phe
            115                 120                 125

Ile Leu Pro Leu Val Ser Ala Phe Ser Val Tyr Gln Leu Ser Phe Asp
        130                 135                 140

Val His Phe Xaa Cys Leu Leu Val Ser Cys Pro Lys Lys Tyr Glu Arg
145                 150                 155                 160

His Met Thr Gly Leu Leu Asn Val Ser Asn Asn Lys Asn Val Asn Asn
                165                 170                 175

Ile Ile Ile Phe Phe Ile Gly Ser Leu Ser Ser Phe Ser Ile Ser Ser
            180                 185                 190

Ile Phe Phe Leu Leu Leu Leu Ser Ser Xaa Arg His Met Lys His
        195                 200                 205

Ile Arg Phe Asn Phe Arg Asp Cys Arg Thr Pro Val Tyr Gly Pro Ile
    210                 215                 220

Ser Glu Pro Arg Lys Arg Phe Ser Phe Val Leu Leu Leu Tyr Lys
225                 230                 235                 240

Asn Leu Pro Phe Ser
                245

<210> SEQ ID NO 56
<211> LENGTH: 315
<212> TYPE: PRT
<213> ORGANISM: Homo sapiens
<220> FEATURE:
<221> NAME/KEY: MOD_RES
<222> LOCATION: (1)..(315)
<223> OTHER INFORMATION: human GR12
<223> OTHER INFORMATION: Xaa = any amino acid

<400> SEQUENCE: 56

Met Ser Ser Ile Trp Glu Thr Leu Phe Ile Arg Ile Leu Val Val Xaa
  1               5                  10                  15

Phe Ile Met Gly Thr Val Gly Asn Xaa Phe Ile Val Leu Val Asn Ile
               20                  25                  30

Ile Asp Xaa Ile Arg Asn Xaa Lys Val Ser Leu Ile Asp Phe Ile Leu
           35                  40                  45

Asn Cys Leu Ala Ile Ser Arg Ile Cys Phe Leu Xaa Ile Thr Ile Leu
        50                  55                  60

Ala Thr Ser Phe Asn Ile Gly Tyr Glu Lys Met Pro Asp Ser Lys Asn
```

```
                65                  70                  75                  80
Leu Ala Val Ser Phe Asp Ile Leu Trp Thr Gly Ser Ser Tyr Phe Cys
                    85                  90                  95
Leu Ser Cys Thr Thr Cys Leu Ser Val Phe Tyr Phe Leu Lys Val Ala
                100                 105                 110
Asn Phe Ser Asn Pro Ile Phe Leu Trp Met Lys Trp Lys Ile His Lys
                115                 120                 125
Val Leu Leu Phe Ile Val Leu Glu Ala Thr Ile Ser Phe Cys Thr Thr
    130                 135                 140
Ser Ile Leu Lys Glu Ile Ile Ile Asn Ser Leu Ile Xaa Glu Arg Val
145                 150                 155                 160
Thr Ile Lys Gly Asn Leu Thr Phe Asn Tyr Met Asp Thr Met His Asp
                165                 170                 175
Phe Thr Ser Leu Phe Leu Leu Gln Met Met Phe Ile Leu Pro Phe Val
                180                 185                 190
Glu Thr Leu Ala Ser Ile Leu Leu Leu Ile Leu Ser Leu Trp Ser His
                195                 200                 205
Thr Arg Gln Met Lys Leu His Gly Ile Tyr Ser Arg Asp Pro Ser Thr
    210                 215                 220
Glu Ala His Val Lys Pro Ile Lys Ala Ile Ile Ser Phe Leu Leu Leu
225                 230                 235                 240
Phe Ile Val His Tyr Phe Ile Ser Ile Ile Leu Thr Leu Ala Cys Pro
                245                 250                 255
Leu Leu Asp Phe Val Ala Ala Arg Thr Phe Ser Ser Val Leu Val Phe
                260                 265                 270
Phe His Pro Ser Gly His Ser Phe Leu Leu Ile Leu Arg Asp Ser Lys
            275                 280                 285
Leu Lys Gln Ala Ser Leu Cys Val Leu Lys Lys Met Lys Tyr Ala Lys
            290                 295                 300
Lys Asp Ile Ile Ser His Phe Tyr Lys His Ala
305                 310                 315

<210> SEQ ID NO 57
<211> LENGTH: 948
<212> TYPE: DNA
<213> ORGANISM: Homo sapiens
<220> FEATURE:
<223> OTHER INFORMATION: human GR12

<400> SEQUENCE: 57
atgtcaagca tttgggagac actgtttata agaattcttg tagtgtaatt cataatgggg    60
actgtgggaa attgattcat tgtattggtt aatatcattg actgaatcag gaactgaaag   120
gtctccctga ttgattttat tctcaactgc ttggccatct ccaggatatg tttcctgtag   180
ataacaattt tagctacctc tttcaatata ggctatgaga aaatgcctga ttctaagaat   240
cttgcagtaa gttttgacat tctctggaca ggatccagct atttctgcct gtcctgtacc   300
acttgcctca gtgtcttcta tttcctcaag gtagccaact tctccaatcc cattttcctc   360
tggatgaaat ggaaaattca aaggtgcttt ctctttattg tactagaggc aacgatctct   420
ttctgcacaa cttccattct gaaggaaata ataattaata gtttaatcta agaacgggta   480
acaataaaag gcaacttgac atttaattat atggatacca tgcatgattt cacttctctg   540
tttctccttc agatgatgtt catccttcct tttgtggaaa cactggcttc cattcttctc   600
ttaatcctct ccttatggag ccacaccagg cagatgaagc tacatggtat ttattccagg   660
```

```
gatcccagca cagaagccca tgtaaaacct ataaaagcta taatttcatt tctactcctc    720
tttattgtgc attatttcat cagtatcata ctaacattgg cctgtcctct tctagacttc    780
gttgcggcaa ggacttttag tagtgtgctg gtattttttcc atccatctgg ccattcattt    840
cttctaattt tacgggacag caaactgaag caagcttctc tctgtgtcct gaagaagatg    900
aagtatgcca aaaggacat aatctctcat ttttataaac atgcctga                948
```

<210> SEQ ID NO 58
<211> LENGTH: 300
<212> TYPE: PRT
<213> ORGANISM: Homo sapiens
<220> FEATURE:
<223> OTHER INFORMATION: human GR13

<400> SEQUENCE: 58

```
Met Glu Ser Ala Leu Pro Ser Ile Phe Thr Leu Val Ile Ile Ala Glu
 1               5                  10                  15

Phe Ile Ile Gly Asn Leu Ser Asn Gly Phe Ile Val Leu Ile Asn Cys
                20                  25                  30

Ile Asp Trp Val Ser Lys Arg Glu Leu Ser Ser Val Asp Lys Leu Leu
            35                  40                  45

Ile Ile Leu Ala Ile Ser Arg Ile Gly Leu Ile Trp Glu Ile Leu Val
        50                  55                  60

Ser Trp Phe Leu Ala Leu His Tyr Leu Ala Ile Phe Val Ser Gly Thr
 65                  70                  75                  80

Gly Leu Arg Ile Met Ile Phe Ser Trp Ile Val Ser Asn His Phe Asn
                85                  90                  95

Leu Trp Leu Ala Thr Ile Phe Ser Ile Phe Tyr Leu Leu Lys Ile Ala
            100                 105                 110

Ser Phe Ser Ser Pro Ala Phe Leu Tyr Leu Lys Trp Arg Val Asn Lys
        115                 120                 125

Val Ile Leu Met Ile Leu Leu Gly Thr Leu Val Phe Leu Phe Leu Asn
    130                 135                 140

Leu Ile Gln Ile Asn Met His Ile Lys Asp Trp Leu Asp Arg Tyr Glu
145                 150                 155                 160

Arg Asn Thr Thr Trp Asn Phe Ser Met Ser Asp Phe Glu Thr Phe Ser
                165                 170                 175

Val Ser Val Lys Phe Thr Met Thr Met Phe Ser Leu Thr Pro Phe Thr
            180                 185                 190

Val Ala Phe Ile Ser Phe Leu Leu Ile Phe Ser Leu Gln Lys His
        195                 200                 205

Leu Gln Lys Met Gln Leu Asn Tyr Lys Gly His Arg Asp Pro Arg Thr
    210                 215                 220

Lys Val His Thr Asn Ala Leu Lys Ile Val Ile Ser Phe Leu Leu Phe
225                 230                 235                 240

Tyr Ala Ser Phe Phe Leu Cys Val Leu Ile Ser Trp Ile Ser Glu Leu
                245                 250                 255

Tyr Gln Asn Thr Val Ile Tyr Met Leu Cys Glu Thr Ile Gly Val Phe
            260                 265                 270

Ser Pro Ser Ser His Ser Phe Leu Ile Leu Gly Asn Ala Lys Leu
        275                 280                 285

Arg Gln Ala Phe Leu Leu Val Ala Ala Lys Val Trp
    290                 295                 300
```

<210> SEQ ID NO 59

<211> LENGTH: 912
<212> TYPE: DNA
<213> ORGANISM: Homo sapiens
<220> FEATURE:
<223> OTHER INFORMATION: human GR13

<400> SEQUENCE: 59

```
atggaaagtg ccctgccgag tatcttcact cttgtaataa ttgcagaatt cataattggg      60
aatttgagca atggatttat agtactgatc aactgcattg actgggtcag taaaagagag     120
ctgtcctcag tcgataaact cctcattatc ttggcaatct ccagaattgg gctgatctgg     180
gaaatattag taagttggtt tttagctctg cattatctag ccatatttgt gtctggaaca     240
ggattaagaa ttatgatttt tagctggata gtttctaatc acttcaatct ctggcttgct     300
acaatcttca gcatctttta tttgctcaaa atagcgagtt tctctagccc tgcttttctc     360
tatttgaagt ggagagtaaa caaagtgatt ctgatgatac tgctaggaac cttggtcttc     420
ttatttttaa atctgataca aataaacatg catataaaag actggctgga ccgatatgaa     480
agaaacacaa cttggaattt cagtatgagt gactttgaaa cattttcagt gtcggtcaaa     540
ttcactatga ctatgttcag tctaacacca tttactgtgg ccttcatctc ttttctcctg     600
ttaatttttct ccctgcagaa acatctccag aaaatgcaac tcaattacaa aggacacaga     660
gaccccagga ccaaggtcca tacaaatgcc ttgaaaattg tgatctcatt ccttttattc     720
tatgctagtt tctttctatg tgttctcata tcatggattt ctgagctgta tcagaacaca     780
gtgatctaca tgctttgtga gacgattgga gtcttctctc cttcaagcca ctcctttctt     840
ctgattctag gaaacgctaa gttaagacag gcctttcttt tggtggcagc taaggtatgg     900
gctaaacgat ga                                                         912
```

<210> SEQ ID NO 60
<211> LENGTH: 317
<212> TYPE: PRT
<213> ORGANISM: Homo sapiens
<220> FEATURE:
<223> OTHER INFORMATION: human GR14

<400> SEQUENCE: 60

```
Met Gly Gly Val Ile Lys Ser Ile Phe Thr Phe Val Leu Ile Val Glu
  1               5                  10                  15

Phe Ile Ile Gly Asn Leu Gly Asn Ser Phe Ile Ala Leu Val Asn Cys
                 20                  25                  30

Ile Asp Trp Val Lys Gly Arg Lys Ile Ser Ser Val Asp Arg Ile Leu
             35                  40                  45

Thr Ala Leu Ala Ile Ser Arg Ile Ser Leu Val Trp Leu Ile Phe Gly
         50                  55                  60

Ser Trp Cys Val Ser Val Phe Phe Pro Ala Leu Phe Ala Thr Glu Lys
 65                  70                  75                  80

Met Phe Arg Met Leu Thr Asn Ile Trp Thr Val Ile Asn His Phe Ser
                 85                  90                  95

Val Trp Leu Ala Thr Gly Leu Gly Thr Phe Tyr Phe Leu Lys Ile Ala
            100                 105                 110

Asn Phe Ser Asn Ser Ile Phe Leu Tyr Leu Lys Trp Arg Val Lys Lys
            115                 120                 125

Val Val Leu Val Leu Leu Val Thr Ser Val Phe Leu Phe Leu Asn
        130                 135                 140

Ile Ala Leu Ile Asn Ile His Ile Asn Ala Ser Ile Asn Gly Tyr Arg
145                 150                 155                 160
```

```
Arg Asn Lys Thr Cys Ser Ser Asp Ser Ser Asn Phe Thr Arg Phe Ser
                165                 170                 175

Ser Leu Ile Val Leu Thr Ser Thr Val Phe Ile Phe Ile Pro Phe Thr
            180                 185                 190

Leu Ser Leu Ala Met Phe Leu Leu Leu Ile Phe Ser Met Trp Lys His
        195                 200                 205

Arg Lys Lys Met Gln His Thr Val Lys Ile Ser Gly Asp Ala Ser Thr
    210                 215                 220

Lys Ala His Arg Gly Val Lys Ser Val Ile Thr Phe Phe Leu Leu Tyr
225                 230                 235                 240

Ala Ile Phe Ser Leu Ser Phe Phe Ile Ser Val Trp Thr Ser Glu Arg
                245                 250                 255

Leu Glu Glu Asn Leu Ile Ile Leu Ser Gln Val Met Gly Met Ala Tyr
            260                 265                 270

Pro Ser Cys His Ser Cys Val Leu Ile Leu Gly Asn Lys Lys Leu Arg
        275                 280                 285

Gln Ala Ser Leu Ser Val Leu Leu Trp Leu Arg Tyr Met Phe Lys Asp
    290                 295                 300

Gly Glu Pro Ser Gly His Lys Glu Phe Arg Glu Ser Ser
305                 310                 315

<210> SEQ ID NO 61
<211> LENGTH: 954
<212> TYPE: DNA
<213> ORGANISM: Homo sapiens
<220> FEATURE:
<223> OTHER INFORMATION: human GR14

<400> SEQUENCE: 61
atgggtggtg tcataaagag catatttaca ttcgttttaa ttgtggaatt tataattgga      60
aatttaggaa atagtttcat agcactggtg aactgtattg actgggtcaa gggaagaaag     120
atctcttcgg ttgatcggat cctcactgct ttggcaatct ctcgaattag cctggtttgg     180
ttaatattcg gaagctggtg tgtgtctgtg tttttcccag cttatttgc cactgaaaaa      240 atgttcagaa tgcttactaa tatctggaca gtgatcaatc attttagtgt ctggttagct     300
acaggcctcg gtactttta ttttctcaag atagccaatt tttctaactc tattttctc       360 tacctaaagt ggagggttaa aaaggtggtt ttggtgctgc ttcttgtgac ttcggtcttc     420
ttgtttttaa atattgcact gataaacatc catataaatg ccagtatcaa tggatacaga     480
agaaacaaga cttgcagttc tgattcaagt aactttacac gattttccag tcttattgta     540
ttaaccagca ctgtgttcat tttcataccc tttactttgt ccctggcaat gtttcttctc     600
ctcatcttct ccatgtggaa acatcgcaag aagatgcagc acactgtcaa aatatccgga     660
gacgccagca caaagcccca cagaggagtt aaaagtgtga tcactttctt cctactctat     720
gccattttct ctctgtcttt tttcatatca gtttggacct ctgaaaggtt ggaggaaaat     780
ctaattattc tttcccaggt gatgggaatg gcttatcctt catgtcactc atgtgttctg     840
attcttggaa acaagaagct gagacaggcc tctctgtcag tgctactgtg gctgaggtac     900
atgttcaaag atggggagcc ctcaggtcac aaagaattta gagaatcatc ttga           954

<210> SEQ ID NO 62
<211> LENGTH: 300
<212> TYPE: PRT
<213> ORGANISM: Homo sapiens
<220> FEATURE:
```

<221> NAME/KEY: MOD_RES
<222> LOCATION: (257)
<223> OTHER INFORMATION: human GR15
<223> OTHER INFORMATION: Xaa = any amino acid

<400> SEQUENCE: 62

Met Ile Thr Phe Leu Pro Ile Ile Phe Ser Ile Leu Val Val Thr
1               5                   10                  15

Phe Val Leu Gly Asn Phe Ala Asn Gly Phe Ile Val Leu Val Asn Ser
            20                  25                  30

Ile Glu Trp Val Lys Arg Gln Lys Ile Ser Phe Ala Asp Gln Ile Leu
        35                  40                  45

Thr Ala Leu Ala Val Ser Arg Val Gly Leu Leu Trp Val Ile Leu Leu
    50                  55                  60

His Trp Tyr Ala Thr Val Leu Asn Pro Gly Ser Tyr Ser Leu Gly Val
65                  70                  75                  80

Arg Ile Thr Thr Ile Asn Ala Trp Ala Val Thr Asn His Phe Ser Ile
                85                  90                  95

Trp Val Ala Thr Ser Leu Ser Ile Phe Tyr Phe Leu Lys Ile Ala Asn
            100                 105                 110

Phe Ser Asn Phe Ile Phe Leu His Leu Lys Arg Arg Ile Lys Ser Val
        115                 120                 125

Ile Pro Val Ile Leu Leu Gly Ser Leu Leu Phe Leu Val Cys His Leu
    130                 135                 140

Val Val Val Asn Met Asp Glu Ser Met Trp Thr Lys Glu Tyr Glu Gly
145                 150                 155                 160

Asn Val Ser Trp Glu Ile Lys Leu Ser Asp Pro Thr His Leu Ser Asp
                165                 170                 175

Met Thr Val Thr Thr Leu Ala Asn Leu Ile Pro Phe Thr Leu Ser Leu
            180                 185                 190

Leu Ser Phe Leu Leu Leu Ile Cys Ser Leu Cys Lys His Leu Lys Lys
        195                 200                 205

Met Gln Phe His Gly Lys Gly Ser Pro Asp Ser Asn Thr Lys Val His
    210                 215                 220

Ile Lys Ala Leu Gln Thr Val Thr Ser Phe Leu Leu Phe Ala Val
225                 230                 235                 240

Tyr Phe Leu Ser Leu Ile Thr Ser Ile Trp Asn Phe Arg Arg Arg Leu
                245                 250                 255

Xaa Asn Glu Pro Val Leu Met Leu Ser Gln Thr Thr Ala Ile Ile Tyr
            260                 265                 270

Pro Ser Phe His Ser Phe Ile Leu Ile Trp Gly Ser Lys Lys Leu Lys
        275                 280                 285

Gln Thr Phe Leu Leu Ile Leu Cys Gln Ile Lys Cys
    290                 295                 300

<210> SEQ ID NO 63
<211> LENGTH: 903
<212> TYPE: DNA
<213> ORGANISM: Homo sapiens
<220> FEATURE:
<223> OTHER INFORMATION: human GR15

<400> SEQUENCE: 63
atgataactt ttctacccat cattttttcc attctagtag tggttacatt tgttcttggg      60
aattttgcta atggcttcat agtgttggta aattccattg agtgggtcaa gagacaaaag     120
atctcctttg ctgaccaaat tctcactgct ctggcagtct ccagagttgg tttgctctgg     180

```
                                    -continued gtaatattat tacattggta tgcaactgtt ttgaatccag gttcatatag tttaggagta      240
agaattacta ctattaatgc ctgggctgta accaaccatt tcagcatctg ggttgctact      300
agcctcagca tatttatttt cctcaagatt gccaatttct ccaactttat ttttcttcac      360
ttaaaaagga gaattaagag tgtcattcca gtgatactat tggggtcttt gttattttttg     420 gtttgtcatc ttgttgtggt aaacatggat gagagtatgt ggacaaaaga atatgaagga     480
aacgtgagtt gggagatcaa attgagtgat ccgacgcacc tttcagatat gactgtaacc     540
acgcttgcaa acttaatacc ctttactctg tccctgttat cttttctgct cttaatctgt     600
tctttgtgta acatctcaa gaagatgcag ttccatggca aaggatctcc agattccaac      660
accaaggtcc acataaaagc tttgcaaacg tgacctcct tcctcttgtt atttgctgtt      720
tactttctgt ccctaatcac atcgatttgg aattttagga ggaggctgta gaacgaacct      780
gtcctcatgc tcagccaaac tactgcaatt atatacccctt catttcattc attcatccta     840
atttggggaa gcaagaagct gaaacagacc tttcttttga ttttgtgtca gattaagtgc      900
tga                                                                   903
```

<210> SEQ ID NO 64
<211> LENGTH: 291
<212> TYPE: PRT
<213> ORGANISM: Homo sapiens
<220> FEATURE:
<223> OTHER INFORMATION: human GR16

<400> SEQUENCE: 64

```
Met Ile Pro Ile Gln Leu Thr Val Phe Phe Met Ile Ile Tyr Val Leu
 1               5                  10                  15

Glu Ser Leu Thr Ile Ile Val Gln Ser Ser Leu Ile Val Ala Val Leu
            20                  25                  30

Gly Arg Glu Trp Leu Gln Val Arg Arg Leu Met Pro Val Asp Met Ile
        35                  40                  45

Leu Ile Ser Leu Gly Ile Ser Arg Phe Cys Leu Gln Trp Ala Ser Met
    50                  55                  60

Leu Asn Asn Phe Cys Ser Tyr Phe Asn Leu Asn Tyr Val Leu Cys Asn
65                  70                  75                  80

Leu Thr Ile Thr Trp Glu Phe Phe Asn Ile Leu Thr Phe Trp Leu Asn
                85                  90                  95

Ser Leu Leu Thr Val Phe Tyr Cys Ile Lys Val Ser Ser Phe Thr His
            100                 105                 110

His Ile Phe Leu Trp Leu Arg Trp Arg Ile Leu Arg Leu Phe Pro Trp
        115                 120                 125

Ile Leu Leu Gly Ser Leu Met Ile Thr Cys Val Thr Ile Pro Ser
    130                 135                 140

Ala Ile Gly Asn Tyr Ile Gln Ile Gln Leu Leu Thr Met Glu His Leu
145                 150                 155                 160

Pro Arg Asn Ser Thr Val Thr Asp Lys Leu Glu Asn Phe His Gln Tyr
                165                 170                 175

Gln Phe Gln Ala His Thr Val Ala Leu Val Ile Pro Phe Ile Leu Phe
            180                 185                 190

Leu Ala Ser Thr Ile Phe Leu Met Ala Ser Leu Thr Lys Gln Ile Gln
        195                 200                 205

His His Ser Thr Gly His Cys Asn Pro Ser Met Lys Ala Arg Phe Thr
    210                 215                 220
```

```
Ala Leu Arg Ser Leu Ala Val Leu Phe Ile Val Phe Thr Ser Tyr Phe
225                 230                 235                 240

Leu Thr Ile Leu Ile Thr Ile Gly Thr Leu Phe Asp Lys Arg Cys
            245                 250                 255

Trp Leu Trp Val Trp Glu Ala Phe Val Tyr Ala Phe Ile Leu Met His
                260                 265                 270

Ser Thr Ser Leu Met Leu Ser Ser Pro Thr Leu Lys Arg Ile Leu Lys
        275                 280                 285

Gly Lys Cys
    290

<210> SEQ ID NO 65
<211> LENGTH: 876
<212> TYPE: DNA
<213> ORGANISM: Homo sapiens
<220> FEATURE:
<223> OTHER INFORMATION: human GR16

<400> SEQUENCE: 65
atgataccca tccaactcac tgtcttcttc atgatcatct atgtgcttga gtccttgaca      60 yattattgtgc agagcagcct aattgttgca gtgctgggca gagaatggct gcaagtcaga     120
aggctgatgc ctgtggacat gattctcatc agcctgggca tctctcgctt ctgtctacag     180
tgggcatcaa tgctgaacaa tttttgctcc tattttaatt tgaattatgt actttgcaac     240
ttaacaatca cctgggaatt ttttaatatc cttacattct ggttaaacag cttgcttacc     300
gtgttctact gcatcaaggt ctcttctttc acccatcaca tctttctctg gctgaggtgg     360
agaattttga ggttgtttcc ctggatatta ctgggttctc tgatgattac ttgtgtaaca     420 atcatcccctt cagctattgg gaattacatt caaattcagt tactcaccat ggagcatcta     480
ccaagaaaca gcactgtaac tgacaaactt gaaaattttc atcagtatca gttccaggct     540
catacagttg cattggttat tcctttcatc ctgttcctgg cctccaccat ctttctcatg     600
gcatcactga ccaagcagat acaacatcat agcactggtc actgcaatcc aagcatgaaa     660
gcgcgcttca ctgccctgag gtcccttgcc gtcttattta ttgtgtttac ctcttacttt     720
ctaaccatac tcatcaccat tataggtact ctatttgata gagatgttg gttatgggtc      780 tgggaagctt tgtctatgc tttcatctta atgcattcca cttcactgat gctgagcagc      840
cctacgttga aaaggattct aaagggaaag tgctag                                876

<210> SEQ ID NO 66
<211> LENGTH: 144
<212> TYPE: PRT
<213> ORGANISM: Homo sapiens
<220> FEATURE:
<221> NAME/KEY: MOD_RES
<222> LOCATION: (54)
<223> OTHER INFORMATION: human GR17
<223> OTHER INFORMATION: Xaa = any amino acid

<400> SEQUENCE: 66

Gly Ile Leu Ser Ile Leu Val Val Phe Ala Phe Val Leu Gly Asn Val
1               5                   10                  15

Ala Asn Gly Phe Ile Ala Leu Val Asn Val Asn Asp Trp Val Lys Thr
            20                  25                  30

Gln Lys Ile Ser Ser Thr Asp Gln Ile Val Thr Ala Leu Ala Phe Ser
        35                  40                  45

Arg Ile Gly Leu Leu Xaa Ile Ile Leu Leu His Trp Tyr Ala Thr Val
    50                  55                  60
```

```
Phe Asn Ser Ala Leu Tyr Ser Leu Glu Val Arg Ile Val Pro Ser Asn
 65                  70                  75                  80

Val Ser Ala Ile Ile Asn His Phe Ser Ile Trp Leu Ala Thr Ser Leu
                 85                  90                  95

Ser Ile Phe Tyr Leu Phe Lys Ile Ala Asn Phe Ser Asn Phe Ile Phe
            100                 105                 110

Leu His Leu Lys Lys Arg Ile Lys Ser Val Leu Val Ile Leu Leu
        115                 120                 125

Gly Ser Leu Val Phe Leu Ile Cys Asn Leu Ala Val Val Thr Met Gly
    130                 135                 140
```

<210> SEQ ID NO 67
<211> LENGTH: 554
<212> TYPE: DNA
<213> ORGANISM: Homo sapiens
<220> FEATURE:
<223> OTHER INFORMATION: human GR17

<400> SEQUENCE: 67

```
gggcatttta tcaattctgg tagtgtttgc atttgttctt ggaaatgttg ccaatggctt    60
catagctcta gttaatgtca atgactgggt taagacacaa aagatctcct caactgacca   120
aattgtcact gctctggcat tctccagaat tggtttactt tgatcatatt attacattgg   180
tatgcaactg tgtttaattc agctttatat agtttagaag taagaattgt tccttctaat   240
gtctcggcaa taatcaatca tttcagcatt tggcttgcta cgagcctcag catattttat   300
ttgttcaaga ttgccaattt ctccaatttt attttctcc acctaaagaa gagaattaag    360
agtgttcttc ttgtgatact gttggggtcc ttggtatttt tgatttgtaa tcttgctgtg   420
gtaaccatgg gatgacaggt gtgtggacaa aagaatttga aggaaatgtg acttgggaag   480
gatcgaattg aggaatgcaa tacacctttc aaacatgact ataacccaac catgctagca   540
aacttcacac tgta                                                    554
```

<210> SEQ ID NO 68
<211> LENGTH: 87
<212> TYPE: PRT
<213> ORGANISM: Homo sapiens
<220> FEATURE:
<223> OTHER INFORMATION: human GR18

<400> SEQUENCE: 68

```
Met Phe Val Gly Ile Asn Ile Phe Phe Leu Val Val Ala Thr Arg Gly
  1               5                  10                  15

Leu Val Leu Gly Met Leu Gly Asn Gly Leu Ile Gly Leu Val Asn Cys
             20                  25                  30

Ile Glu Trp Ala Lys Ser Trp Lys Val Ser Ser Ala Asp Phe Ile Leu
         35                  40                  45

Thr Ser Leu Ala Ile Val Arg Ile Ile Arg Leu Tyr Leu Ile Leu Phe
     50                  55                  60

Asp Ser Phe Ile Met Val Leu Ser Pro His Leu Tyr Thr Ile Arg Lys
 65                  70                  75                  80

Leu Val Lys Leu Phe Thr Ile
                 85
```

<210> SEQ ID NO 69
<211> LENGTH: 399
<212> TYPE: DNA
<213> ORGANISM: Homo sapiens

```
<220> FEATURE:
<221> NAME/KEY: modified_base
<222> LOCATION: (1)..(399)
<223> OTHER INFORMATION: human GR18
<223> OTHER INFORMATION: n = g, a, c or t

<400> SEQUENCE: 69
tcctgaaatt tggctatgcc ctctgaaatt ngtgatgaaa accatagatt agaaagcatc      60
ataaatgcat gcccatctgc aactgtttga cntataaagc tgtcagtgaa gtagaatatc     120
ggaaatattt tcatagaaat gttcgttgga attaatattt tctttctggt ggtggcaaca     180
agaggacttg tcttaggaat gctgggaaac gggctcattg gactggtaaa ctgcattgag     240
tgggccaaga gttggaaggt ctcatcagct gatttcatcc tcaccagctt ggctatagtc     300
agaatcattc gactgtattt aatactattt gattcattta taatggtatt gtcccctcat     360
ctatatacca tccgtaaact agtaaaactg tttactatt                           399

<210> SEQ ID NO 70
<211> LENGTH: 121
<212> TYPE: PRT
<213> ORGANISM: Homo sapiens
<220> FEATURE:
<223> OTHER INFORMATION: human GR19

<400> SEQUENCE: 70

Val Thr Thr Leu Ala Asn Leu Ile Pro Phe Thr Leu Ser Leu Ile Cys
  1               5                  10                  15

Phe Leu Leu Leu Ile Cys Ser Leu Cys Lys His Leu Lys Lys Met Arg
             20                  25                  30

Leu His Ser Lys Gly Ser Gln Asp Pro Ser Thr Lys Val His Ile Lys
         35                  40                  45

Ala Leu Gln Thr Val Thr Ser Phe Leu Met Leu Phe Ala Ile Tyr Phe
     50                  55                  60

Leu Cys Ile Ile Thr Ser Thr Trp Asn Leu Arg Thr Gln Gln Ser Lys
 65                  70                  75                  80

Leu Val Leu Leu Leu Cys Gln Thr Val Ala Ile Met Tyr Pro Ser Phe
                 85                  90                  95

His Ser Phe Ile Leu Ile Met Gly Ser Arg Lys Leu Lys Gln Thr Phe
            100                 105                 110

Leu Ser Val Leu Trp Gln Met Thr Cys
        115                 120

<210> SEQ ID NO 71
<211> LENGTH: 466
<212> TYPE: DNA
<213> ORGANISM: Homo sapiens
<220> FEATURE:
<223> OTHER INFORMATION: human GR19

<400> SEQUENCE: 71
ctgtaactac tctagcaaac ctcataccct ttactctgag cctaatatgt tttctgctgt      60
taatctgttc tctttgtaaa catctcaaga agatgcggct ccatagcaaa ggatctcaag     120
atcccagcac caaggtccat ataaaagctt tgcaaactgt gacctccttc tcatgttat     180 ttgccattta ctttctgtgt ataatcacat caacttggaa tcttaggaca cagcagagca     240
aacttgtact cctgctttgc caaactgttg caatcatgta tccttcattc cactcattca     300
tcctgattat gggaagtagg aagctaaaac agacctttct ttcagttttg tggcagatga     360
catgctgagt gaaagaagag aaaccctcaa ctccatagat tcacaagggg agcatcgtgg     420
```
gtcttctagc agaaaacaaa ctgatggtgt ctggaacatt ttatat           466

<210> SEQ ID NO 72
<211> LENGTH: 129
<212> TYPE: PRT
<213> ORGANISM: Homo sapiens
<220> FEATURE:
<221> NAME/KEY: MOD_RES
<222> LOCATION: (3)
<223> OTHER INFORMATION: human GR20
<223> OTHER INFORMATION: Xaa = any amino acid

<400> SEQUENCE: 72

His Leu Xaa Arg Lys Ala Lys Ser Val Val Leu Val Ile Val Leu Gly
 1               5                  10                  15

Ser Leu Phe Phe Leu Val Cys Gln Leu Val Met Lys Asn Thr Tyr Ile
                20                  25                  30

Asn Val Trp Thr Glu Glu Cys Glu Gly Asn Val Thr Trp Lys Ile Lys
            35                  40                  45

Leu Arg Asn Ala Met His Leu Ser Asn Leu Thr Val Ala Met Leu Ala
50                  55                  60

Asn Leu Ile Pro Phe Thr Leu Thr Val Ile Ser Phe Leu Leu Leu Ile
65                  70                  75                  80

Tyr Ser Leu Cys Lys His Leu Lys Lys Met Gln Leu His Gly Lys Gly
                85                  90                  95

Ser Gln Asp Pro Ser Thr Lys Ile His Ile Lys Ala Leu Gln Thr Val
            100                 105                 110

Thr Ser Phe Leu Val Leu Leu Ala Ile Tyr Phe Leu Cys Leu Ile Ile
        115                 120                 125

Ser

<210> SEQ ID NO 73
<211> LENGTH: 397
<212> TYPE: DNA
<213> ORGANISM: Homo sapiens
<220> FEATURE:
<221> NAME/KEY: modified_base
<222> LOCATION: (12)
<223> OTHER INFORMATION: human GR20
<223> OTHER INFORMATION: n = g, a, c or t

<400> SEQUENCE: 73
ttcatcactt anaaggaag gctaagagtg tagttctggt gatagtgttg gggtctttgt      60 tcttttggt tgtcaactt gtgatgaaaa acacgtatat aaatgtgtgg acagaagaat     120
gtgaaggaaa cgtaacttgg aagatcaaac tgaggaatgc aatgcacctt tccaacttga   180
ctgtagccat gctagcaaac ttgataccat tcactctgac cgtgatatct tttctgctgt   240
taatctactc tctgtgtaaa catctgaaga agatgcagct ccatggcaaa ggatctcaag   300
atcccagcac caagatccac ataaaagctc tgcaaactgt gacctccttc ctcgtattac   360
ttgccattta ctttctgtgt ctaatcatat ccttttg                            397

<210> SEQ ID NO 74
<211> LENGTH: 65
<212> TYPE: PRT
<213> ORGANISM: Homo sapiens
<220> FEATURE:
<221> NAME/KEY: MOD_RES
<222> LOCATION: (52)
<223> OTHER INFORMATION: human GR21
<223> OTHER INFORMATION: Xaa = any amino acid

<400> SEQUENCE: 74

Met Ile Thr Phe Leu Pro Ile Ile Phe Ser Ile Leu Ile Val Val Ile
1               5                   10                  15

Phe Val Ile Gly Lys Phe Ala Asn Gly Phe Ile Ala Leu Val Asn Ser
            20                  25                  30

Ile Glu Trp Val Lys Arg Gln Lys Ile Ser Phe Val Asp Gln Ile Leu
        35                  40                  45

Thr Ala Leu Xaa Gly Leu Arg Val Trp Leu Leu Trp Val Val Leu Leu
    50                  55                  60

His
 65

<210> SEQ ID NO 75
<211> LENGTH: 383
<212> TYPE: DNA
<213> ORGANISM: Homo sapiens
<220> FEATURE:
<221> NAME/KEY: modified_base
<222> LOCATION: (1)..(383)
<223> OTHER INFORMATION: human GR21
<223> OTHER INFORMATION: n = g, a, c or t

<400> SEQUENCE: 75
ttatccatta gcatgccatg gtgatttctg acttgacact ggtcacagca attaaaagta      60
aaaagaatgt cacagcacat acacaaatca ggtgcatata gaatttaagg tcaggatatt    120
caagcaatca caaccagtga tattacacca gcatttaaa aatttctttn tgtctgttca    180
gacatgataa cttttctgcc catcattttt tccattctaa tagtggttat atttgttatt    240
gggaaatttg ctaatggctt catagcattg gtaaattcca ttgagtgggt caagagacaa    300
aagatctcct tgttgacca aattctcact gctctgngcg gtctcagagt ntggttgctc    360
tgggtggtat tactacattt gag                                             383

<210> SEQ ID NO 76
<211> LENGTH: 90
<212> TYPE: PRT
<213> ORGANISM: Homo sapiens
<220> FEATURE:
<221> NAME/KEY: MOD_RES
<222> LOCATION: (1)..(90)
<223> OTHER INFORMATION: human GR22
<223> OTHER INFORMATION: Xaa = any amino acid

<400> SEQUENCE: 76

Met Ala Thr Glu Ser Asp Thr Asn Leu Leu Ile Leu Ala Ile Ala Glu
1               5                   10                  15

Phe Ile Ile Ser Met Leu Gly Asn Val Phe Ile Gly Leu Val Asn Cys
            20                  25                  30

Ser Glu Xaa Ile Lys Asn Xaa Lys Val Phe Ser Ala Asp Phe Ile Leu
        35                  40                  45

Thr Cys Leu Ala Ile Ser His Asn Gly Gln Leu Leu Val Ile Leu Phe
    50                  55                  60

Asp Ser Phe Leu Val Gly Leu Ala Ser His Leu Tyr Thr Thr Tyr Arg
65                  70                  75                  80

Leu Xaa Lys Asn Cys Ile Met Leu Trp Thr
                85                  90

<210> SEQ ID NO 77
<211> LENGTH: 656

```
<212> TYPE: DNA
<213> ORGANISM: Homo sapiens
<220> FEATURE:
<221> NAME/KEY: modified_base
<222> LOCATION: (1)..(656)
<223> OTHER INFORMATION: human GR22
<223> OTHER INFORMATION: n = g, a, c or t

<400> SEQUENCE: 77
tatagggacn gtgatgcttc gtacactctc caagaagaaa cactccgtga ggtatgtgag      60
actgcatncc ttagtagatc tnttgggata tatattcata atatagaaaa anaggcaaag     120
acttncttaa gtatatgaga ctctatccaa cagcagaagg ttctgatcaa gactggaagt     180
gcaatanaag caatgaagat aagtatcaga tatgaatgct cttctgcaat ggtctgattg     240
tnacattatt aatgatacan agtattaaaa acttggattt tnttgtctct ggagatggcc     300
accgaatcgg acacaaatct tctgattctg gcaatagcag aattcatcat cagcatgctg     360
gggaatgtgt tcattggact ggtaaactgc tctgaangga tcaagaacca naaggtcttc     420
tcagctgact tcatcctcac ctgcttggct atctctcaca atggacaact gttggtgata     480
ctgtttgatt catttctagt gggacttgct tcacatctat ataccacata tagactanga     540
aaaaactgta ttatgctttg gacatgacta atcacttgac acactgcttc gcacgtgcta     600
gcatattcta ttcttagata gccacttcnc actccttgtc tctgctgaag tgggat        656

<210> SEQ ID NO 78
<211> LENGTH: 72
<212> TYPE: PRT
<213> ORGANISM: Homo sapiens
<220> FEATURE:
<221> NAME/KEY: MOD_RES
<222> LOCATION: (1)..(72)
<223> OTHER INFORMATION: human GR23
<223> OTHER INFORMATION: Xaa = any amino acid

<400> SEQUENCE: 78

Val Ala Phe Val Leu Gly Asn Val Ala Asn Gly Phe Ile Ala Leu Val
 1               5                  10                  15

Asn Val Ile Asp Xaa Val Asn Thr Arg Lys Ile Ser Ser Ala Glu Gln
            20                  25                  30

Ile Leu Thr Ala Leu Val Val Ser Arg Ile Gly Xaa Thr Leu Xaa His
        35                  40                  45

Ser Ile Pro Xaa Asp Ala Thr Arg Cys Xaa Ser Ala Leu Tyr Arg Xaa
    50                  55                  60

Glu Val Arg Ile Val Ala Ser Asn
65                  70

<210> SEQ ID NO 79
<211> LENGTH: 589
<212> TYPE: DNA
<213> ORGANISM: Homo sapiens
<220> FEATURE:
<221> NAME/KEY: modified_base
<222> LOCATION: (1)..(589)
<223> OTHER INFORMATION: human GR23
<223> OTHER INFORMATION: n = g, a, c or t

<400> SEQUENCE: 79
agggttgagt cgtgcttatc ttcacttaac ctagtatana antacagcat atagcaagga      60
gagaatgtat atgaagagga gtgaatttga gtctgtttga gaataatgac cttttctatt     120
tctataaaga cagttttgaa ttcatctatt agcatatgct ggtgcttgcc tgttgacact     180
```

```
agtcactgaa tttaaaggca gaaaatgtta ttgcacattt agtaatcaag tgttcatcga      240
agttaacatc tggatgttaa aggactcaga acaagtgtta ctaagcctgc attttttat       300 ctgttcaaac atgatgtgtt ntctgctcat catttcatca attctggtag agttgcattt      360
gttcttggaa atgtngccaa tggcttcata gctctagtaa atgtcattga ctgngttaac      420
acacgaaaga tctcctcagc tgagcaaatt ctcactgctc tggtggtctc cagaattggt      480
nntactctgn gtcatagtat tccttgagat gcaactagat gttaatctgc tctatatagg      540
ntagaagtaa gaattgttgc ttctaatgcc tgagctcgta cgaaccatt                  589
```

<210> SEQ ID NO 80
<211> LENGTH: 68
<212> TYPE: PRT
<213> ORGANISM: Homo sapiens
<220> FEATURE:
<223> OTHER INFORMATION: human GR24

<400> SEQUENCE: 80

```
Met Ala Thr Glu Leu Asp Lys Ile Phe Leu Ile Met Ala Val Ala Glu
 1               5                  10                  15

Phe Ile Ile Ser Met Leu Gly Asn Val Phe Ile Gly Leu Val Asn Cys
            20                  25                  30

Ser Glu Gly Ile Thr Asn Gln Asn Val Val Leu Ala Asp Phe Ile Leu
        35                  40                  45

Thr Cys Met Ala Ser Leu Thr Ile Gly Gln Leu Val Val Ile Leu Phe
    50                  55                  60

Asp Tyr Phe Leu
 65
```

<210> SEQ ID NO 81
<211> LENGTH: 528
<212> TYPE: DNA
<213> ORGANISM: Homo sapiens
<220> FEATURE:
<221> NAME/KEY: modified_base
<222> LOCATION: (1)..(528)
<223> OTHER INFORMATION: human GR24
<223> OTHER INFORMATION: n = g, a, c or t

<400> SEQUENCE: 81

```
agtcacnnna tgaagactgg ggacctcgta ttcaccnctc tctagagaaa agaaaacact       60
ctcgagaagg tatgtgagac tgcagacctt agtagatctt gtgggattaa gaacagaatt      120
atggtcaaaa taggccaaga cttccttaag tatatgagac tctatccaac agcagaaggt      180
tctgatcaag actggagagg caataaaagc aatgaagata agtatcagat atgaatgctc      240
ttctgcaatg gtgtgattgt aaatttatta atgatacaaa gtattaaaga cttggatttt      300
ttcgtctctg gagatggcca ccgaattgga caaaatcttt ctgattatgg cagtagcaga      360
attcatcatc agcatgctgg ggaatgtgtt cattggactg gtcaactgct ctgaagggat      420
cacaaaccaa aatgtcgttc tagctgactt catactcacc tgcatggcta gtctcacaat      480
tggacaactg gtggtgatac tgtttgatta tttcttgtgt gacttgtg                   528
```

<210> SEQ ID NO 82
<211> LENGTH: 20
<212> TYPE: PRT
<213> ORGANISM: Artificial Sequence
<220> FEATURE:
<223> OTHER INFORMATION: Description of Artificial Sequence:SF family
      consensus sequence 1, transmembrane region 1,
      amino acids encoded by degenerate primer set

```
<220> FEATURE:
<221> NAME/KEY: MOD_RES
<222> LOCATION: (2)
<223> OTHER INFORMATION: Xaa = Phe or Ala
<220> FEATURE:
<221> NAME/KEY: MOD_RES
<222> LOCATION: (3)
<223> OTHER INFORMATION: Xaa = Ile, Val or Leu
<220> FEATURE:
<221> NAME/KEY: MOD_RES
<222> LOCATION: (4)
<223> OTHER INFORMATION: Xaa = Val or Leu
<220> FEATURE:
<221> NAME/KEY: MOD_RES
<222> LOCATION: (6)
<223> OTHER INFORMATION: Xaa = Ile or Val
<220> FEATURE:
<221> NAME/KEY: MOD_RES
<222> LOCATION: (7)
<223> OTHER INFORMATION: Xaa = Leu or Val
<220> FEATURE:
<221> NAME/KEY: MOD_RES
<222> LOCATION: (10)
<223> OTHER INFORMATION: Xaa = Gly or Thr
<220> FEATURE:
<221> NAME/KEY: MOD_RES
<222> LOCATION: (13)
<223> OTHER INFORMATION: Xaa = Val or Ala
<220> FEATURE:
<221> NAME/KEY: MOD_RES
<222> LOCATION: (18)
<223> OTHER INFORMATION: Xaa = Ile or Met

<400> SEQUENCE: 82

Glu Xaa Xaa Xaa Gly Xaa Xaa Gly Asn Xaa Phe Ile Xaa Leu Val Asn
 1               5                  10                  15

Cys Xaa Asp Trp
         20

<210> SEQ ID NO 83
<211> LENGTH: 14
<212> TYPE: PRT
<213> ORGANISM: Artificial Sequence
<220> FEATURE:
<223> OTHER INFORMATION: Description of Artificial Sequence:SF family
      consensus sequence 2, transmembrane region 2,
      amino acids encoded by degenerate primer set
<220> FEATURE:
<221> NAME/KEY: MOD_RES
<222> LOCATION: (1)
<223> OTHER INFORMATION: Xaa = Asp or Gly
<220> FEATURE:
<221> NAME/KEY: MOD_RES
<222> LOCATION: (2)
<223> OTHER INFORMATION: Xaa = Phe or Leu
<220> FEATURE:
<221> NAME/KEY: MOD_RES
<222> LOCATION: (3)
<223> OTHER INFORMATION: Xaa = Ile or Leu
<220> FEATURE:
<221> NAME/KEY: MOD_RES
<222> LOCATION: (5)
<223> OTHER INFORMATION: Xaa = Thr or Ile
<220> FEATURE:
<221> NAME/KEY: MOD_RES
<222> LOCATION: (6)
<223> OTHER INFORMATION: Xaa = Gly, Ala or Ser
<220> FEATURE:
<221> NAME/KEY: MOD_RES
<222> LOCATION: (13)
<223> OTHER INFORMATION: Xaa = Cys, Gly or Phe

<400> SEQUENCE: 83

Xaa Xaa Xaa Leu Xaa Xaa Leu Ala Ile Ser Arg Ile Xaa Leu
 1               5                  10
```

<210> SEQ ID NO 84
<211> LENGTH: 13
<212> TYPE: PRT
<213> ORGANISM: Artificial Sequence
<220> FEATURE:
<223> OTHER INFORMATION: Description of Artificial Sequence:SF family
      consensus sequence 3, transmembrane region 3,
      amino acids encoded by degenerate primer set
<220> FEATURE:
<221> NAME/KEY: MOD_RES
<222> LOCATION: (3)
<223> OTHER INFORMATION: Xaa = Leu or Phe
<220> FEATURE:
<221> NAME/KEY: MOD_RES
<222> LOCATION: (4)
<223> OTHER INFORMATION: Xaa = Ser, Thr or Asn
<220> FEATURE:
<221> NAME/KEY: MOD_RES
<222> LOCATION: (5)
<223> OTHER INFORMATION: Xaa = Leu, Ile or Val
<220> FEATURE:
<221> NAME/KEY: MOD_RES
<222> LOCATION: (7)
<223> OTHER INFORMATION: Xaa = Phe or Leu
<220> FEATURE:
<221> NAME/KEY: MOD_RES
<222> LOCATION: (8)
<223> OTHER INFORMATION: Xaa = Ala or Thr
<220> FEATURE:
<221> NAME/KEY: MOD_RES
<222> LOCATION: (10)
<223> OTHER INFORMATION: Xaa = Cys, Ser or Asn
<220> FEATURE:
<221> NAME/KEY: MOD_RES
<222> LOCATION: (12)
<223> OTHER INFORMATION: Xaa = Ser, Asn or Gly
<220> FEATURE:
<221> NAME/KEY: MOD_RES
<222> LOCATION: (13)
<223> OTHER INFORMATION: Xaa = Ile or Val

<400> SEQUENCE: 84

Asn His Xaa Xaa Xaa Trp Xaa Xaa Thr Xaa Leu Xaa Xaa
 1               5                  10

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence:SF family
      consensus sequence 4, transmembrane region 4,
      amino acids encoded by degenerate primer set
<220> FEATURE:
<221> NAME/KEY: MOD_RES
<222> LOCATION: (3)
<223> OTHER INFORMATION: Xaa = Phe or Cys
<220> FEATURE:
<221> NAME/KEY: MOD_RES
<222> LOCATION: (8)
<223> OTHER INFORMATION: Xaa = Asn or Ser
<220> FEATURE:
<221> NAME/KEY: MOD_RES
<222> LOCATION: (11)
<223> OTHER INFORMATION: Xaa = His or Asn
<220> FEATURE:
<221> NAME/KEY: MOD_RES
<222> LOCATION: (12)
<223> OTHER INFORMATION: Xaa = Pro or Ser
<220> FEATURE:
<221> NAME/KEY: MOD_RES
<222> LOCATION: (13)
<223> OTHER INFORMATION: Xaa = Leu, Ile or Val
<220> FEATURE:
<221> NAME/KEY: MOD_RES -continued
<222> LOCATION: (16)
<223> OTHER INFORMATION: Xaa = Trp or Tyr

<400> SEQUENCE: 85

Phe Tyr Xaa Leu Lys Ile Ala Xaa Phe Ser Xaa Xaa Xaa Phe Leu Xaa
1               5                   10                  15

Leu Lys

<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence:SF family
      consensus sequence 5, transmembrane region 5,
      amino acids encoded by degenerate primer set
<220> FEATURE:
<221> NAME/KEY: MOD_RES
<222> LOCATION: (4)
<223> OTHER INFORMATION: Xaa = Ile, Phe or Val
<220> FEATURE:
<221> NAME/KEY: MOD_RES
<222> LOCATION: (8)
<223> OTHER INFORMATION: Xaa = Lys or Arg
<220> FEATURE:
<221> NAME/KEY: MOD_RES
<222> LOCATION: (10)
<223> OTHER INFORMATION: Xaa = Ser or Thr
<220> FEATURE:
<221> NAME/KEY: MOD_RES
<222> LOCATION: (11)
<223> OTHER INFORMATION: Xaa = Lys or Arg
<220> FEATURE:
<221> NAME/KEY: MOD_RES
<222> LOCATION: (12)
<223> OTHER INFORMATION: Xaa = Gln or Lys
<220> FEATURE:
<221> NAME/KEY: MOD_RES
<222> LOCATION: (13)
<223> OTHER INFORMATION: Xaa = Met or Ile
<220> FEATURE:
<221> NAME/KEY: MOD_RES
<222> LOCATION: (14)
<223> OTHER INFORMATION: Xaa = Gln or Lys

<400> SEQUENCE: 86

Leu Leu Ile Xaa Ser Leu Trp Xaa His Xaa Xaa Xaa Xaa Xaa
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence:SF family
      consensus sequence 6, transmembrane region 7,
      amino acids encoded by degenerate primer set
<220> FEATURE:
<221> NAME/KEY: MOD_RES
<222> LOCATION: (3)
<223> OTHER INFORMATION: Xaa = Phe or Leu
<220> FEATURE:
<221> NAME/KEY: MOD_RES
<222> LOCATION: (4)
<223> OTHER INFORMATION: Xaa = Ile or Val
<220> FEATURE:
<221> NAME/KEY: MOD_RES
<222> LOCATION: (7)
<223> OTHER INFORMATION: Xaa = Leu or Met
<220> FEATURE:
<221> NAME/KEY: MOD_RES
<222> LOCATION: (8)
<223> OTHER INFORMATION: Xaa = Gly, Ser or Thr
<220> FEATURE:

```
<221> NAME/KEY: MOD_RES
<222> LOCATION: (10)
<223> OTHER INFORMATION: Xaa = Pro, Ser or Asn
<220> FEATURE:
<221> NAME/KEY: MOD_RES
<222> LOCATION: (13)
<223> OTHER INFORMATION: Xaa = Lys or Arg
<220> FEATURE:
<221> NAME/KEY: MOD_RES
<222> LOCATION: (14)
<223> OTHER INFORMATION: Xaa = Gln or Arg

<400> SEQUENCE: 87

His Ser Xaa Xaa Leu Ile Xaa Xaa Asn Xaa Lys Leu Xaa Xaa
  1               5                  10

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence:Sf01
      signature sequence 1, amino acids encoded by PCR primers
      identifying polymorphic variants, interspecies
      homologs and alleles of Sf family members

<400> SEQUENCE: 88

Lys Met Ala Pro Leu Asp Leu Leu Leu
  1               5

<210> SEQ ID NO 89
<211> LENGTH: 11
<212> TYPE: PRT
<213> ORGANISM: Artificial Sequence
<220> FEATURE:
<223> OTHER INFORMATION: Description of Artificial Sequence:Sf01
      signature sequence 2, amino acids encoded by PCR primers
      identifying polymorphic variants, interspecies
      homologs and alleles of Sf family members

<400> SEQUENCE: 89

Ala Thr Trp Leu Gly Val Phe Tyr Cys Ala Lys
  1               5                  10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence:Sf01
      signature sequence 3, amino acids encoded by PCR primers
      identifying polymorphic variants, interspecies
      homologs and alleles of Sf family members

<400> SEQUENCE: 90

Leu Ser Ile Leu Ser Phe Leu Ile Leu Tyr
  1               5                  10

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence:Sf01
      signature sequence 4, amino acids encoded by PCR primers
      identifying polymorphic variants, interspecies
      homologs and alleles of Sf family members

<400> SEQUENCE: 91

Leu Ile Leu Gly Asn Pro Lys Leu Lys
```

-continued

```
<210> SEQ ID NO 92
<211> LENGTH: 343
<212> TYPE: DNA
<213> ORGANISM: Rattus sp.
<220> FEATURE:
<223> OTHER INFORMATION: rat GR04 sequence approximately 1100 bp 3' to
      SEQ ID NO:8

<400> SEQUENCE: 92
aagtccagcc ctctccccca caggatttag gtgcagggag ctgtttgacc acttcaattc       60
agtcctgggt gtagaccaga accacaggta aaaagaatg acttcattaa attagcagac       120
aaatgggtgg aactagaaaa tgtcatcctg ggctggagag atggctcagt ggttcagacc      180
actggctgct cttccagagg tcctgagttc aattcccaac aactatatgg tggctaccaa      240
ccattacaat gagatcagat gccctcctct tgtgtatctg aagagagtga cagtgtactt      300
acatacataa aataaataaa taaatctaaa aaaatgttaa aaa                        343
```

METHOD FOR IDENTIFYING COMPOUNDS MODULATING TASTE TRANSDUCTION

CROSS-REFERENCES TO RELATED APPLICATIONS

The present application is a continuation of U.S. Ser. No. 09/393,634, filed Sep 10, 1999, now U.S. Pat No. 6,558,910.

STATEMENT AS TO FEDERALLY SPONSORED RESEARCH AND DEVELOPMENT

This invention was made with government support under Grant No. 5R01 DC03160, awarded by the National Institutes of Health. The government has certain rights in this invention.

FIELD OF THE INVENTION

The invention provides isolated nucleic acid and amino acid sequences of taste cell specific G-protein coupled receptors, antibodies to such receptors, methods of detecting such nucleic acids and receptors, and methods of screening for modulators of taste cell specific G-protein coupled receptors.

BACKGROUND OF THE INVENTION

Taste transduction is one of the most sophisticated forms of chemotransduction in animals (see, e.g., Margolskee, *BioEssays* 15:645-650 (1993); Avenet & Lindemann, *J. Membrane Biol.* 112:1-8 (1989)). Gustatory signaling is found throughout the animal kingdom, from simple metazoans to the most complex of vertebrates; its main purpose is to provide a reliable signaling response to non-volatile ligands. Each of these modalities is though to be mediated by distinct signaling pathways mediated by receptors or channels, leading to receptor cell depolarization, generation of a receptor or action potential, and release of neurotransmitter at gustatory afferent neuron synapses (see, e.g., Roper, *Ann. Rev. Neurosci.* 12:329-353 (1989)).

Mammals are believed to have five basic taste modalities: sweet, bitter, sour, salty, and umami (the taste of monosodium glutamate) (see, e.g., Kawamura & Kare, *Introduction to Umami: A Basic Taste* (1987); Kinnamon & Cummings, *Ann. Rev. Physiol.* 54:715-731(1992); Lindemann, *Physiol. Rev.* 76:718-766 (1996); Stewart et al., *Am. J. Physiol.* 272:1-26 (1997)). Extensive psychophysical studies in humans have reported that different regions of the tongue display different gustatory preferences (see, e.g., Hoffmann, *Menchem. Arch. Path. Anat. Physiol.* 62:516-530 (1875); Bradley et al., *Anatomical Record* 212: 246-249 (1985); Miller & Reedy, *Physiol. Behav.* 47:1213-1219 (1990)). Also, numerous physiological studies in animals have shown that taste receptor cells may selectively respond to different tastants (see, e.g., Akabas et al., Science 242:1047-1050 (1988); Gilbertson et al., *J. Gen. Physiol.* 100:803-24 (1992); Bernhardt et al., *J. Physiol.* 490:325-336 (1996); Cummings et al., *J. Neurophysiol.* 75:1256-1263 (1996)).

In mammals, taste receptor cells are assembled into taste buds that are distributed into different papillae in the tongue epithelium. Circumvallate papillae, found at the very back of the tongue, contain hundreds (mice) to thousands (human) of taste buds and are particularly sensitive to bitter substances. Foliate papillae, localized to the posterior lateral edge of the tongue, contain dozens to hundreds of taste buds and are particularly sensitive to sour and bitter substances. Fungiform papillae containing a single or a few taste buds are at the front of the tongue and are thought to mediate much of the sweet taste modality.

Each taste bud, depending on the species, contains 50-150 cells, including precursor cells, support cells, and taste receptor cells (see, e.g., Lindemann, *Physiol. Rev.* 76:718-766 (1996)). Receptor cells are innervated at their base by afferent nerve endings that transmit information to the taste centers of the cortex through synapses in the brain stem and thalamus. Elucidating the mechanisms of taste cell signaling and information processing is critical for understanding the function, regulation, and "perception" of the sense of taste.

Although much is known about the psychophysics and physiology of taste cell function, very little is known about the molecules and pathways that mediate these sensory signaling responses (reviewed by Gilbertson, *Current Opin. Neurobiol.* 3:532-539 (1993)). Electrophysiological studies suggest that sour and salty tastants modulate taste cell function by direct entry of $H^+$ and $Na^+$ ions through specialized membrane channels on the apical surface of the cell. In the case of sour compounds, taste cell depolarization is hypothesized to result from $H^+$ blockage of $K^+$ channels (see, e.g., Kinnamon et al., *Proc. Nat'l Acad. Sci. USA* 85: 7023-7027 (1988)) or activation of pH-sensitive channels (see, e.g., Gilbertson et al., *J. Gen. Physiol.* 100:803-24 (1992)); salt transduction may be partly mediated by the entry of $Na^+$ via amiloride-sensitive $Na^+$ channels (see, e.g., Heck et al., *Science* 223:403-405 (1984); Brand et al., *Brain Res.* 207-214 (1985); Avenet et al., *Nature* 331: 351-354 (1988)).

Sweet, bitter, and umami transduction are believed to be mediated by G-protein-coupled receptor (GPCR) signaling pathways (see, e.g., Striem et al., *Biochem. J.* 260:121-126 (1989); Chaudhari et al, *J. Neuros.* 16:3817-3826 (1996); Wong et al., *Nature* 381: 796-800 (1996)). Confusingly, there are almost as many models of signaling pathways for sweet and bitter transduction as there are effector enzymes for GPCR cascades (e.g., G protein subunits, cGMP phosphodiesterase, phospholipase C, adenylate cyclase; see, e.g., Kinnamon & Margolskee, *Curr. Opin. Neurobiol.* 6:506-513 (1996)). However, little is known about the specific membrane receptors involved in taste transduction, or many of the individual intracellular signaling molecules activated by the individual taste transduction pathways. Identification of such molecules is important given the numerous pharmacological and food industry applications for bitter antagonists, sweet agonists, and other modulators of taste.

One taste-cell specific G protein that has been identified is called Gustducin (McLaughin et al., *Nature* 357:563-569 (1992)). This protein is proposed to be involved in the detection of certain bitter and sweet tastes (Wong et al., *Nature* 381:796-800 (1996)), and is expressed in a significant subset of cells from all types of taste papillae (McLaughlin et al., *Nature* 357:563-569 (1992)).

Recently, two novel GPCRs were identified and found to be specifically expressed in taste cells. While these receptor proteins, called TR1 and TR2, appear to be directly involved in taste reception (Hoon et al., *Cell* 96:541-551 (1999)), they are only expressed in a fraction of mammalian taste receptor cells. For example, neither of the genes are extensively expressed in Gustducin-expressing cells. Thus, it is clear that additional taste-involved GPCRs remain to be discovered.

Genetic studies in mammals have identified numerous loci that are involved in the detection of taste. For example, psychophysical tasting studies have shown that humans can be categorized as tasters, non-tasters, and super-tasters for the bitter substance PROP (6-n-propylthiouracil), and that PROP tasting may be conferred by a dominant allele, with non-tasters having two recessive alleles and tasters having at least one dominant allele (see Bartoshuk et al., *Physiol Behav* 56(6):1165-71; 58:203-204 (1994)). Recently, a locus involved in PROP tasting has been mapped to human interval 5p15 (Reed et al., *Am. J. Hum. Genet.*, 64(5):1478-80 (1999)). The PROP tasting gene present at the 5p5 locus has yet to be described, however.

In addition, a number of genes involved in taste have been mapped in mice. For example, a cluster of genes involved in bitter-taste detection has been mapped to a region of chromosome 6 in mice (Lush et al., *Genet Res.* 66:167-174 (1995)).

The identification and isolation of novel taste receptors and taste signaling molecules would allow for new methods of pharmacological and genetic modulation of taste transduction pathways. For example, the availability of receptor and channel molecules would permit the screening for high affinity agonists, antagonists, inverse agonists, and modulators of taste cell activity. Such taste modulating compounds would be useful in the pharmaceutical and food industries to customize taste. In addition, such taste cell specific molecules can serve as invaluable tools in the generation of taste topographic maps that elucidate the relationship between the taste cells of the tongue and taste sensory neurons leading to taste centers in the brain.

SUMMARY OF THE INVENTION

The present invention thus provides novel nucleic acids encoding a family of taste-cell specific G-protein coupled receptors. These nucleic acids and the polypeptides that they encode are referred to as the "Sf," or "GR" family of G-protein coupled taste receptors. This novel family of GPCRs includes components of the taste transduction pathway. In particular, members of this family are involved in the detection of bitter tastes.

In one aspect, the present invention provides a method for identifying a compound that modulates taste signaling in taste cells, the method comprising the steps of: (i) contacting the compound with a taste transduction G-protein coupled receptor polypeptide, wherein the polypeptide is expressed in a taste cell, the polypeptide comprising greater than about 60% amino acid sequence identity to a sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80; and (ii) determining the functional effect of the compound upon the polypeptide.

In another aspect, the present invention provides a method for identifying a compound that modulates taste signaling in taste cells, the method comprising the steps of: (i) contacting the compound with a polypeptide comprising an extracellular domain of a taste transduction G-protein coupled receptor, wherein the receptor is expressed in a taste cell, the extracellular domain comprising greater than about 60% amino acid sequence identity to the extracellular domain of a polypeptide comprising a sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80; and (ii) determining the functional effect of the compound upon the extracellular domain.

In another aspect, the present invention provides a method for identifying a compound that modulates taste signaling in taste cells, the method comprising the steps of: (i) contacting the compound with a taste transduction G-protein coupled receptor polypeptide comprising either: (a) a sequence comprising at least about 50% amino acid identity to a sequence selected from the group consisting of SEQ ID NO:82, SEQ ID NO:83, SEQ ID NO:84, SEQ ID NO:85, SEQ ID NO:86, and SEQ ID NO:87; or (b) a sequence selected from the group consisting of SEQ ID NO:88, SEQ ID NO:89, SEQ ID NO:90, and SEQ ID NO:91; and (ii) determining the functional effect of the compound upon the polypeptide.

In one embodiment, the polypeptide has G-protein coupled receptor activity. In another embodiment, the functional effect of the compound upon the polypeptide is determined by measuring changes in intracellular cAMP, cGMP, IP3, or $Ca^{2+}$. In another embodiment, the functional effect is a chemical effect. In another embodiment, the functional effect is a physical effect. In another embodiment, the functional effect is determined by measuring binding of the compound to an extracellular domain of the polypeptide. In another embodiment, the functional effect is determined by measuring radiolabeled GTP binding to the polypeptide. In another embodiment, the functional effect is measured by determining changes in the electrical activity of cells expressing the polypeptides.

In another embodiment, the polypeptide or parts thereof is recombinant. In another embodiment, the polypeptide comprises an extracellular domain that is covalently linked to a heterologous polypeptide, forming a chimeric polypeptide. In another embodiment, the polypeptide is linked to a solid phase, either covalently or non-covalently.

In another embodiment, the polypeptide is from a rat, a mouse, or a human. In another embodiment, the polypeptide is expressed in a cell or a cell membrane. In another embodiment, the cell is a eukaryotic cell. In another embodiment, the polypeptide comprises an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80.

In one aspect, the present invention provides an isolated nucleic acid encoding a taste transduction G-protein coupled receptor, wherein the receptor is expressed in a taste cell, the receptor comprising greater than about 60% amino acid sequence identity to a sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33.

In another aspect, the present invention provides an isolated nucleic acid encoding a taste transduction G-protein coupled receptor, wherein the nucleic acid specifically hybridizes under highly stringent conditions to a nucleic acid having a nucleotide sequence selected from the group consisting of SEQ ID NO:2, SEQ ID NO:4, SEQ ID NO:6, SEQ ID NOS:8 and 92, SEQ ID NO:10; SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and SEQ ID NO:34, but not to a nucleic acid having a nucleotide sequence selected from the group consisting of SEQ ID NO:36, SEQ ID NO:38, SEQ ID NO:40, SEQ ID NO:42, SEQ ID NO:44, SEQ ID NO:46; SEQ ID NO:48, SEQ ID NO:50, SEQ ID NO:52, SEQ ID NO:54, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, and SEQ ID NO:81.

In another aspect, the present invention provides an isolated nucleic acid encoding a taste transduction G-protein coupled receptor, the receptor comprising greater than about 60% amino acid identity to a polypeptide having an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33, wherein the nucleic acid selectively hybridizes under moderately stringent hybridization conditions to a nucleotide sequence having a nucleotide sequence selected from the group consisting of SEQ ID NO:2, SEQ ID NO:4, SEQ ID NO:6, SEQ ID NOS:8 and 92, SEQ ID NO:10; SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and SEQ ID NO:34 but not to a nucleic acid having a nucleotide sequence selected from the group consisting of SEQ ID NO:36, SEQ ID NO:38, SEQ ID NO:40, SEQ ID NO:42, SEQ ID NO:44, SEQ ID NO:46; SEQ ID NO:48, SEQ ID NO:50, SEQ ID NO:52, SEQ ID NO:54, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, and SEQ ID NO:81.

In another aspect, the present invention provides an isolated nucleic acid encoding an extracellular domain of a taste transduction G-protein coupled receptor, wherein the receptor is expressed in a taste cell, the extracellular domain having greater than about 60% amino acid sequence identity to the extracellular domain of a polypeptide comprising an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33.

In one embodiment, the nucleic acid encodes a receptor that specifically binds to polyclonal antibodies generated against a polypeptide having an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33, but not to polyclonal antibodies generated against a polypeptide having an amino acid sequence selected from the group consisting of SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80.

In another embodiment, the nucleic acid encodes a receptor comprising an amino acid sequence of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33.

In another embodiment, the nucleic acid comprises a nucleotide sequence selected from the group consisting of SEQ ID NO:2, SEQ ID NO:4, SEQ ID NO:6, SEQ ID NOS:8 and 92, SEQ ID NO:10; SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, and SEQ ID NO:34.

In another embodiment, the nucleic acid encodes a receptor that has G-protein coupled receptor activity. In another embodiment, the nucleic acid is from a rat or a mouse. In another embodiment, the nucleic acid is amplified by primers that selectively hybridize under stringent hybridization conditions to the same sequence as degenerate primer sets encoding amino acid sequences selected from the group consisting of: KMAPLDLLL (SEQ ID NO:88), ATWLGVFYCAK (SEQ ID NO:89), LSILSFLILY (SEQ ID NO:90), and LILGNPKLK (SEQ ID NO:91).

In one embodiment, the nucleic acid encodes the extracellular domain linked to a heterologous polypeptide, forming a chimeric polypeptide. In another embodiment, the nucleic acid encodes the extracellular domain of a polypeptide comprising an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33.

In another aspect, the present invention provides an isolated taste transduction G-protein coupled receptor, wherein the receptor is expressed in a taste cell, the receptor comprising greater than about 60% amino acid sequence identity to a sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33.

In one embodiment, the receptor specifically binds to polyclonal antibodies generated against a polypeptide having an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33, but not to polyclonal antibodies generated against a polypeptide having an amino acid sequence selected from the group consisting of SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:66, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80. In another embodiment, the receptor has G-protein coupled receptor activity. In another embodiment, the receptor has an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33. In another embodiment, the receptor is from a rat or a mouse.

In one aspect, the present invention provides an isolated polypeptide comprising an extracellular domain of a taste transduction G-protein coupled receptor, wherein the receptor is expressed in a taste cell, the extracellular domain comprising greater than about 60% amino acid sequence identity to the extracellular domain of a polypeptide comprising an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33.

In one embodiment, the polypeptide encodes the extracellular domain of a polypeptide comprising an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33. In another embodiment, the extracellular domain is covalently linked to a heterologous polypeptide, forming a chimeric polypeptide.

In one aspect, the present invention provides an antibody that selectively binds to the receptor comprising greater than about 60% amino acid sequence identity to a sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33.

In another aspect, the present invention provides an expression vector comprising a nucleic acid encoding a taste transduction G-protein coupled receptor, wherein the receptor is expressed in a taste cell, the receptor comprising greater than about 60% amino acid sequence identity to a sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, and SEQ ID NO:33.

In another aspect, the present invention provides a host cell transfected with the expression vector.

BRIEF DESCRIPTION OF THE DRAWINGS

FIG. 1 provides nucleotide sequence, amino acid sequence, and genetic data for various rat, mouse, and human Sf family members (SEQ ID NOS: 1-81).

FIG. 3 provides a comparison of amino acid sequences of some of the various Sf family members (SEQ ID NOS:35, 1, 49, 51, 47, 53, 21, 7, 23, 9, 17, 19, 60, 33, 58, 66, 64, 5, 39, 3, 15, 43 and 41, respectively.

DETAILED DESCRIPTION OF THE INVENTION

I. Introduction

Figure 2:
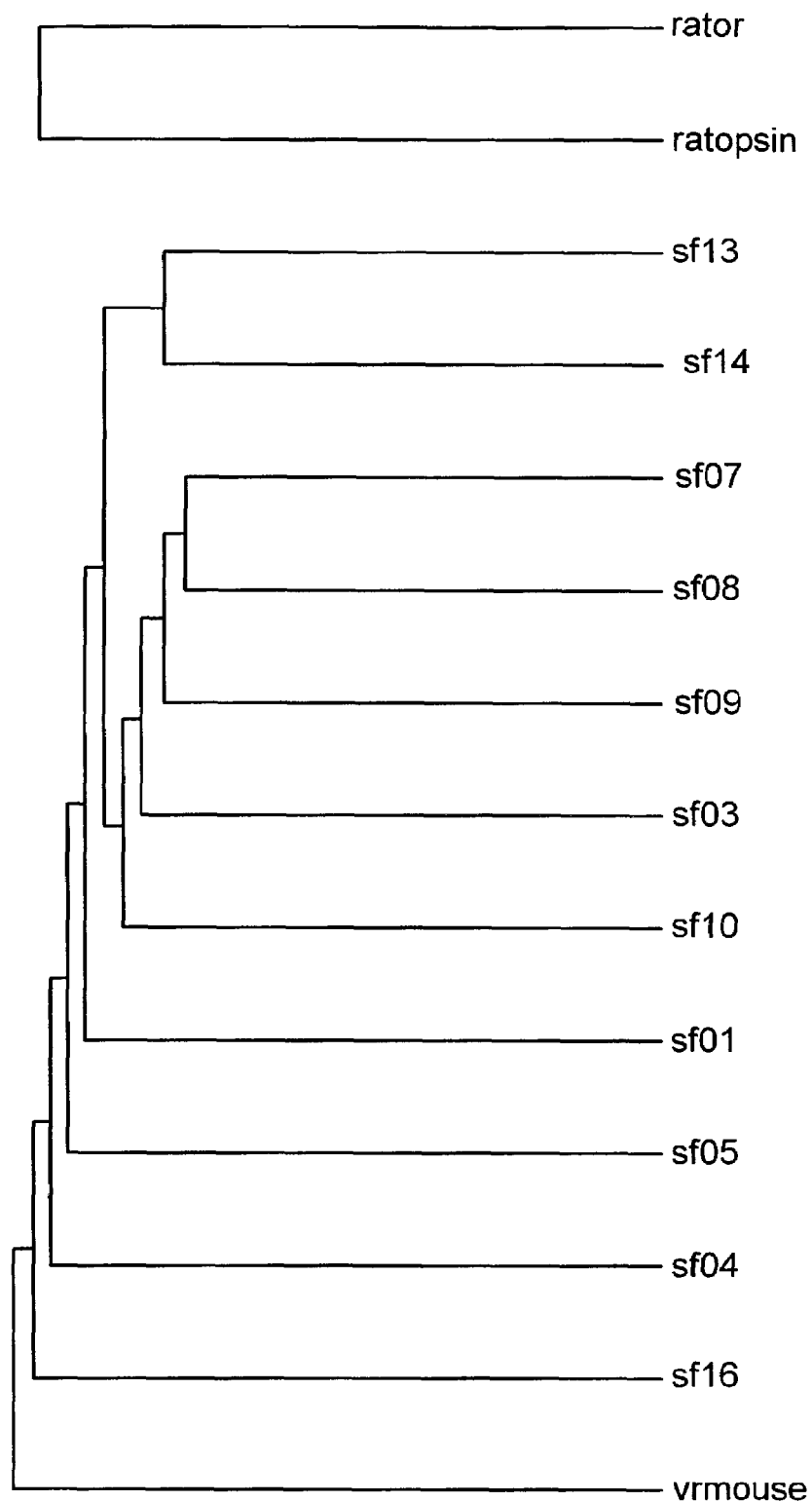
FIG. 2 provides a dendogram showing the relationship between some of the various Sf family members.

The present invention provides nucleic acids encoding a novel family of taste cell specific G-protein coupled receptors. These nucleic acids and the receptors that they encode are referred to as members of the "Sf" family of taste cell specific G protein coupled receptors. These taste cell specific GPCRs are components of the taste transduction pathway, and are involved in the taste detection of substances such as the bitter substances 6-n-propylthiouracil (PROP), sucrose octaacetate (soa), ruffinose acetate (roa), cycloheximide (cyx), and quinine (qui). These nucleic acids provide valuable probes for the identification of taste cells, as the nucleic acids are specifically expressed in taste cells. For example, probes for Sf polypeptides and proteins can be used to identity subsets of taste cells such as foliate cells and circumvallate cells, or specific taste receptor cells, e.g., sweet, sour, salty, and bitter. They also serve as tools for the generation of taste topographic maps that elucidate the relationship between the taste cells of the tongue and taste sensory neurons leading to taste centers in the brain. Furthermore, the nucleic acids and the proteins they encode can be used as probes to dissect taste-induced behaviors.

The invention also provides methods of screening for modulators, e.g., activators, inhibitors, stimulators, enhancers, agonists, and antagonists, of these novel taste cell GPCRs. Such modulators of taste transduction are useful for pharmacological and genetic modulation of taste signaling pathways. These methods of screening can be used to identify high affinity agonists and antagonists of taste cell activity. These modulatory compounds can then be used in the food and pharmaceutical industries to customize taste. Thus, the invention provides assays for taste modulation, where members of the Sf family act as direct or indirect reporter molecules for the effect of modulators on taste transduction. GPCRs can be used in assays, e.g., to measure changes in ligand binding, ion concentration, membrane potential, current flow, ion flux, transcription, signal transduction, receptor-ligand interactions, second messenger concentrations, in vitro, in vivo, and ex vivo. In one embodiment, members of the Sf family can be used as indirect reporters via attachment to a second reporter molecule such as green fluorescent protein (see, e.g., Mistili & Spector, *Nature Biotechnology* 15:961-964 (1997)). In another embodiment, Sf family members are recombinantly expressed in cells, and modulation of taste transduction via GPCR activity is assayed by measuring changes in $Ca^{2+}$ levels and other intracellular messages such as cAMP, cGMP, and IP3.

Methods of assaying for modulators of taste transduction include in vitro ligand binding assays using Sf polypeptides, portions thereof such as the extracellular domain, or chimeric proteins comprising one or more domains of an Sf family member, oocyte Sf gene expression; tissue culture cell Sf gene expression; transcriptional activation of Sf genes; phosphorylation and dephosphorylation of Sf family members; G-protein binding to GPCRs; ligand binding assays; voltage, membrane potential and conductance changes; ion flux assays; changes in intracellular second messengers such as cGMP, cAMP and inositol triphosphate; changes in intracellular calcium levels; and neurotransmitter release.

Finally, the invention provides methods of detecting Sf nucleic acid and protein expression, allowing investigation of taste transduction regulation and specific identification of taste receptor cells. Sf family members also provide useful nucleic acid probes for paternity and forensic investigations. Sf genes are also useful as a nucleic acid probe for identifying subpopulations of taste receptor cells such as foliate, fungiform, and circumvallate taste receptor cells. Sf receptors can also be used to generate monoclonal and polyclonal antibodies useful for identifying taste receptor cells. Taste receptor cells can be identified using techniques such as reverse transcription and amplification of mRNA, isolation of total RNA or poly $A^+$ RNA, northern blotting, dot blotting, in situ hybridization, RNase protection, SI digestion, probing DNA microchip arrays, western blots, and the like.

The Sf genes comprise a large family of related taste cell specific G-multiple protein coupled receptors. Within the genome, these genes are present either alone or within one of several gene clusters. One gene cluster, located at human genomic region 12p 13, comprises at least 9 genes, and a second cluster, located at 7q31, comprises at least 4 genes. In total, 24 distinct Sf family members have been identified, including several putative pseudogenes.

Further, some of the Sf genes are associated with previously mapped mammalian taste-specific loci. For example, the human Sf01 is located at human interval 5p15, precisely where the locus underlying the ability to taste the substance PROP has previously been mapped. In addition, the human gene cluster found at genomic region 12p13 corresponds to a region of mouse chromosome 6 that has been shown to contain numerous bitter-tasting genes, including sucrose octaacetate, ruffinose acetate, cycloheximide, and quinine (see, e.g., Lush et al., Genet. Res. 6:167-174 (1995)). These associations indicate that the Sf genes are involved in the taste detection of various substances, in particular bitter substances.

Functionally, the Sf genes comprise a family of related seven transmembrane G-protein coupled receptors involved in taste transduction, which interact with a G-protein to mediate taste signal transduction (see, e.g., Fong, *Cell Signal* 8:217 (1996); Baldwin, *Curr. Opin. Cell Biol.* 6:180 (1994)).

Structurally, the nucleotide sequence of Sf family members (see, e.g., SEQ ID NOS:2, 4, 6, 8 and 92, 10, 12, 14, 16, 18, 20, 22, 24, 26, 28, 30, 32, 34, 36, 38, 40, 42, 44, 46, 48, 50, 52, 54, 57, 59, 61, 63, 65, 67, 69, 71, 73, 75, 77, 79, and 81, isolated from rats, mice, and humans) encodes a family of related polypeptides comprising an extracellular domain, seven transmembrane domains, and a cytoplasmic domain. Related Sf family genes from other species share at least about 60% nucleotide sequence identity over a region of at least about 50 nucleotides in length, optionally 100, 200, 500, or more nucleotides in length, to SEQ ID NO:2, 4, 6, 8 and 92, 10, 12, 14, 16, 18, 20, 22, 24, 26, 28, 30, 32, 34, 36, 38, 40, 42, 44, 46, 48, 50, 52, 54, 57, 59, 61, 63, 65, 67, 69, 71, 73, 75, 77, 79, or 81, or encode polypeptides sharing at least about 60% amino acid sequence identity over an amino acid region at least about 25 amino acids in length, optionally 50 to 100 amino acids in length to SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 56, 58, 60, 62, 64, 66, 68, 70, 72, 74, 76, 78, or 80. Sf genes are specifically expressed in taste cells.

Figure 3B:
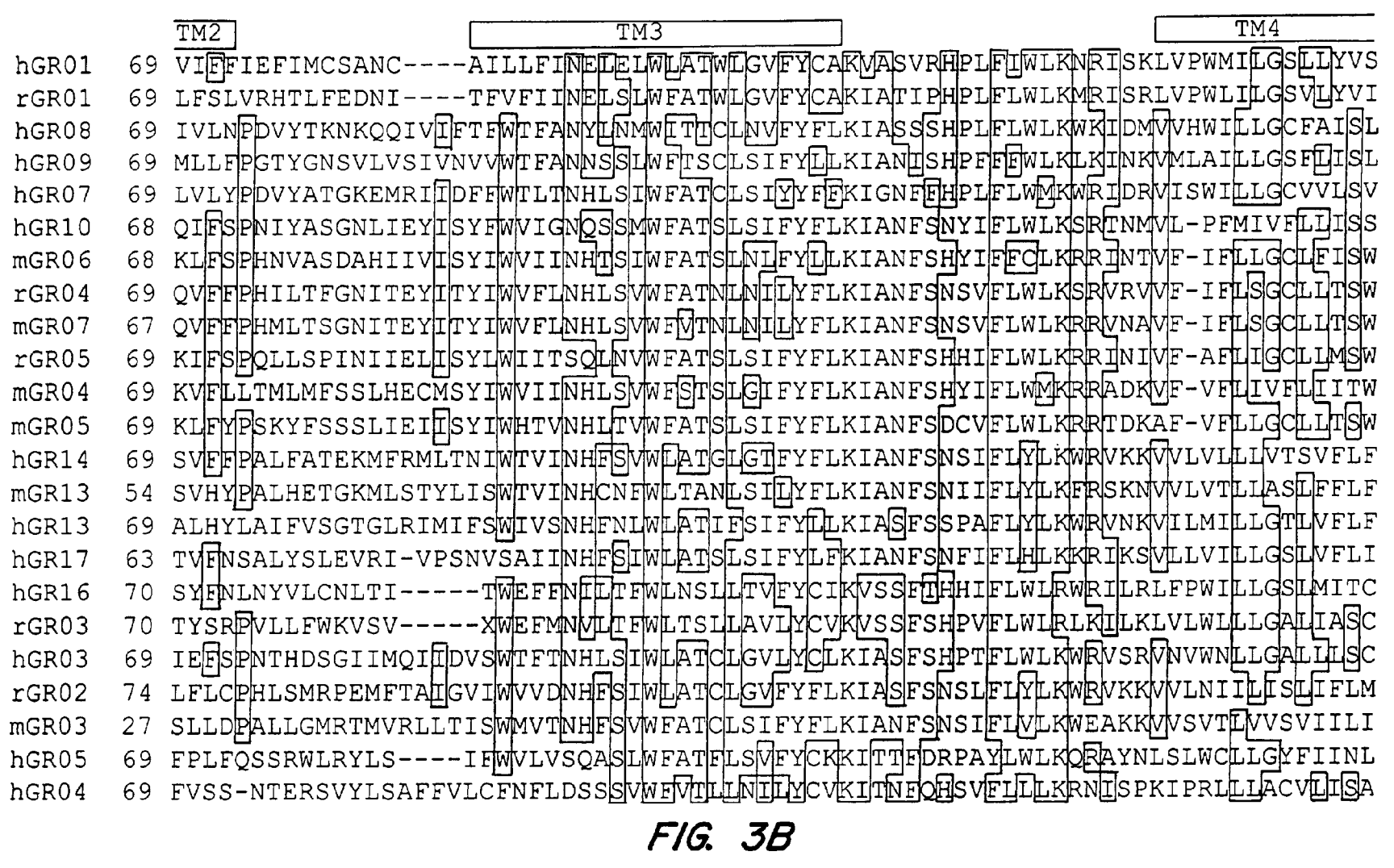
Figure 3D:
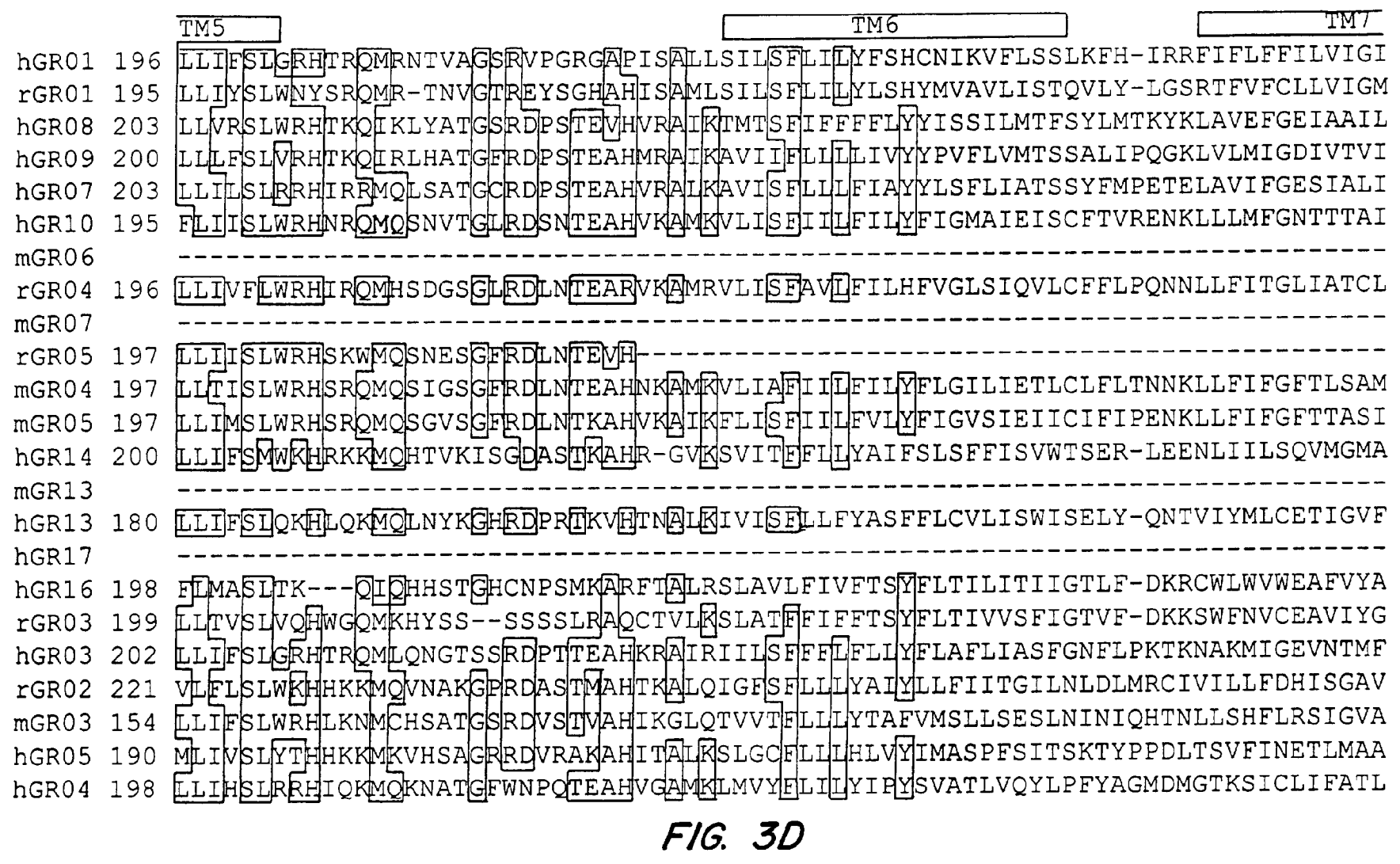

Several consensus amino acid sequences have also been discovered that are characteristic of Sf family members. For example, Sf family members typically comprise a sequence at least about 50% identical to SEQ ID NO:82 (corresponding, e.g., to amino acid positions 16-35 in SEQ ID NOS:1 and 35, see also FIG. 3, transmembrane region 1), 83 (corresponding, e.g., to amino acid positions 45-58 in SEQ ID NOS:1 and 35, see also FIG. 3, transmembrane region 2), 84 (corresponding, e.g., to amino acid positions 89-101 in SEQ ID NOS:1 and 35, see also FIG. 3, transmembrane region 3), 85 (corresponding, e.g., to amino acid positions 102-119 in SEQ ID NOS:1 and 35, see also FIG. 3, transmembrane region 4), 86 (corresponding, e.g., to amino acid positions 195-208 in SEQ ID NO:1, and to amino acid positions 196-209 in SEQ ID NO:35, see also FIG. 3, transmembrane region 5), or 87 (corresponding, e.g., to amino acid positions 271-284 in SEQ ID NO:1, and to amino acid positions 273-286 in SEQ ID NO:35, see also FIG. 3, transmembrane region 7).

One Sf gene, Sf01, has been identified in numerous species, including in rats (SEQ ID NOS:1, 2 for amino acid and nucleotide sequence, respectively) and humans (SEQ ID NO:35, 36 for amino acid and nucleotide sequence, respectively), and can be defined according to one or more Sf01 (also referred to as GR01) signature sequences. Accordingly, GR01 polypeptides typically comprise an amino acid sequence shown as SEQ ID NO:88 (corresponding, e.g., to amino acid positions 40-48 in SEQ ID NOS:1 and 35), 89 (corresponding, e.g., to amino acid positions 96-106 in SEQ ID NOS:1 and 35), 90 (corresponding, e.g., to amino acid positions 226-235 in SEQ ID NO: 1, and to positions 228-237 in SEQ ID NO: 35), or 91 (corresponding, e.g., to amino acid positions 275-283 in SEQ ID NO:1, and to positions 277-285 in SEQ ID NO: 35).

The present invention also provides polymorphic variants of the SF protein depicted in SEQ ID NO:1: variant #1, in which an isoleucine residue is substituted for a leucine residue at amino acid position 7; and variant #2, in which an alanine residue is substituted for a glycine residue at amino acid position 20.

The present invention also provides polymorphic variants of the SF protein depicted in SEQ ID NO:3: variant #1, in which a tyrosine residue is substituted for a phenylalanine residue at amino acid position 2; and variant #2, in which a valine residue is substituted for an isoleucine residue at amino acid position 62.

The present invention also provides polymorphic variants of the SF protein depicted in SEQ ID NO:5: variant #1, in which a glutamine residue is substituted for an asparagine residue at amino acid position 179; and variant #2, in which a cysteine residue is substituted for a methionine residue at amino acid position 183.

The present invention also provides polymorphic variants of the SF protein depicted in SEQ ID NO:7: variant #1, in which a glycine residue is substituted for an alanine residue at amino acid position 4; and variant #2, in which a leucine residue is substituted for an isoleucine residue at amino acid position 64.

The present invention also provides polymorphic variants of the SF protein depicted in SEQ ID NO:9: variant #1, in which a valine residue is substituted for an isoleucine residue at amino acid position 56; and variant #2, in which a methionine residue is substituted for a cysteine residue at amino acid position 57.

The present invention also provides polymorphic variants of the SF protein depicted in SEQ ID NO:11: variant #1, in which an isoleucine residue is substituted for a leucine residue at amino acid position 2; and variant #2, in which an arginine residue is substituted for a lysine residue at amino acid position 7.

The present invention also provides polymorphic variants of the SF protein depicted in SEQ ID NO:13: variant #1, in which a threonine residue is substituted for a serine residue at amino acid position 2; and variant #2, in which an isoleucine residue is substituted for a valine residue at amino acid position 5.

The present invention also provides polymorphic variants of the SF protein depicted in SEQ ID NO:15: variant #1, in which an isoleucine residue is substituted for a leucine residue at amino acid position 61; and variant #2, in which an arginine residue is substituted for a lysine residue at amino acid position 68.

The present invention also provides polymorphic variants of the SF protein depicted in SEQ ID NO:17: variant #1, in which a glycine residue is substituted for an alanine residue at amino acid position 4; and variant #2, in which a phenylalanine residue is substituted for a tryptophan residue at amino acid position 60.

The present invention also provides polymorphic variants of the SF protein depicted in SEQ ID NO:19: variant #1, in which an isoleucine residue is substituted for a leucine residue at amino acid position 62; and variant #2, in which an alanine residue is substituted for a glycine residue at amino acid position 244.

The present invention also provides polymorphic variants of the SF protein depicted in SEQ ID NO:21: variant #1, in which a serine residue is substituted for a threonine residue at amino acid position 3; and variant #2, in which a lysine residue is substituted for an arginine residue at amino acid position 123.

The present invention also provides polymorphic variants of the SF protein depicted in SEQ ID NO:23: variant #1, in which an asparagine residue is substituted for a glutamine residue at amino acid position 63; and variant #2, in which a leucine residue is substituted for an isoleucine residue at amino acid position 59.

The present invention also provides polymorphic variants of the SF protein depicted in SEQ ID NO:25: variant #1, in which an isoleucine residue is substituted for a leucine residue at amino acid position 2; and variant #2, in which an aspartic acid residue is substituted for a glutamic acid residue at amino acid position 4.

The present invention also provides polymorphic variants of the SF protein depicted in SEQ ID NO:27: variant #1, in which an isoleucine residue is substituted for a leucine residue at amino acid position 16; and variant #2, in which an arginine residue is substituted for a lysine residue at amino acid position 46.

The present invention also provides polymorphic variants of the SF protein depicted in SEQ ID NO:29: variant #1, in which a threonine residue is substituted for a serine residue at amino acid position 9; and variant #2, in which a tryptophan residue is substituted for a phenylalanine residue at amino acid position 14.

The present invention also provides polymorphic variants of the SF protein depicted in SEQ ID NO:31: variant #1, in which an isoleucine residue is substituted for a leucine residue at amino acid position 5; and variant #2, in which an arginine residue is substituted for a lysine residue at amino acid position 60.

The present invention also provides polymorphic variants of the SF protein depicted in SEQ ID NO:33: variant #1, in which an isoleucine residue is substituted for a leucine residue at amino acid position 60; and variant #2, in which a histidine residue is substituted for a lysine residue at amino acid position 65.

The present invention also provides polymorphic variants of the SF protein depicted in SEQ ID NO:35: variant #1, in which an isoleucine residue is substituted for a leucine residue at amino acid position 6; and variant #2, in which a glycine residue is substituted for an alanine residue at amino acid position 13.

The present invention also provides polymorphic variants of the SF protein depicted in SEQ ID NO:37: variant #1, in which a leucine residue is substituted for an isoleucine residue at amino acid position 11; and variant #2, in which a threonine residue is substituted for a serine residue at amino acid position 15.

The present invention also provides polymorphic variants of the SF protein depicted in SEQ ID NO:39: variant #1, in which an isoleucine residue is substituted for a valine residue at amino acid position 8; and variant #2, in which an asparagine residue is substituted for a glutamine residue at amino acid position 16.

The present invention also provides polymorphic variants of the SF protein depicted in SEQ ID NO:41: variant #1, in which a lysine residue is substituted for an arginine residue at amino acid position 3; and variant #2, in which an alanine residue is substituted for a glycine residue at amino acid position 20.

The present invention also provides polymorphic variants of the SF protein depicted in SEQ ID NO:43: variant #1, in which an isoleucine residue is substituted for a leucine residue at amino acid position 6; and variant #2, in which an alanine residue is substituted for a glycine residue at amino acid position 23.

The present invention also provides polymorphic variants of the SF protein depicted in SEQ ID NO:45: variant #1, in which a leucine residue is substituted for an isoleucine residue at amino acid position 12; and variant #2, in which a aspartic acid residue is substituted for a glutamic acid residue at amino acid position 16.

The present invention also provides polymorphic variants of the SF protein depicted in SEQ ID NO:47: variant #1, in which an isoleucine residue is substituted for a leucine residue at amino acid position 10; and variant #2, in which a glycine residue is substituted for an alanine residue at amino acid position 25.

The present invention also provides polymorphic variants of the SF protein depicted in SEQ ID NO:49: variant #1, in which a tryptophan residue is substituted for a phenylalanine residue at amino acid position 9; and variant #2, in which an alanine residue is substituted for a glycine residue at amino acid position 25.

The present invention also provides polymorphic variants of the SF protein depicted in SEQ ID NO:51: variant #1, in which a serine residue is substituted for a threonine residue at amino acid position 18; and variant #2, in which a leucine residue is substituted for an isoleucine residue at amino acid position 33.

The present invention also provides polymorphic variants of the SF protein depicted in SEQ ID NO:53: variant #1, in which an isoleucine residue is substituted for a leucine residue at amino acid position 2; and variant #2, in which an alanine residue is substituted for a glycine residue at amino acid position 7.

The present invention also provides polymorphic variants of the SF protein depicted in SEQ ID NO:55: variant #1, in which an arginine residue is substituted for a lysine residue at amino acid position 6; and variant #2, in which a leucine residue is substituted for a valine residue at amino acid position 26.

The present invention also provides polymorphic variants of the SF protein depicted in SEQ ID NO:56: variant #1, in which a leucine residue is substituted for an isoleucine residue at amino acid position 4; and variant #2, in which a lysine residue is substituted for an arginine residue at amino acid position 11.

The present invention also provides polymorphic variants of the SF protein depicted in SEQ ID NO:58: variant #1, in which a threonine residue is substituted for a serine residue at amino acid position 37; and variant #2, in which a glutamic acid residue is substituted for an aspartic acid residue at amino acid position 45.

The present invention also provides polymorphic variants of the SF protein depicted in SEQ ID NO:60: variant #1, in which an isoleucine residue is substituted for a leucine residue at amino acid position 61; and variant #2, in which an arginine residue is substituted for a lysine residue at amino acid position 123.

The present invention also provides polymorphic variants of the SF protein depicted in SEQ ID NO:62: variant #1, in which an isoleucine residue is substituted for a leucine residue at amino acid position 5; and variant #2, in which an alanine residue is substituted for a glycine residue at amino acid position 57.

The present invention also provides polymorphic variants of the SF protein depicted in SEQ ID NO:64: variant #1, in which a serine residue is substituted for a threonine residue at amino acid position 182; and variant #2, in which an isoleucine residue is substituted for a leucine residue at amino acid position 185.

The present invention also provides polymorphic variants of the SF protein depicted in SEQ ID NO:66: variant #1, in which an alanine residue is substituted for a glycine residue at amino acid position 14; and variant #2, in which a phenylalanine residue is substituted for a tryptophan residue at amino acid position 60.

The present invention also provides polymorphic variants of the SF protein depicted in SEQ ID NO:68: variant #1, in which a leucine residue is substituted for an isoleucine residue at amino acid position 5; and variant #2, in which a glycine residue is substituted for an alanine residue at amino acid position 13.

The present invention also provides polymorphic variants of the SF protein depicted in SEQ ID NO:70: variant #1, in which a glycine residue is substituted for an alanine residue at amino acid position 61; and variant #2, in which a valine residue is substituted for a leucine residue at amino acid position 65.

The present invention also provides polymorphic variants of the SF protein depicted in SEQ ID NO:72: variant #1, in which a lysine residue is substituted for an arginine residue at amino acid position 4; and variant #2, in which a leucine residue is substituted for a valine residue at amino acid position 60.

The present invention also provides polymorphic variants of the SF protein depicted in SEQ ID NO:74: variant #1, in which an isoleucine residue is substituted for a leucine residue at amino acid position 5; and variant #2, in which an alanine residue is substituted for a glycine residue at amino acid position 53.

The present invention also provides polymorphic variants of the SF protein depicted in SEQ ID NO:76: variant #1, in which a glutamic acid residue is substituted for an aspartic acid residue at amino acid position 6; and variant #2, in which an isoleucine residue is substituted for a leucine residue at amino acid position 63.

The present invention also provides polymorphic variants of the SF protein depicted in SEQ ID NO:78: variant #1, in which an isoleucine residue is substituted for a valine residue at amino acid position 4; and variant #2, in which a glycine residue is substituted for an alanine residue at amino acid position 9.

The present invention also provides polymorphic variants of the SF protein depicted in SEQ ID NO:80: variant #1, in which an isoleucine residue is substituted for a leucine residue at amino acid position 5; and variant #2, in which an alanine residue is substituted for a glycine residue at amino acid position 57.

Specific regions of the Sf nucleotide and amino acid sequences may be used to identify polymorphic variants, interspecies homologs, and alleles of Sf family members. This identification can be made in vitro, e.g., under stringent hybridization conditions or PCR (e.g., using primers encoding SEQ ID NOS:88-91) and sequencing, or by using the sequence information in a computer system for comparison with other nucleotide sequences. Typically, identification of polymorphic variants and alleles of Sf family members is made by comparing an amino acid sequence of about 25 amino acids or more, e.g., 50-100 amino acids. Amino acid identity of approximately at least 60% or above, optionally 65%, 70%, 75%, 80%, 85%, or 90-95% or above typically demonstrates that a protein is a polymorphic variant, interspecies homolog, or allele of an Sf family member. Sequence comparison can be performed using any of the sequence comparison algorithms discussed below. Antibodies that bind specifically to Sf polypeptides or a conserved region thereof can also be used to identify alleles, interspecies homologs, and polymorphic variants.

Polymorphic variants, interspecies homologs, and alleles of Sf genes are confirmed by examining taste cell specific expression of the putative Sf polypeptide. Typically, Sf polypeptides having an amino acid sequence of SEQ ID NO:1, SEQ ID NO:3, SEQ ID NO:5; SEQ ID NO:7, SEQ ID NO:9, SEQ ID NO:11, SEQ ID NO:13, SEQ ID NO:15,SEQ ID NO:17,SEQ ID NO:19,SEQ ID NO:21,SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, or SEQ ID NO:80 is used as a positive control in comparison to the putative Sf protein to demonstrate the identification of a polymorphic variant or allele of the Sf family member. The polymorphic variants, alleles and interspecies homologs are expected to retain the seven transmembrane structure of a G-protein coupled receptor.

Nucleotide and amino acid sequence information for Sf family members may also be used to construct models of taste cell specific polypeptides in a computer system. These models are subsequently used to identify compounds that can activate or inhibit Sf receptor proteins. Such compounds that modulate the activity of Sf family members can be used to investigate the role of Sf genes in taste transduction.

The isolation of Sf family members provides a means for assaying for inhibitors and activators of G-protein coupled receptor taste transduction. Biologically active Sf proteins are useful for testing inhibitors and activators of Sf as taste transducers using in vivo and in vitro assays that measure, e.g., transcriptional activation of Sf; ligand binding; phosphorylation and dephosphorylation; binding to G-proteins; G-protein activation; regulatory molecule binding; voltage, membrane potential and conductance changes; ion flux; intracellular second messengers such as cGMP, cAMP and inositol triphosphate; intracellular calcium levels; and neurotransmitter release. Such activators and inhibitors identified using Sf family members can be used to further study taste transduction and to identify specific taste agonists and antagonists. Such activators and inhibitors are useful as pharmaceutical and food agents for customizing taste.

The present invention also provides assays, preferably high throughput assays, to identify molecules that interact with and/or modulate an SF polypeptide. In numerous assays, a particular domain of an SF family member is used, e.g., an extracellular, transmembrane, or intracellular domain. In numerous embodiments, an extracellular domain is bound to a solid substrate, and used, e.g., to isolate ligands, agonists, antagonists, or any other molecule that can bind to and/or modulate the activity of an extracellular domain of an SF polypeptide. In certain embodiments, a domain of an SF polypeptide, e.g., an extracellular, transmembrane, or intracellular domain, is fused to a heterologous polypeptide, thereby forming a chimeric polypeptide, e.g., a chimeric polypeptide with G protein coupled receptor activity. Such chimeric polypeptides are useful, e.g., in assays to identify ligands, agonists, antagonists, or other modulators of an SF polypeptide. In addition, such chimeric polypeptides are useful to create novel taste receptors with novel ligand binding specificity, modes of regulation, signal transduction pathways, or other such properties, or to create novel taste receptors with novel combinations of ligand binding specificity, modes of regulation, signal transduction pathways, etc.

Methods of detecting Sf nucleic acids and expression of SF polypeptides are also useful for identifying taste cells and creating topological maps of the tongue and the relation of tongue taste receptor cells to taste sensory neurons in the brain. Chromosome localization of the genes encoding human Sf genes can be used to identify diseases, mutations, and traits caused by and associated with Sf family members.

II. Definitions

As used herein, the following terms have the meanings ascribed to them unless specified otherwise. "Taste cells" include neuroepithelial cells that are organized into groups to form taste buds of the tongue, e.g., foliate, fungiform, and circumvallate cells (see, e.g., Roper et al., *Ann. Rev. Neurosci.* 12:329-353 (1989)). Taste cells also include cells of the palate, and other tissues that may contain taste cells such as the esophagus and the stomach.

"Sf" refers to one or more members of a family of G-protein coupled receptors that are expressed in taste cells such as foliate, fungiform, and circumvallate cells, as well as cells of the palate, esophagus, and stomach (see, e.g., Hoon et al., *Cell* 96:541-551 (1999), herein incorporated by reference in its entirety). Such taste cells can be identified because they express specific molecules such as Gustducin, a taste cell specific G protein, or other taste specific molecules (McLaughin et al., *Nature* 357:563-569 (1992)). Taste receptor cells can also be identified on the basis of morphology (see, e.g., Roper, supra). Sf family members have the ability to act as receptors for taste transduction. Sf family members are also referred to as the "GR" family, for gustatory receptor.

"Sf" nucleic acids encode a family of GPCRs with seven transmembrane regions that have "G-protein coupled receptor activity," e.g., they bind to G-proteins in response to extracellular stimuli and promote production of second messengers such as IP3, cAMP, cGMP, and $Ca^{2+}$ via stimulation of enzymes such as phospholipase C and adenylate cyclase (for a description of the structure and function of GPCRs, see, e.g., Fong, supra, and Baldwin, supra). A dendogram providing the relationship between certain Sf family members is provided as FIG. 2. These nucleic acids encode proteins that are expressed in taste cells, such as The term "Sf" family therefore refers to polymorphic variants, alleles, mutants, and interspecies homologs that: (1) have about 60% amino acid sequence identity, optionally about 75, 80, 85, 90, or 95% amino acid sequence identity to SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, or SEQ ID NO:80 over a window of about 25 amino acids, optionally 50-100 amino acids; (2) specifically bind to antibodies raised against an immunogen comprising an amino acid sequence selected from the group consisting of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80, and conservatively modified variants thereof; (3) specifically hybridize (with a size of at least about 100, optionally at least about 500-1000 nucleotides) under stringent hybridization conditions to a sequence selected from the group consisting of SEQ ID NO:2, SEQ ID NO:4, SEQ ID NO:6, SEQ ID NOS:8 and 92, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, and SEQ ID NO:81, and conservatively modified variants thereof; (4) comprise a sequence at least about 50% identical to an amino acid sequence selected from the group consisting of SEQ ID NO:82, SEQ ID NO:83, SEQ ID NO:84, SEQ ID NO:85, SEQ ID NO:86, and SEQ ID NO:53; or (5) are amplified by primers that specifically hybridize under stringent hybridization conditions to the same sequence as a degenerate primer sets encoding SEQ ID NOS:88, 89, 90, or 91.

Sf01, or GR01, refers to a specific member of the Sf family that has been identified in rat (SEQ ID NOS:1, 2), mouse (SEQ ID NO:11, 12), and human (SEQ ID NOS:35, 36). Accordingly, "Sf01," "SF01," or "GR01" refers to a nucleic acid comprising a sequence comprising at least about 60%, 65%, 70%, 80%, 85%, 90-95%, or more nucleotide sequence identity to SEQ ID NO:2, SEQ ID NO:12, or SEQ ID NO:36, or to a polypeptide comprising an amino acid sequence at least about 60%, 65%, 70%, 80%, 85%, 90-95%, or more identical to SEQ ID NO:1, SEQ ID NO:11, or SEQ ID NO:35, or comprising an amino acid sequence at least about 90%, 95%, 99%, or more amino acid sequence identity to SEQ ID NO:88, SEQ ID NO:89, SEQ ID NO:90, or SEQ ID NO:91.

Topologically, sensory GPCRs have an "N-terminal domain" "extracellular domains," a "transmembrane domain" comprising seven transmembrane regions, cytoplasmic, and extracellular loops, "cytoplasmic domains," and a "C-terminal domain" (see, e.g., Hoon et al., *Cell* 96:541-551 (1999); Buck & Axel, *Cell* 65:175-187 (1991)). These domains can be structurally identified using methods known to those of skill in the art, such as sequence analysis programs that identify hydrophobic and hydrophilic domains (see, e.g., Stryer, *Biochemistry* (3rd ed. 1988); see also any of a number of Internet based sequence analysis programs, such as those found at dot.imgen.bcm.tmc.edu). Such domains are useful for making chimeric proteins and for in vitro assays of the invention, e.g., ligand binding assays. "Extracellular domains" therefore refers to the domains of Sf polypeptides that protrude from the cellular membrane and are exposed to the extracellular face of the cell. Such domains would include the "N terminal domain" that is exposed to the extracellular face of the cell, as well as the extracellular loops of the transmembrane domain that are exposed to the extracellular face of the cell, i.e., the loops between transmembrane regions 2 and 3, and between transmembrane regions 4 and 5. The "N terminal domain" region starts at the N-terminus and extends to a region close to the start of the transmembrane domain. These extracellular domains are useful for in vitro ligand binding assays, both soluble and solid phase.

"Transmembrane domain," which comprises the seven transmembrane regions, refers to the domain of Sf polypeptides that lies within the plasma membrane, and may also include the corresponding cytoplasmic (intracellular) and extracellular loops. The seven transmembrane regions can be identified using standard methods, as described in Kyte & Doolittle, *J. Mol. Biol.* 157:105-132 (1982)), or in Stryer, supra.

"Cytoplasmic domains" refers to the domains of Sf proteins that face the inside of the cell, e.g., the "C terminal domain" and the intracellular loops of the transmembrane domain, e.g., the intracellular loops between transmembrane regions 1 and 2, and the intracellular loops between transmembrane regions 3 and 4. "C terminal domain" refers to the region that spans the end of the last transmembrane domain and the C-terminus of the protein, and which is normally located within the cytoplasm.

"Biological sample" as used herein is a sample of biological tissue or fluid that contains one or more Sf nucleic acids encoding one or more Sf proteins. Such samples include, but are not limited to, tissue isolated from humans, mice, and rats, in particular, tongue, palate, and other tissues that may contain taste cells such as the esophagus and the stomach. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as chimpanzees or humans. Tissues include tongue tissue, isolated taste buds, and testis tissue.

"GPCR activity" refers to the ability of a GPCR to transduce a signal. Such activity can be measured in a heterologous cell, by coupling a GPCR (or a chimeric GPCR) to either a G-protein or promiscuous G-protein such as Gα15, and an enzyme such as PLC, and measuring increases in intracellular calcium using (Offermans & Simon, *J. Biol. Chem.* 270: 15175-15180 (1995)). Receptor activity can be effectively measured by recording ligand-induced changes in $[Ca^{2+}]_i$ using fluorescent $Ca^{2+}$-indicator dyes and fluorometric imaging. Optionally, the polypeptides of the invention are involved in sensory transduction, optionally taste transduction in taste cells.

The phrase "functional effects" in the context of assays for testing compounds that modulate Sf family member mediated taste transduction includes the determination of any parameter that is indirectly or directly under the influence of the receptor, e.g., functional, physical and chemical effects. It includes ligand binding, changes in ion flux, membrane potential, current flow, transcription, G-protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such increases or decreases of neurotransmitter or hormone release.

By "determining the functional effect" is meant assays for a compound that increases or decreases a parameter that is indirectly or directly under the influence of an Sf family member, e.g., functional, physical and chemical effects. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte Sf gene expression; tissue culture cell Sf expression; transcriptional activation of Sf genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like.

"Inhibitors," "activators," and "modulators" of Sf genes or proteins are used interchangeably to refer to inhibitory, activating, or modulating molecules identified using in vitro and in vivo assays for taste transduction, e.g., ligands, agonists, antagonists, and their homologs and mimetics. Inhibitors are compounds that, e.g., bind to, partially or totally block stimulation, decrease, prevent, delay activation, inactivate, desensitize, or down regulate taste transduction, e.g., antagonists. Activators are compounds that, e.g., bind to, stimulate, increase, open, activate, facilitate, enhance activation, sensitize or up regulate taste transduction, e.g., agonists. Modulators include compounds that, e.g., alter the interaction of a receptor with: extracellular proteins that bind activators or inhibitor (e.g., ebnerin and other members of the hydrophobic carrier family); G-proteins; kinases (e.g., homologs of rhodopsin kinase and beta adrenergic receptor kinases that are involved in deactivation and desensitization of a receptor); and arrestin-like proteins, which also deactivate and desensitize receptors. Modulators include genetically modified versions of Sf family members, e.g., with altered activity, as well as naturally occurring and synthetic ligands, antagonists, agonists, small chemical molecules and the like. Such assays for inhibitors and activators include, e.g., expressing Sf family members in cells or cell membranes, applying putative modulator compounds, and then determining the functional effects on taste transduction, as described above. Samples or assays comprising Sf family members that are treated with a potential activator, inhibitor, or modulator are compared to control samples without the inhibitor, activator, or modulator to examine the extent of inhibition. Control samples (untreated with inhibitors) are assigned a relative Sf activity value of 100%. Inhibition of an Sf is achieved when the Sf activity value relative to the control is about 80%, optionally 50% or 25-0%. Activation of an Sf is achieved when the Sf activity value relative to the control is 110%, optionally 150%, optionally 200-500%, or 1000-3000% higher.

"Biologically active" Sf refers to an Sf having GPCR activity as described above, involved in taste transduction in taste receptor cells.

The terms "isolated" "purified" or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated Sf nucleic acid is separated from open reading frames that flank the Sf gene and encode proteins other than an Sf. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (O);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" or a "detectable moiety" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment (see, e.g., FIG. 2). PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395 (1984)).

Another example of algorithm that is suitable for determining percent sequence identity and sequence similarity are the Blast and Blast 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the website of the National Center for Biotechnology Information (ncbi.nlm.nih.gov). This algorithm involves first identifying high scoring sequence pairs (HSPs) by identifying short words of length W in the querry sequence, which either match or satify some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acids sequences, a scoreing is used to calculate the cumulative score. Extension of the word hits in each direction sre halted when: the cumulative alignment score falls off by the quantity X from its maximum achieced value; the cumulative score goes to zero or below, due to the accumulation of one or more negative-scoring residue alignments; or the end of either sequence is reached. The BLAST algorithm parameters W, T, and X determined the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP programs uses as defaults a worldlength of 3, and expecatation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point $(T_m)$ for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5× SSC, and 1% SDS, incubating at 42° C., or, 5× SSC, 1% SDS, incubating at 65° C., with wash in 0.2× SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H 1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-Sf" antibody is an antibody or antibody fragment that specifically binds a polypeptide encoded by an Sf gene, cDNA, or a subsequence thereof.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to an Sf family member from specific species such as rat, mouse, or human can be selected to obtain only those polyclonal antibodies that are specifically immunoreactive with the Sf protein and not with other proteins, except for polymorphic variants and alleles of the Sf protein. This selection may be achieved by subtracting out antibodies that cross-react with Sf molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

III. Isolation of Nucleic Acids Encoding Sf Family Members

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is by either native acrylamide gel electrophoresis or by anion-exchange BPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981).

B. Cloning Methods for the Isolation of Nucleotide Sequences Encoding Sf Family Members In general, the nucleic acid sequences encoding Sf family members and related nucleic acid sequence homologs are cloned from cDNA and genomic DNA libraries by hybridization with probes, or isolated using amplification techniques with oligonucleotide primers. For example, Sf sequences are typically isolated from mammalian nucleic acid (genomic or cDNA) libraries by hybridizing with a nucleic acid probe, the sequence of which can be derived from SEQ ID NO:2, SEQ ID NO:4, SEQ ID NO:6, SEQ ID NOS:8, and 92 SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81. A suitable tissue from which RNA and cDNA for Sf family members can be isolated is tongue tissue, optionally taste bud tissues or individual taste cells.

Amplification techniques using primers can also be used to amplify and isolate Sf sequences from DNA or RNA. For example, degenerate primers encoding the following amino acid sequences can be used to amplify a sequence of an Sf gene: SEQ ID NOS: 50, 51, 52, or 53 (see, e.g., Dieffenfach & Dveksler, *PCR Primer: A Laboratory Manual* (1995)). These primers can be used, e.g., to amplify either the full length sequence or a probe of one to several hundred nucleotides, which is then used to screen a mammalian library for full-length Sf clones. In addition, degenerate primers encoding the following amino acid sequences can be used to amplify a sequence of an Sf01 (GR01) gene: SEQ ID NOS: 88, 89, 90, or 91. As described above, such primers can be used to isolate a full length sequence, or a probe which can then be used to isolated a full length sequence, e.g., from a library.

Nucleic acids encoding Sf can also be isolated from expression libraries using antibodies as probes. Such polyclonal or monoclonal antibodies can be raised using the sequence of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, or SEQ ID NO:80.

Polymorphic variants, alleles, and interspecies homologs that are substantially identical to an Sf family member can be isolated using Sf nucleic acid probes, and oligonucleotides under stringent hybridization conditions, by screening libraries. Alternatively, expression libraries can be used to clone Sf family members and Sf family member polymorphic variants, alleles, and interspecies homologs, by detecting expressed homologs immunologically with antisera or purified antibodies made against an Sf polypeptide, which also recognize and selectively bind to the Sf homolog.

To make a cDNA library, one should choose a source that is rich in Sf mRNA, e.g., tongue tissue, or isolated taste buds. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, Science 196:180-182 (1977). Colony hybridization is carried out as generally described in Grunstein et al., *Proc. Natl. Acad. Sci. USA.*, 72:3961-3965 (1975).

An alternative method of isolating Sf nucleic acid and its homologs combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of Sf genes directly from mRNA, from cDNA, from genomic libraries or cDNA libraries. Degenerate oligonucleotides can be designed to amplify Sf family member homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of Sf-encoding mRNA in physiological samples, for nucleic acid sequencing, or for other purposes. Genes amplified by the PCR reaction can be purified from agarose gels and cloned into an appropriate vector.

Gene expression of Sf family members can also be analyzed by techniques known in the art, e.g., reverse transcription and amplification of mRNA, isolation of total RNA or poly $A^+$ RNA, northern blotting, dot blotting, in situ hybridization, RNase protection, probing DNA microchip arrays, and the like. In one embodiment, high density oligonucleotide analysis technology (e.g., GeneChip™) is used to identify homologs and polymorphic variants of the GPCRs of the invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

Synthetic oligonucleotides can be used to construct recombinant Sf genes for use as probes or for expression of protein. This method is performed using a series of overlapping oligonucleotides usually 40-120 bp in length, representing both the sense and nonsense strands of the gene. These DNA fragments are then annealed, ligated and cloned. Alternatively, amplification techniques can be used with precise primers to amplify a specific subsequence of the Sf nucleic acid. The specific subsequence is then ligated into an expression vector.

The nucleic acid encoding an Sf gene is typically cloned into intermediate vectors before transformation into prokaryotic or eukaryotic cells for replication and/or expression. These intermediate vectors are typically prokaryote vectors, e.g., plasmids, or shuttle vectors.

Optionally, nucleic acids encoding chimeric proteins comprising an Sf polypeptide or domains thereof can be made according to standard techniques. For example, a domain such as a ligand binding domain, an extracellular domain, a transmembrane domain (e.g., one comprising seven transmembrane regions and corresponding extracellular and cytosolic loops), the transmembrane domain and a cytoplasmic domain, an active site, a subunit association region, etc., can be covalently linked to a heterologous protein. For example, an extracellular domain can be linked to a heterologous GPCR transmembrane domain, or a heterologous GPCR extracellular domain can be linked to a transmembrane domain. Other heterologous proteins of choice include, e.g., green fluorescent protein, β-gal, glutamate receptor, and the rhodopsin presequence.

C. Expression in Prokaryotes and Eukaryotes

To obtain high level expression of a cloned gene or nucleic acid, such as those cDNAs encoding an Sf family member, one typically subclones the Sf sequence into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the Sf protein are available in, e.g., *E. coli, Bacillus* sp., and *Salmonella* (Palva et al., *Gene* 22:229-235 (1983); Mosbach et al., *Nature* 302: 543-545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the Sf-encoding nucleic acid in host cells. A typical expression cassette thus contains a promoter operably linked to the nucleic acid sequence encoding an Sf and signals required for efficient polyadenylation of the transcript, ribosome binding sites, and translation termination. The nucleic acid sequence encoding an Sf may typically be linked to a cleavable signal peptide sequence to promote secretion of the encoded protein by the transformed cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/$A^+$, pMTO10/$A^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as neomycin, hymidine kinase, hygromycin B phosphotransferase, and dihydrofolate reductase. Alternatively, high yield expression systems not involving gene amplification are also suitable, such as using a baculovirus vector in insect cells, with a sequence encoding an Sf family member under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of an Sf protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing an Sf gene.

After the expression vector is introduced into the cells, the transfected cells are cultured under conditions favoring expression of the Sf family member, which is recovered from the culture using standard techniques identified below.

IV. Purification of Sf Polypeptides

Either naturally occurring or recombinant Sf polypeptides can be purified for use in functional assays. Optionally, recombinant Sf polypeptides are purified. Naturally occurring Sf polypeptides are purified, e.g., from mammalian tissue such as tongue tissue, and any other source of an Sf homolog. Recombinant Sf polypeptides are purified from any suitable bacterial or eukaryotic expression system, e.g., CHO cells or insect cells.

Sf proteins may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant Sf family members are being purified. For example, proteins having established molecular adhesion properties can be reversibly fused to the Sf polypeptide. With the appropriate ligand, an Sf can be selectively adsorbed to a purification column and then freed from the column in a relatively pure form. The fused protein is then removed by enzymatic activity. Finally Sf proteins can be purified using immunoaffinity columns.

A. Purification of Sf Protein from Recombinant Cells

Recombinant proteins are expressed by transformed bacteria or eukaryotic cells such as CHO cells or insect cells in large amounts, typically after promoter induction; but expression can be constitutive. Promoter induction with IPTG is a one example of an inducible promoter system. Cells are grown according to standard procedures in the art. Fresh or frozen cells are used for isolation of protein.

Proteins expressed in bacteria may form insoluble aggregates ("inclusion bodies"). Several protocols are suitable for purification of Sf inclusion bodies. For example, purification of inclusion bodies typically involves the extraction, separation and/or purification of inclusion bodies by disruption of bacterial cells, e.g., by incubation in a buffer of 50 mM TRISIHCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Sf polypeptides are separated from other bacterial proteins by standard separation techniques, e.g., with Ni-NTA agarose resin.

Alternatively, it is possible to purify Sf polypeptides from bacteria periplasm. After lysis of the bacteria, when an Sf protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying Sf Polypeptides

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of an Sf protein can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

Sf proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of Sf Polypeptides

In addition to the detection of Sf genes and gene expression using nucleic acid hybridization technology, one can also use immunoassays to detect Sf, e.g., to identify taste receptor cells and variants of Sf family members. Immunoassays can be used to qualitatively or quantitatively analyze the Sf. A general overview of the applicable technology can be found in Harlow & Lane, *Antibodies: A Laboratory Manual* (1988).

A. Antibodies to Sf Family Members

Methods of producing polyclonal and monoclonal antibodies that react specifically with an Sf family member are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of Sf-comprising immunogens may be used to produce antibodies specifically reactive with an Sf family member. For example, a recombinant Sf protein, or an antigenic fragment thereof, is isolated as described herein. Suitable antigenic regions include, e.g., the conserved motifs that are used to identify members of the Sf family and the Sf01 gene, i.e., SEQ ID NO:82, SEQ ID NO:83, SEQ ID NO:84; SEQ ID NO:85, SEQ ID NO:86, SEQ ID NO:87; SEQ ID NO:88, SEQ ID NO:89, SEQ ID NO:90, and SEQ ID NO:91. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the Sf. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-Sf proteins, or even other Sf family members or other related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better.

Once Sf family member specific antibodies are available, individual Sf proteins can be detected by a variety of immunoassay methods. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

Sf proteins can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case an Sf family member or an antigenic subsequence thereof). The antibody (e.g., anti-Sf) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled Sf polypeptide or a labeled anti-Sf antibody. Alternatively, the labeling agent may be a third moiety, such a secondary antibody, that specifically binds to the antibody/Sf complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973);

Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 110° C. to 40° C.

Non-Competitive Assay Formats

Immunoassays for detecting an Sf protein in a sample may be either competitive or noncompetitive. Noncompetitive immunoassays are assays in which the amount of antigen is directly measured. In one preferred "sandwich" assay, for example, the anti-Sf antibodies can be bound directly to a solid-substrate on which they are immobilized. These immobilized antibodies then capture the Sf protein present in the test sample. The Sf protein is thus immobilized is then bound by a labeling agent, such as a second Sf antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of Sf protein present in the sample is measured indirectly by measuring the amount of a known, added (exogenous) Sf protein displaced (competed away) from an anti-Sf antibody by the unknown Sf protein present in a sample. In one competitive assay, a known amount of Sf protein is added to a sample and the sample is then contacted with an antibody that specifically binds to the Sf. The amount of exogenous Sf protein bound to the antibody is inversely proportional to the concentration of Sf protein present in the sample. In a particularly preferred embodiment, the antibody is immobilized on a solid substrate. The amount of Sf protein bound to the antibody may be determined either by measuring the amount of Sf protein present in a Sf/antibody complex, or alternatively by measuring the amount of remaining uncomplexed protein. The amount of Sf protein may be detected by providing a labeled Sf molecule.

A hapten inhibition assay is another preferred competitive assay. In this assay the known Sf protein is immobilized on a solid substrate. A known amount of anti-Sf antibody is added to the sample, and the sample is then contacted with the immobilized Sf. The amount of anti-Sf antibody bound to the known immobilized Sf protein is inversely proportional to the amount of Sf protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a protein at least partially encoded by SEQ ID NO:2, SEQ ID NO:4, SEQ ID NO:6, SEQ ID NOS:8 and 92 SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81 can be immobilized to a solid support. Proteins (e.g., Sf proteins and homologs) are added to the assay that compete for binding of the antisera to the immobilized antigen. The ability of the added proteins to compete for binding of the antisera to the immobilized protein is compared to the ability of the Sf polypeptide encoded by SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81 to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs. In addition, peptides representing the conserved motifs that are used to identify members of the Sf family and the Sf01 gene can be used in cross-reactivity determinations, i.e., SEQ ID NO:82, SEQ ID NO:83, SEQ ID NO:84; SEQ ID NO:85, SEQ ID NO:86, SEQ ID NO:87; SEQ ID NO:88, SEQ ID NO:89, SEQ ID NO:90, and SEQ ID NO:91 The immunoabsorbed and pooled antisera are then used in a competitive binding immunoassay as described above to compare a second protein, thought to be perhaps an allele or polymorphic variant of an Sf family member, to the immunogen protein (i.e., Sf protein encoded by SEQ ID NO:2, SEQ ID NO:4, SEQ ID NO:6, SEQ ID NOS:8 and 92 SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2, SEQ ID NO:4, SEQ ID NO:6, SEQ ID NOS:8 and 92 SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81 that is required to inhibit 50% of binding, then the second protein is said to specifically bind to the polyclonal antibodies generated to an SF immunogen.

Polyclonal antibodies that specifically bind to a particular member of the SF family, e.g., SF01, can be make by subtracting out cross-reactive antibodies using other SF family members. Species-specific polyclonal antibodies can be made in a similar way. For example, antibodies specific to human SF01 can be made by subtracting out antibodies that are cross-reactive with rat or mouse SF01.

Other Assay Formats

Western blot (immunoblot) analysis is used to detect and quantify the presence of Sf protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the Sf protein. The anti-Sf polypeptide antibodies specifically bind to the Sf polypeptide on the solid support. These antibodies may be directly labeled or alternatively may be subsequently detected using labeled antibodies (e.g., labeled sheep anti-mouse antibodies) that specifically bind to the anti-Sf antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize an Sf protein, or secondary antibodies that recognize anti-Sf.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of Sf Family Members

A. Assays for Sf Protein Activity

Sf family members and their alleles and polymorphic variants are G-protein coupled receptors that participate in taste transduction. The activity of Sf polypeptides can be assessed using a variety of in vitro and in vivo assays to determine functional, chemical, and physical effects, e.g., measuring ligand binding (e.g., radioactive ligand binding), second messengers (e.g., cAMP, cGMP, $IP_3$, DAG, or $Ca^{2+}$), ion flux, phosphorylation levels, transcription levels, neurotransmitter levels, and the like. Furthermore, such assays can be used to test for inhibitors and activators of Sf family members. Modulators can also be genetically altered versions of Sf receptors.

Such modulators of taste transduction activity are useful for customizing taste.

The Sf protein of the assay will be selected from a polypeptide having a sequence of SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, or SEQ ID NO:80 or conservatively modified variant thereof. Alternatively, the Sf protein of the assay will be derived from a eukaryote and include an amino acid subsequence having amino acid sequence identity to SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, or SEQ ID NO:91. Generally, the amino acid sequence identity will be at least 60%, optionally at least 70% to 85%, optionally at least 90-95%. Optionally, the polypeptide of the assays will comprise a domain of an Sf protein, such as an extracellular domain, transmembrane domain, cytoplasmic domain, ligand binding domain, subunit association domain, active site, and the like. Either the Sf protein or a domain thereof can be covalently linked to a heterologous protein to create a chimeric protein used in the assays described herein.

Modulators of Sf receptor activity are tested using Sf polypeptides as described above, either recombinant or naturally occurring. The protein can be isolated, expressed in a cell, expressed in a membrane derived from a cell, expressed in tissue or in an animal, either recombinant or naturally occurring. For example, tongue slices, dissociated cells from a tongue, transformed cells, or membranes can b used. Modulation is tested using one of the in vitro or in vivo assays described herein. Taste transduction can also be examined in vitro with soluble or solid state reactions, using a full-length SF-GPCR or a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to an Sf protein, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

Receptor-G-protein interactions can also be examined. For example, binding of the G-protein to the receptor or its release from the receptor can be examined. For example, in the absence of GTP, an activator will lead to the formation of a tight complex of a G protein (all three subunits) with the receptor. This complex can be detected in a variety of ways, as noted above. Such an assay can be modified to search for inhibitors. Add an activator to the receptor and G protein in the absence of GTP, form a tight complex, and then screen for inhibitors by looking at dissociation of the receptor-G protein complex. In the presence of GTP, release of the alpha subunit of the G protein from the other two G protein subunits serves as a criterion of activation.

An activated or inhibited G-protein will in turn alter the properties of target enzymes, channels, and other effector proteins. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For example, compounds that modulate the duration a taste receptor stays active would be useful as a means of prolonging a desired taste or cutting off an unpleasant one. For a general review of GPCR signal transduction and methods of assaying signal transduction, see, e.g., *Methods in Enzymology*, vols. 237 and 238 (1994) and volume 96 (1983); Bourne et al., *Nature* 10:349:117-27 (1991); Bourne et al., Nature 348:125-32 (1990); Pitcher et al., *Annu. Rev. Biochem.* 67:653-92 (1998).

Samples or assays that are treated with a potential Sf protein inhibitor or activator are compared to control samples without the test compound, to examine the extent of modulation. Control samples (untreated with activators or inhibitors) are assigned a relative Sf activity value of 100. Inhibition of an Sf protein is achieved when the Sf activity value relative to the control is about 90%, optionally 50%, optionally 25-0%. Activation of an Sf protein is achieved when the Sf activity value relative to the control is 110%, optionally 150%, 200-500%, or 1000-2000%.

Changes in ion flux may be assessed by determining changes in polarization (i.e., electrical potential) of the cell or membrane expressing an Sf protein. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336: 1575-1595 (1997)). Whole cell currents are conveniently determined using the standard methodology (see, e.g., Hamil et al., *P Flugers. Archiv.* 391:85 (1981). Other known assays include: radiolabeled ion flux assays and fluorescence assays using voltage-sensitive dyes (see, e.g., Vestergarrd-Bogind et al., *J. Membrane Biol.* 88:67-75 (1988); Gonzales & Tsien, *Chem. Biol.* 4:269-277 (1997); Daniel et al., *J. Pharmacol. Meth.* 25:185-193 (1991); Holevinsky et al., *J. Membrane*

*Biology* 137:59-70 (1994)). Generally, the compounds to be tested are present in the range from 1 µM to 100 mM.

The effects of the test compounds upon the function of the polypeptides can be measured by examining any of the parameters described above. Any suitable physiological change that affects GPCR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3, cGMP, or cAMP.

Preferred assays for G-protein coupled receptors include cells that are loaded with ion or voltage sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as Gα15 and Gα16 can be used in the assay of choice (Wilkie et al., *Proc. Nat'l Acad. Sci. USA* 88:10049-10053 (1991)). Such promiscuous G-proteins allow coupling of a wide range of receptors.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine, *Nature* 312:315-21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting enzymes such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl. Acad. Sci. U.S.A.* 88:9868-9872 (1991) and Dhallan et al., *Nature* 347:184-187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-crated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In a preferred embodiment, Sf protein activity is measured by expressing an Sf gene in a heterologous cell with a promiscuous G-protein that links the receptor to a phospholipase C signal transduction pathway (see Offermanns & Simon, *J. Biol. Chem.* 270:15175-15180 (1995)). Optionally the cell line is HEK-293 (which does not naturally express Sf genes) and the promiscuous G-protein is Gα15 (Offermanns & Simon, supra). Modulation of taste transduction is assayed by measuring changes in intracellular $Ca^{2+}$ levels, which change in response to modulation of the Sf signal transduction pathway via administration of a-molecule that associates with an Sf protein. Changes in $Ca^{2+}$ levels are optionally measured using fluorescent $Ca^{2+}$-indicator dyes and fluorometric imaging.

In one embodiment, the changes in intracellular cAMP or cGMP can be measured using immunoassays. The method described in Offermanns & Simon, *J. Biol. Chem.* 270:15175-15180 (1995) may be used to determine the level of cAMP. Also, the method described in Felley-Bosco et al., *Am. J. Resp. Cell and Mol. Biol.* 11:159-164 (1994) may be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^3$H-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

In another embodiment, transcription levels can be measured to assess the effects of a test compound on signal transduction. A host cell containing an Sf protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using reporter gene may be used as described in U.S. Pat. No. 5,436,128, herein incorporated by reference. The reporter genes can be, e.g., chloramphenicol acetyltransferase, luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961-964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

B. Modulators

The compounds tested as modulators of an Sf family member can be any small chemical compound, or a biological entity, such as a protein, sugar, nucleic acid or lipid. Alternatively, modulators can be genetically altered versions of an Sf gene. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

C. Solid State and Soluble High Throughput Assays

In one embodiment the invention provide soluble assays using molecules such as a domain such as ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; an Sf protein; or a cell or tissue expressing an Sf protein, either naturally occurring or recombinant. In another embodiment, the invention provides solid phase based in vitro assays in a high throughput format, where the domain, chimeric molecule, Sf protein, or cell or tissue expressing the Sf is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100- about 1500 different compounds. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

D. Computer-Based Assays

Yet another assay for compounds that modulate Sf protein activity involves computer assisted drug design, in which a computer system is used to generate a three-dimensional structure of an Sf protein based on the structural information encoded by its amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., ligands. These regions are then used to identify ligands that bind to the protein.

The three-dimensional structural model of the protein is generated by entering protein amino acid sequences of at least 10 amino acid residues or corresponding nucleic acid sequences encoding an Sf polypeptide into the computer system. The nucleotide sequence encoding the polypeptide, or the amino acid sequence thereof, is preferably selected from the group consisting of SEQ ID NO:2, SEQ ID NO:4, SEQ ID NO:6, SEQ ID NOS:8 and 92 SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, or SEQ ID NO:81; or SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, or SEQ ID NO:80, respectively, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the Sf protein to identify ligands that bind to the protein. Binding affinity between the protein and ligands is determined using energy terms to determine which ligands have an enhanced probability of binding to the protein.

Computer systems are also used to screen for mutations, polymorphic variants, alleles and interspecies homologs of Sf genes. Such mutations can be associated with disease states or genetic traits. As described above, GeneChipm and related technology can also be used to screen for mutations, polymorphic variants, alleles and interspecies homologs. Once the variants are identified, diagnostic assays can be used to identify patients having such mutated genes. Identification of the mutated Sf genes involves receiving input of a first nucleic acid or amino acid sequence of an Sf gene selected from the group consisting of SEQ ID NO:2, SEQ ID NO:4, SEQ ID NO:6, SEQ ID NOS:8 and 92 SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, and SEQ ID NO:81; or SEQ ID NO:1, SEQ ID NO:3, SEQ ID NO:5; SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, and SEQ ID NO:80, respectively, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various Sf genes, and mutations associated with disease states and genetic traits.

VIII. Kits

Sf genes and their homologs are useful tools for identifying taste receptor cells, for forensics and paternity determinations, and for examining taste transduction. Sf family member-specific reagents that specifically hybridize to Sf nucleic acids, such as Sf probes and primers, and Sf specific reagents that specifically bind to an Sf protein, e.g., Sf antibodies are used to examine taste cell expression and taste transduction regulation.

Nucleic acid assays for the presence of DNA and RNA for an Sf family member in a sample include numerous techniques are known to those skilled in the art, such as Southern analysis, northern analysis, dot blots, RNase protection, Sl analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230-250 (1986); Haase et al., *Methods in Virology*, vol. VII, pp. 189-226 (1984); and *Nucleic Acid Hybridization: A Practical Approach* (Hames et al., eds. 1987). In addition, an Sf protein can be detected with the various immunoassay techniques described above. The test sample is typically compared to both a positive control (e.g., a sample expressing a recombinant Sf protein) and a negative control.

The present invention also provides for kits for screening for modulators of Sf family members. Such kits can be prepared from readily available materials and reagents. For example, such kits can comprise any one or more of the following materials: Sf nucleic acids or proteins, reaction tubes, and instructions for testing Sf activity. Optionally, the kit contains a biologically active Sf receptor. A wide variety of kits and components can be prepared according to the present invention, depending upon the intended user of the kit and the particular needs of the user.

IX. Administration and Pharmaceutical Compositions

Taste modulators can be administered directly to the mammalian subject for modulation of taste in vivo. Administration is by any of the routes normally used for introducing a modulator compound into ultimate contact with the tissue to be treated, optionally the tongue or mouth. The taste modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences,* $17^{th}$ ed. 1985)).

The taste modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, by orally, topically, intravenously, intraperitoneally, intravesically or intrathecally. Optionally, the compositions are administered orally or nasally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. The dose will be determined by the efficacy of the particular taste modulators employed and the condition of the subject, as well as the body weight or surface area of the area to be treated. The size of the dose also will be determined by the existence, nature, and extent of any adverse side-effects that accompany the administration of a particular compound or vector in a particular subject.

In determining the effective amount of the modulator to be administered in a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, taste modulators of the present invention can be administered at a rate determined by the LD-50 of the modulator, and the side-effects of the inhibitor at various concentrations, as applied to the mass and overall health of the subject. Administration can be accomplished via single or divided doses.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example I—Identification of Human Sf01

Figure 1A:
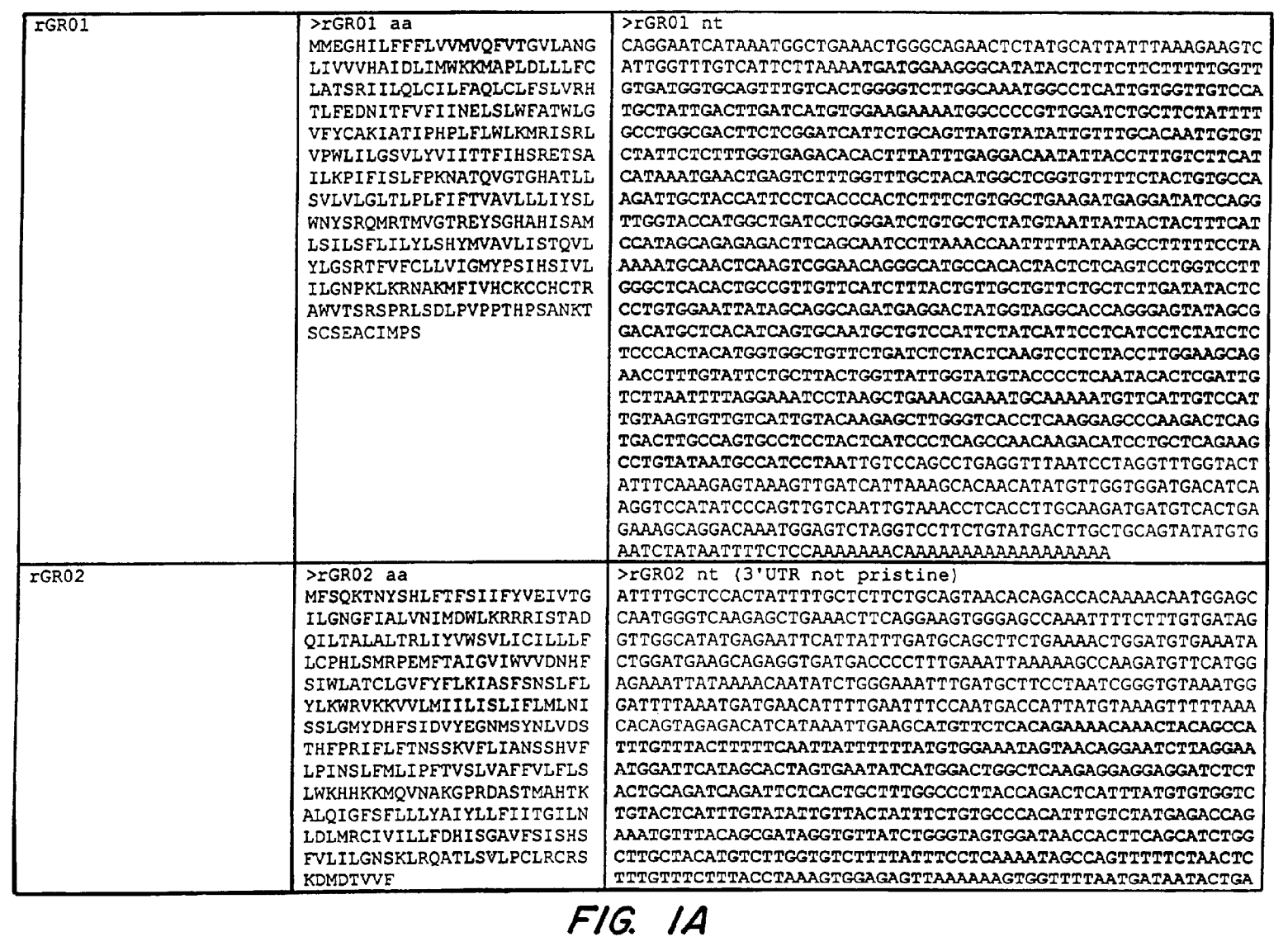
Figure 1G:
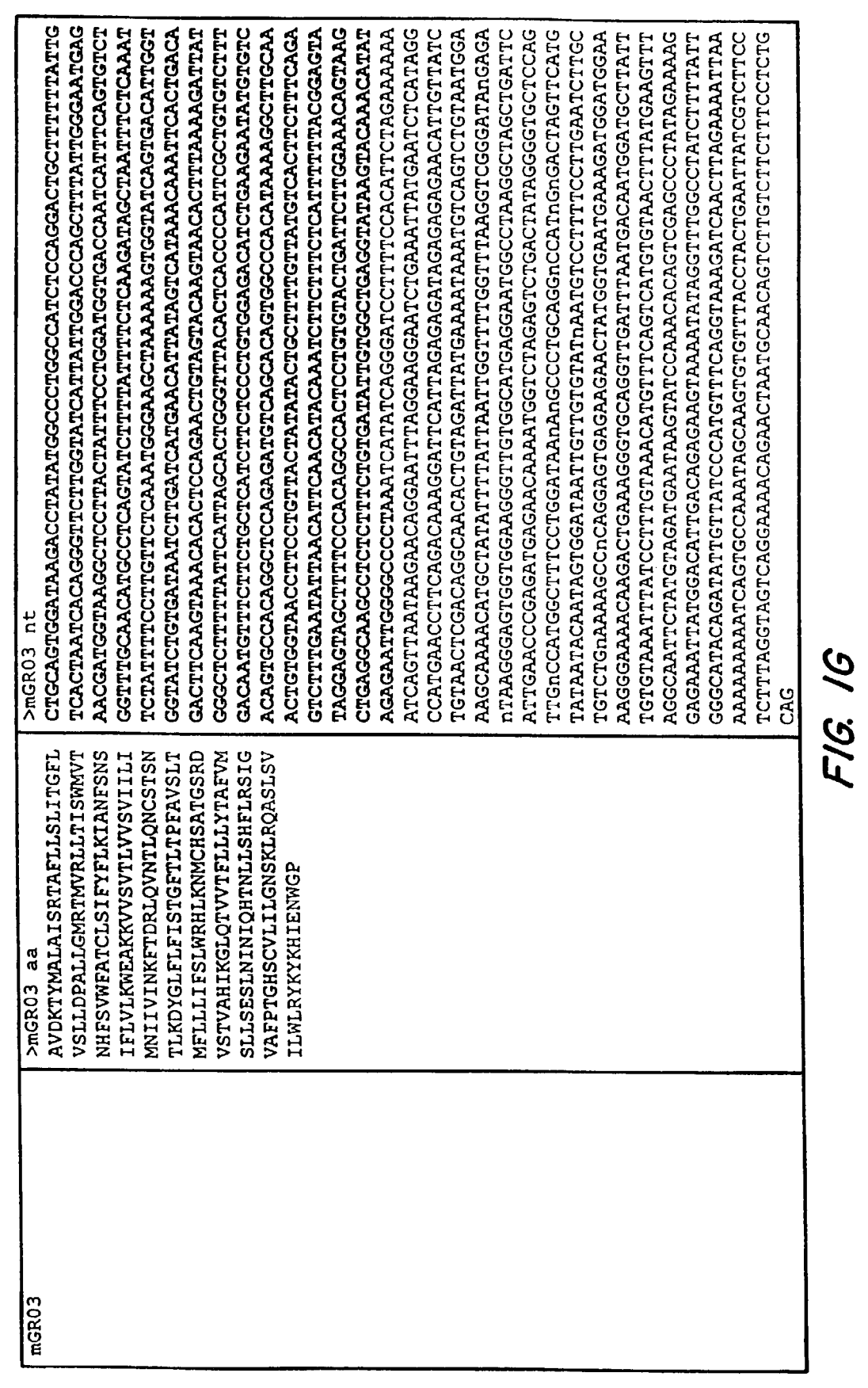

Human psychophysical tasting studies have shown that humans can be categorized as tasters, non tasters, and supertasters for the bitter substance PROP (Bartoshut et al., *Physiol Behav* 58:2994). The genetic locus involed in PROP tasting has been mapped to human interval 5p15 (Reed et al., 1999 *Am. J. Hum. Genet.* 64). Using DNA sequences from this genormic area (using information provided by the National Center for Biotechnology Information website: ncbi.nim.nih.gov), a cumputational analysis was performed to identify novel open reading frames (ORFs) in this interval. The identification of ORFs was facilitated using various programs such as ORF finder, genefinder, fgenesh, etc. (see, e.g., website: imgen.bcm.tmc.edu.). All ORFs larger than 100 amino acids were compared against public databases using BLAST (see, e.g., the National Center for Biotechnology Information), and genes with sequences related to known GPCRs were chosen for further analysis. Candidate sequences were then analyzed for putative transmembrane regions using standard programs (See, e.g, dot. imgen. bcm. tmc. edu),in paticular 7 putative transmembrane segments as expected for a GPCR. In this way, the human Sf01 (GR01) sequence was identified, as shown in FIG. 1 and SEQ ID NOS: 35 and 36. The human Sf01 (GR01) gene maps to genormic region 5p15.

Example II—Identification of the Sf Gene Family

To identify additional Sf genes, sequence databases were searched for sequences homologous to the human Sf01 sequence. Using this screening paradigm, a novel family of GPCRs was identified that includes two genomic clusters of 4 and 9 genes, as well as a number of single loci (see, FIG. 1). A dendogram of various Sf family members is shown as FIG. 2.

The two gene clusters were mapped to human regions 12p13 and 7q31, respectively. Using the jacjson labortory databases of mouse genetics (see, e.g., website: informatics.jax.org), and the human/mouse homology maps from the National Center for Biotechnology Information (NCBI) (website: ncbi.nlm.nih.gov/Homology), the Sf cluster at 12p13 was found to correspond to a cluster of bitter-tasting loci in mice. This chromosmal interval has been proposed to include genes involved in the detection of various bitter substances, including sucruce octaacetate (soa), ruffinose acetate (roa), cycloheximide (cyx), and quinine (qui), and to be tightly linked to Prp on mouse chromosome 6 (Lush et al., Genet. Res. 66:167-174 (1995)). It has been discocered that the Sf cluster at 12p13 is syntentic with this area of mouse chromosome 6, and that it contains Prp.

Example III—Isolation of rat Sf01

In order to isolate rodent homologs of the human Sf gene family members, a rat circumvallate cDNA library was screened for related sequences using low stringency hybridization conditions (7× SSC, 54° C.). Positive clones were picked, rescreened, and sequenced using automated dideoxy sequencing methods. The nucleotide and amino acid sequence of a rat homolog of human Sf01 (GR01) is shown as SEQ ID NOS:1 and 2, respectively.

Example IV—Taste Cell Specific Expression of Human Sf Genes

The expression of human Sf genes in taste cells was determined in two ways: (1) PCR of taste cDNA using primers to Sf family members, and (2) screening of taste cDNA libraries for Sf family members using standard techniques known to those of skill in the art.

What is claimed is:

1. A method for identifying a compound that modulates taste signaling in taste cells, the method comprising the steps of:
   (i) contacting the compound with a taste transduction G-protein coupled receptor polypeptide, wherein the polypeptide is expressed in a taste cell and binds a bitter tastant, the polypeptide comprising greater than about 95% amino acid sequence identity to SEQ ID NO:41; and
   (ii) determining a functional effect of the compound upon the polypeptide, thereby identifying a compound that modulates taste signaling in taste cells.

2. The method of claim 1, wherein the polypeptide has G-protein coupled receptor activity.

3. The method of claim 1, wherein the functional effect is determined by measuring changes in intracellular cAMP, cGMP, IP3, or $Ca^{2+}$.

4. The method of claim 1, wherein the functional effect is a chemical effect.

5. The method of claim 1, wherein the functional effect is a physical effect.

6. The method of claim 1, wherein the functional effect is determined by measuring binding of the compound to an extracellular domain of the polypeptide.

7. The method of claim 1, wherein the functional effect is determined by measuring binding of radiolabeled GTP to the polypeptide.

8. The method of claim 1, wherein the polypeptide is recombinant.

9. The method of claim 1, wherein the polypeptide is from a rat, a mouse, or a human.

10. The method of claim 1, wherein the polypeptide is expressed in a cell or cell membrane.

11. The method of claim 10, wherein the functional effect is measured by determining changes in the electrical activity of cells expressing the polypeptides.

12. The method of claim 10, wherein the cell is a eukaryotic cell.

13. The method of claim 1, wherein the polypeptide comprises SEQ ID NO:41.

14. The method of claim 1, wherein the bitter tastant is 6-n-propylthiouracil, sucrose octaacetate, raffinose undecaacetate, cycloheximide, or quinine.

* * * * *